(12) United States Patent
Goldenberg et al.

(10) Patent No.: US 11,439,620 B2
(45) Date of Patent: *Sep. 13, 2022

(54) SYNERGISTIC EFFECT OF ANTI-TROP-2 ANTIBODY-DRUG CONJUGATE IN COMBINATION THERAPY FOR TRIPLE-NEGATIVE BREAST CANCER WHEN USED WITH MICROTUBULE INHIBITORS OR PARP INHIBITORS

(71) Applicant: Immunomedics, Inc., Morris Plains, NJ (US)

(72) Inventors: David M. Goldenberg, Delray Beach, FL (US); Thomas M. Cardillo, Cedar Knolls, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 244 days.

This patent is subject to a terminal disclaimer.

(21) Appl. No.: 16/204,297

(22) Filed: Nov. 29, 2018

(65) Prior Publication Data

US 2019/0083451 A1 Mar. 21, 2019

Related U.S. Application Data

(60) Division of application No. 15/481,090, filed on Apr. 6, 2017, now Pat. No. 10,195,175, which is a continuation-in-part of application No. 15/190,805, filed on Jun. 23, 2016, now Pat. No. 9,707,302.

(60) Provisional application No. 62/384,423, filed on Sep. 7, 2016, provisional application No. 62/322,429, filed on Apr. 14, 2016, provisional application No. 62/263,134, filed on Dec. 4, 2015, provisional
(Continued)

(51) Int. Cl.
| | |
|---|---|
| A61K 31/35 | (2006.01) |
| A61K 31/4745 | (2006.01) |
| A61K 31/519 | (2006.01) |
| A61K 31/502 | (2006.01) |
| A61K 31/337 | (2006.01) |
| A61K 39/395 | (2006.01) |
| A61K 45/06 | (2006.01) |
| A61K 31/357 | (2006.01) |
| A61K 31/4184 | (2006.01) |
| A61K 31/4375 | (2006.01) |
| A61K 31/454 | (2006.01) |
| A61K 31/513 | (2006.01) |
| A61K 31/675 | (2006.01) |
| A61K 31/7088 | (2006.01) |
| A61K 31/713 | (2006.01) |
| C07K 16/28 | (2006.01) |
| C07K 16/30 | (2006.01) |
| A61K 47/68 | (2017.01) |
| A61K 31/661 | (2006.01) |
| A61K 31/52 | (2006.01) |
| A61K 33/243 | (2019.01) |

(52) U.S. Cl.
CPC .......... *A61K 31/35* (2013.01); *A61K 31/337* (2013.01); *A61K 31/357* (2013.01); *A61K 31/4184* (2013.01); *A61K 31/4375* (2013.01); *A61K 31/454* (2013.01); *A61K 31/4745* (2013.01); *A61K 31/502* (2013.01); *A61K 31/513* (2013.01); *A61K 31/519* (2013.01); *A61K 31/52* (2013.01); *A61K 31/661* (2013.01); *A61K 31/675* (2013.01); *A61K 31/7088* (2013.01); *A61K 31/713* (2013.01); *A61K 33/243* (2019.01); *A61K 39/39558* (2013.01); *A61K 45/06* (2013.01); *A61K 47/6803* (2017.08); *A61K 47/6851* (2017.08); *A61K 47/6853* (2017.08); *C07K 16/2803* (2013.01); *C07K 16/2833* (2013.01); *C07K 16/2887* (2013.01); *C07K 16/30* (2013.01); *C07K 16/3007* (2013.01); *C07K 2317/92* (2013.01); *C07K 2317/94* (2013.01)

(58) Field of Classification Search
CPC ............... A61K 31/35; A61K 47/6851; A61K 47/6803; A61K 47/6853
USPC ................................................... 424/181.1
See application file for complete search history.

(56) References Cited

U.S. PATENT DOCUMENTS

| | | |
|---|---|---|
| 4,036,945 A | 7/1977 | Haber |
| 4,046,722 A | 9/1977 | Rowland |
| | (Continued) | |

FOREIGN PATENT DOCUMENTS

| | | |
|---|---|---|
| EP | 0253202 | 1/1988 |
| EP | 0306943 | 3/1989 |
| | (Continued) | |

OTHER PUBLICATIONS

US 6,558,648 B1, 05/2003, Griffiths et al. (withdrawn)
(Continued)

*Primary Examiner* — Yan Xiao
(74) *Attorney, Agent, or Firm* — Richard A. Nakashima; Achim Brinker

(57) ABSTRACT

The present invention relates to combination therapy with ADCs against a tumor-associated antigen, such as Trop-2, and drugs, such as microtubule inhibitors and/or PARP inhibitors. Where ADCs are used, they preferably incorporate SN-38 or another drug that induces DNA strand breaks. Preferably, the combination of ADC and PARPi or microtubule inhibitor exhibits synergistic effects against the cancer. The combination therapy can reduce solid tumors in size, reduce or eliminate metastases and is effective to treat cancers resistant to standard therapies, such as radiation therapy, chemotherapy or immunotherapy.

13 Claims, 18 Drawing Sheets

Specification includes a Sequence Listing.

Related U.S. Application Data application No. 62/250,715, filed on Nov. 4, 2015, provisional application No. 62/201,361, filed on Aug. 5, 2015, provisional application No. 62/184,331, filed on Jun. 25, 2015.

(56) References Cited

U.S. PATENT DOCUMENTS

| | | |
|---|---|---|
| 4,200,690 A | 4/1980 | Root et al. |
| 4,331,647 A | 5/1982 | Goldenberg |
| 4,359,457 A | 11/1982 | Neville et al. |
| 4,699,784 A | 10/1987 | Shih et al. |
| 4,704,692 A | 11/1987 | Ladner |
| 4,816,567 A | 3/1989 | Cabilly et al. |
| 4,824,659 A | 4/1989 | Howthorne |
| 4,916,213 A | 4/1990 | Scannon et al. |
| 4,918,163 A | 4/1990 | Young et al. |
| 4,925,922 A | 5/1990 | Byers et al. |
| 4,932,412 A | 6/1990 | Goldenberg |
| 4,946,778 A | 8/1990 | Ladner et al. |
| 5,057,313 A | 10/1991 | Shih et al. |
| 5,106,955 A | 4/1992 | Endo et al. |
| 5,112,954 A | 5/1992 | Abrams et al. |
| 5,122,368 A | 6/1992 | Greenfield et al. |
| 5,134,075 A | 7/1992 | Hellstrom et al. |
| 5,171,665 A | 12/1992 | Hellstrom et al. |
| 5,196,337 A | 3/1993 | Ochi et al. |
| 5,204,095 A | 4/1993 | Goodall et al. |
| 5,229,275 A | 7/1993 | Goroff |
| 5,443,953 A | 8/1995 | Hansen et al. |
| 5,484,892 A | 1/1996 | Tedder et al. |
| 5,525,338 A | 6/1996 | Goldenberg |
| 5,565,215 A | 10/1996 | Gref et al. |
| 5,567,610 A | 10/1996 | Borrebaeck et al. |
| 5,593,676 A | 1/1997 | Bhat et al. |
| 5,618,920 A | 4/1997 | Robinson et al. |
| 5,620,708 A | 4/1997 | Amkraut et al. |
| 5,633,425 A | 5/1997 | Lonberg et al. |
| 5,679,640 A | 10/1997 | Gaeta et al. |
| 5,686,072 A | 11/1997 | Uhr et al. |
| 5,693,762 A | 12/1997 | Queen et al. |
| 5,698,178 A | 12/1997 | Goldenberg |
| 5,702,727 A | 12/1997 | Amkraut et al. |
| 5,708,146 A | 1/1998 | Willner et al. |
| 5,716,595 A | 2/1998 | Goldenberg |
| 5,736,119 A | 4/1998 | Goldenberg et al. |
| 5,750,105 A | 5/1998 | Newman et al. |
| 5,776,456 A | 7/1998 | Anderson et al. |
| 5,789,554 A | 8/1998 | Leung et al. |
| 5,792,845 A | 8/1998 | O'Reilly et al. |
| 5,795,967 A | 8/1998 | Aggarwal et al. |
| 5,798,554 A | 8/1998 | Grimaldi et al. |
| 5,817,307 A | 10/1998 | Cummins |
| 5,824,701 A | 10/1998 | Greenwald et al. |
| 5,874,540 A | 2/1999 | Hansen et al. |
| 5,922,302 A | 7/1999 | Goldenberg et al. |
| 6,051,228 A | 4/2000 | Aruffo et al. |
| 6,051,230 A | 4/2000 | Thorpe et al. |
| 6,056,973 A | 5/2000 | Allen et al. |
| 6,077,499 A | 6/2000 | Griffiths et al. |
| 6,096,289 A | 8/2000 | Goldenberg |
| 6,156,754 A | 12/2000 | Lerchen et al. |
| 6,165,440 A | 12/2000 | Esenaliev |
| 6,183,744 B1 | 2/2001 | Goldenberg |
| 6,187,287 B1 | 2/2001 | Leung et al. |
| 6,201,104 B1 | 3/2001 | MacDonald et al. |
| 6,214,345 B1 | 4/2001 | Firestone et al. |
| 6,254,868 B1 | 7/2001 | Leung et al. |
| 6,306,393 B1 | 10/2001 | Goldenberg |
| 6,331,175 B1 | 12/2001 | Goldenberg |
| 6,379,698 B1 | 4/2002 | Leamon |
| 6,387,350 B2 | 5/2002 | Goldenberg |
| 6,395,276 B1 | 5/2002 | Rybak et al. |
| 6,530,944 B2 | 3/2003 | West et al. |
| 6,562,318 B1 | 5/2003 | Filler |
| 6,653,104 B2 | 11/2003 | Goldenberg |
| 6,716,821 B2 | 4/2004 | Zhao et al. |
| 7,018,809 B1 | 5/2006 | Carter |
| 7,074,403 B1 | 7/2006 | Goldenberg et al. |
| 7,122,636 B1 | 10/2006 | Hsei et al. |
| 7,151,164 B2 | 12/2006 | Hansen et al. |
| 7,238,785 B2 | 7/2007 | Govindan et al. |
| 7,312,318 B2 | 12/2007 | Hansen et al. |
| 7,387,779 B2 | 6/2008 | Kalluri |
| 7,517,964 B2 | 4/2009 | Govindan et al. |
| 7,585,491 B2 | 9/2009 | Govindan et al. |
| 7,591,994 B2 | 9/2009 | Govindan et al. |
| 7,612,180 B2 | 11/2009 | Goldenberg et al. |
| 7,772,373 B2 | 8/2010 | Hansen et al. |
| 7,820,161 B1 | 10/2010 | Curd et al. |
| 7,910,103 B2 | 3/2011 | Goldenberg |
| 7,931,903 B2 | 4/2011 | Hansen et al. |
| 7,999,083 B2 | 8/2011 | Govindan et al. |
| 8,080,250 B1 | 12/2011 | Govindan et al. |
| 8,084,583 B2 | 12/2011 | Govindan et al. |
| 8,119,101 B2 | 2/2012 | Byrd et al. |
| 8,268,317 B2 | 9/2012 | Govindan et al. |
| 8,268,319 B2 | 9/2012 | Govindan et al. |
| 8,309,094 B2 | 11/2012 | Gerber et al. |
| 8,420,086 B2 | 4/2013 | Govindan et al. |
| 8,425,912 B2 | 4/2013 | Govindan et al. |
| 8,586,049 B2 | 11/2013 | Gerber et al. |
| 8,613,903 B2 | 12/2013 | Goldenberg et al. |
| 8,658,773 B2 | 2/2014 | Zeng et al. |
| 8,722,047 B2 | 5/2014 | Goldenberg et al. |
| 8,871,908 B2 | 10/2014 | Liu et al. |
| 8,992,917 B2 | 3/2015 | Goldenberg et al. |
| 9,028,833 B2 | 5/2015 | Govindan et al. |
| 9,180,205 B2 | 11/2015 | Zeng et al. |
| 9,187,561 B2 | 11/2015 | Goldenberg et al. |
| 9,492,566 B2 | 11/2016 | Goldenberg et al. |
| 9,707,302 B2 | 7/2017 | Goldenberg et al. |
| 10,195,175 B2 * | 2/2019 | Goldenberg ......... A61K 31/513 |
| 10,266,605 B2 * | 4/2019 | Govindan ............. A61K 45/06 |
| 10,653,793 B2 * | 5/2020 | Goldenberg ....... A61K 47/6859 |
| 10,669,338 B2 * | 6/2020 | Chang ................ C07K 16/2818 |
| 10,682,347 B2 * | 6/2020 | Govindan ............... A61P 35/02 |
| 11,116,846 B2 * | 9/2021 | Goldenberg ......... A61K 31/675 |
| 2001/0034363 A1 | 10/2001 | Li et al. |
| 2002/0018749 A1 | 2/2002 | Hudson et al. |
| 2003/0103979 A1 | 6/2003 | Leung et al. |
| 2003/0133972 A1 | 7/2003 | Danthi et al. |
| 2004/0001838 A1 | 1/2004 | Zhao et al. |
| 2004/0076683 A1 | 4/2004 | Hoarau et al. |
| 2006/0142506 A1 | 6/2006 | Breitenkamp et al. |
| 2006/0193865 A1 | 8/2006 | Govindan et al. |
| 2007/0212350 A1 | 9/2007 | Govindan et al. |
| 2008/0166363 A1 | 7/2008 | Govindan et al. |
| 2010/0104589 A1 | 4/2010 | Govindan et al. |
| 2011/0070156 A1 | 3/2011 | Govindan et al. |
| 2011/0160159 A1 | 6/2011 | Ryan |
| 2011/0171126 A1 | 7/2011 | Burton et al. |
| 2011/0256053 A1 | 10/2011 | Chang et al. |
| 2011/0274704 A1 | 11/2011 | Chang et al. |
| 2011/0305631 A1 | 12/2011 | Govindan et al. |
| 2012/0052076 A1 | 3/2012 | Alberti |
| 2012/0082617 A1 | 4/2012 | Govindan et al. |
| 2012/0328564 A1 | 12/2012 | Govindan et al. |
| 2013/0089872 A1 | 4/2013 | Nakamura et al. |
| 2013/0090458 A1 | 4/2013 | Govindan et al. |
| 2013/0122020 A1 | 5/2013 | Liu et al. |
| 2013/0177526 A1 | 7/2013 | Govindan et al. |
| 2013/0216561 A1 | 8/2013 | Govindan et al. |
| 2014/0004078 A1 | 1/2014 | Govindan et al. |
| 2014/0099254 A1 | 4/2014 | Chang et al. |
| 2014/0178294 A1 | 6/2014 | Zeng et al. |
| 2014/0219914 A1 | 8/2014 | Govindan et al. |
| 2014/0286969 A1 | 9/2014 | Tschoepe et al. |
| 2015/0132217 A1 | 5/2015 | Chang et al. |
| 2015/0166659 A1 | 6/2015 | Goldenberg et al. |

(56) References Cited

U.S. PATENT DOCUMENTS

| | | | |
|---|---|---|---|
| 2016/0024212 | A1 | 1/2016 | Goldenberg et al. |
| 2016/0032008 | A1 | 2/2016 | Zeng et al. |

FOREIGN PATENT DOCUMENTS

| | | |
|---|---|---|
| EP | 0332865 | 9/1989 |
| EP | 0510949 | 10/1992 |
| WO | 90/09196 | 8/1990 |
| WO | 91/11465 | 8/1991 |
| WO | 91/13974 | 9/1991 |
| WO | 94/27638 | 12/1994 |
| WO | 9509917 | 4/1995 |
| WO | 96/04925 | 2/1996 |
| WO | 98/04281 | 2/1998 |
| WO | 98/42378 | 10/1998 |
| WO | 98/50435 | 11/1998 |
| WO | 99/02567 | 1/1999 |
| WO | 99/54440 | 10/1999 |
| WO | 00/29584 | 5/2000 |
| WO | 00/67795 | 11/2000 |
| WO | 00/67796 | 11/2000 |
| WO | 0074718 | 12/2000 |
| WO | 0076551 | 12/2000 |
| WO | 0124763 | 4/2001 |
| WO | 2003070234 | 8/2003 |
| WO | 2004054622 | 7/2004 |
| WO | 2006094192 | 9/2006 |
| WO | 2007123995 | 11/2007 |
| WO | 2010089782 | 8/2010 |
| WO | 2012151199 | 11/2012 |
| WO | 2014124227 | 8/2014 |
| WO | 2015047510 | 4/2015 |
| WO | 2015069430 | 5/2015 |

OTHER PUBLICATIONS

Durvalumab-MeSH-NCBI, Dec. 16, 2020, p. 1.*
Aprile et al., "Tracking the 2015 Gastrointestinal Cancers Symposium: bridging cancer biology to clinical gastrointestinal oncology", Onco Targets Ther. May 22, 2015;8:1149-56.
Bardia et al., "IMMU-132, a new antibody-drug conjugate (ADC) against Trop-2, as a novel therapeutic for patients with relapsed/refractory, metastatic, triple-negative breast cancer (TNBC): Results from Phase I/II clinical trial (NCT01631552)", Poster, San Antonio Breast Cancer Symposium, Dec. 9-13, 2014.
Bardia et al., "Therapy of refractory/relapsed metastatic triple-negative breast cancer (TNBC) with an anti-Trop-2-SN-38 antibody-drug conjugate (ADC), sacituzumab govitecan (IMMU-132): Phase I/II clinical experience", J Clin Oncol 33, 2015 (suppl; abstr 1016), Retrieved from http://meetinglibrary.asco.org/content/150673-156.
Byrne et al., "Special Conference on Tumor Immunology and Immunotherapy: A New Chapter", Cancer Immunol Res. Jun. 2015;3(6):590-597.
Cardillo et al., "Significant enhancement of efficacy of an anti-Trop-2 antibody-drug conjugate, sacituzumab govitecan (IMMU-132), in experimental triple-negative breast cancer (TNBC) when combined with microtubule or PARP inhibitors", Cancer Res. Jul. 15, 2016; (76) (14 Supplement), Abstract 584.
Cardillo et al., "Synthetic Lethality Exploitation by an Anti-Trop-2-SN-38 Antibody-Drug Conjugate, IMMU-132, Plus PARP Inhibitors in BRCA1/2-wild-type Triple-Negative Breast Cancer", Clin Cancer Res. Jul. 1, 2017;23(13):3405-3415.
Chen et al., "The humanized anti-HLA-DR moAb, IMMU-114, depletes APCs and reduces alloreactive T cells mplications for preventing GVHD", Bone Marrow Transplant. Jul. 2012;47(7):967-80.
Dang et al., "Hypoxia-inducible factor-1 target genes as indicators of tumor vessel response to vascular endothelial growth factor inhibition", Cancer Res. Mar. 15, 2008;68(6):1872-80.
Declaration under 37 C.F.R. 1.132 by David M. Goldenberg, filed in U.S. Appl. No. 13/948,732, filed Jun. 20, 2014.
Declaration under 37 C.F.R. 1.132 by David M. Goldenberg, filed in U.S. Appl. No. 14/204,698, filed Jan. 7, 2015.
Dotan et al., "A new anti-CEA-SN-38 antibody-drug conjugate (ADC), IMMU-130, is active in controlling metastatic colorectal cancer (mCRC) in patients (pts) refractory or relapsing after irinotecan-containing chemotherapies: Initial results of a phase I/II study", J Clin Oncol 33, 2015 (suppl; abstr 2505), Retrieved from http://meetinglibrary.asco.org/content/148390-156.
Faltas et al., "Sacituzumab Govitecan, a Novel Antibody-Drug Conjugate, in Patients With Metastatic Platinum-Resistant Urothelial Carcinoma", Clin Genitourin Cancer. Feb. 2016;14(1):e75-9.
Goldenberg et al., "Selective in vivo therapeutic efficacies of SN-38 conjugates of an anti-CEACAM5 antibody in preclinical models of human colon carcinoma", Presentation, ASCO 2009 Gastrointestinal Cancers Symposium, San Francisco, CA, Jan. 15-17, 2009.
Goldenberg, D.M., "Challenging the Dogmas: Clinical Efficacy of SN-38-Conjugated Antibodies in Solid Tumors", 26th EORTC-NCI-AACR Symposium on Molecular Targets and Cancer Therapeutics, Barcelona, Spain, Nov. 18-21, 2014.
Goldenberg, D.M., "SN-38 Conjugates for Therapy of Advanced Solid Cancers", 5th Annual World ADC Summit in San Diego, CA, Oct. 26-29, 2014.
Goldenberg et al., "Therapy of human solid tumor xenografts with CD74-targeted milatuzumab-SN-38 immunoconjugates". Poster, 2012 ASCO Annual Meeting, Chicago, IL, Jun. 1-5, 2012.
Goldenberg et al., "Improved Therapeutic Index of IMMU-132 ADC vs. Irinotecan in Preclinical Studies", Presentation, AACR Annual Meeting, San Diego, CA, Apr. 5-9, 2014.
Goldenberg et al., "Tolerability in mice, monkeys, and rabbits of new antibody (MAb)-drug (SN-38) immunoconjugates", Proceedings of the 102nd Annual Meeting of the American Association for Cancer Research; Apr. 2-6, 2011; Orlando, FL. Cancer Res 2011;71(8 Suppl):Abstract #3619.
Goldenberg et al., "Synthetic lethality in TNBC mediated by an anti-Trop-2 antibody-drug conjugate, sacituzumab govitecan (IMMU-132), when combined with paclitaxel or the PARP inhibitor, olaparib", Cancer Res. Feb. 15, 2016, (76) (4 Suppl), Abstract P6-15-02.
Goldenberg, DM., "The role of radiolabeled antibodies in the treatment of non-Hodgkin's lymphoma: the coming of age of radioimmunotherapy", Crit Rev Oncol Hematol. Jul.-Aug. 2001;39(1-2):195-201.
Gorman, G., "Focused on Therapy: Cancer, Autoimmune & Other Serious Diseases", Presentation, Oppenheimer 23rd Annual Healthcare Conference, NYC, Dec. 12, 2012.
Govindan et al., "Targeted therapy of human colonic, lung, and pancreatic cancer xenografts, growing in nude mice, with potent antibody conjugates of SN-38", Poster, AACR 100th Annual Meeting, Denver, CO, Apr. 18-22, 2009.
Govindan et al., "Efficacious therapies of two human pancreatic cancer xenografts and an aggressive human lymphoma xenograft with redesigned antibody-SN-38 conjugates", Poster, AACR 101st Annual Meeting, Washington, DC, Apr. 17-21, 2010.
Govindan et al., "Improving the Therapeutic Index in Cancer Therapy by Using Antibody-Drug Conjugates Designed with a Moderately Cytotoxic Drug", Mol Pharm. Nov. 25, 2014. [Epub ahead of print].
Govindan et al., "Optimal cleavable linker for antibody-SN-38 conjugates for cancer therapy: Impact of linker's stability on efficacy", Poster, AACR 103rd Annual Meeting, Chicago, IL, Mar. 31-Apr. 4, 2012.
Govindan et al., "CEACAM5-targeted therapy of human colonic and pancreatic cancer xenografts with potent labetuzumab-SN-38 immunoconjugates", Clin Cancer Res. Oct. 1, 2009;15(19):6052-61.
Govindan et al., "IMMU-130, a unique antibody-drug conjugate (ADC) of SN-38 targeting CEACAM5 antigen: Preclinical basis for clinical activity in metastatic colorectal cancer (mCRC)", J Clin Oncol 33, 2015 (suppl 3; abstr 625), Retrieved from http://meetinglibrary.asco.org/content/139777-158.
Karacay et al., "Combining antibody-targeted radiation (radioimmunotherapy) and antibody-SN-38 conjugates (ADC) improves pancreatic cancer therapy", Poster, AACR 101st Annual Meeting, Washington, DC, Apr. 17-21, 2010.

(56) References Cited

OTHER PUBLICATIONS

Liu et al., "Interferon-λ1 linked to a stabilized dimer of Fab potently enhances both antitumor and antiviral activities in targeted cells", PLoS One. May 16, 2013;8(5):e63940.
Michel et al., "Therapy of small subcutaneous B-lymphoma xenografts with antibodies conjugated to radionuclides emitting low-energy electrons", Clin Cancer Res. Jan. 15, 2005;11(2 Pt 1):777-86.
Michel et al., "177Lu-antibody conjugates for single-cell kill of B-lymphoma cells in vitro and for therapy of micrometastases in vivo", Nucl Med Biol. Apr. 2005;32(3):269-78.
Moon et al., "Cross-linker evaluation in the design of antibody-SN-38 conjugates for cancer therapy", Poster, AACR 101st Annual Meeting, Washington, DC, Apr. 17-21, 2010.
Park et al., "Anti-class II—DR humanized monoclonal antibody, IMMU-114, blocks allogeneic immune response", Am J Surg. Oct. 2012;204(4):527-34.
Reagan-Shaw et al., "Dose translation from animal to human studies revisited", FASEB J. Mar. 2008;22(3):659-61.
Rossi et al., "Preclinical studies on targeted delivery of multiple IFNα2b to HLA-DR in diverse hematologic cancers", Blood Aug. 18, 2011; 118(7):1877-84.
Rossi et al., "A bispecific antibody-IFNalpha2b immunocytokine targeting CD20 and HLA-DR is highly toxic to human lymphoma and multiple myeloma cells", Cancer Res Oct. 1, 2010;70(19):7600-9.
Segal et al., "IMMU-130, an SN-38 antibody-drug conjugate (ADC) targeting CEACAM5, is therapeutically active in metastatic colorectal cancer (mCRC): Initial clinical results of two Phase I studies", Presentation, AACR Annual Meeting, San Diego, CA, Apr. 5-9, 2014.
Segal et al., "IMMU-130, an SN-38 antibody-drug conjugate (ADC) targeting CEACAM5, is therapeutically active in metastatic colorectal cancer (mCRC): Initial clinical results of two Phase I studies", 2014 AACR Meeting April 5-9, 2-14, San Diego, CA (Abstract No. CT211).
Seruga et al., "Failures in Phase III: Causes and Consequences", Clin Cancer Res. Oct. 15, 2015;21(20):4552-60.
Starodub et al., "IMMU-132, an SN-38 antibody-drug conjugate (ADC) targeting Trop-2, as a novel platform for the therapy of diverse metastatic solid cancers: Clinical results", Poster, the 2014 Annual Meeting of the American Society of Clinical Oncology (ASCO), May 30-Jun. 3, 2014.
Stein et al., "Characterization of a humanized IgG4 anti-HLA-DR monoclonal antibody that lacks effector cell functions but retains direct antilymphoma activity and increases the potency of rituximab", Blood. Oct. 15, 2006;108(8):2736-44.
Stein et al., "Therapy of B-cell malignancies by anti-HLA-DR humanized monoclonal antibody, IMMU-114, is mediated through hyperactivation of ERK and JNK MAP kinase signaling pathways", Blood. Jun. 24, 2010;115(25):5180-90.
Stein et al., "Evaluation of anti-human leukocyte antigen-DR monoclonal antibody therapy in spontaneous canine lymphoma", Leuk Lymphoma. Feb. 2011;52(2):273-84.
Tahara et al., "The Use of Olaparib (AZD2281) Potentiates SN-38 Cytotoxicity in Colon Cancer Cells by Indirect Inhibition of Rad51-Mediated Repair of DNA Double-Strand Breaks", Mol Cancer Ther; 13(5); 1170-80 (2014).
Chen et al., "The humanized anti-HLA-DR moAb, IMMU-114, depletes APCs and reduces alloreactive T cells: implications for preventing GVHD", Bone Marrow Transplant Jul. 2012;47(7):967-80.
Goldenberg et al., "Therapy of human solid tumor xenografts with CD74-targeted milatuzumab-SN-38 mmunoconjugates", Poster, 2012 ASCO Annual Meeting, Chicago, IL, Jun. 1-5, 2012.
Goldenberg et al., "Tolerability in mice, monkeys, and rabbits of new antibody (MAb)-drug (SN-38) immunoconjugates", Proceedings of the 102nd Annual Meeting of the American Association for Cancer Research; 2011 Apr. 2-6; Orlando, FL. Cancer Res 2011;71(8 Suppl):Abstract #3619.
Liu et al., "Interferon-λ1 linked to a stabilized dimer of Fab potently enhances both antitumor and antiviral activities in targeted cells", PLoS One. May 16, 2013;8(5):e63940.
Segal et al., "IMMU-130, an SN-38 antibody-drug conjugate (ADC) targeting CEACAM5, is therapeutically active in metastatic colorectal cancer (mCRC): Initial clinical results of two Phase I studies", 2014 AACR Meeting Apr. 5-9, 2-14, San Diego, CA (Abstract No. CT211).
Alberti et al., "Biochemical characterization of Trop-2, a cell surface molecule expressed by human carcinomas: formal proof that the monoclonal antibodies T16 and MOv-16 recognize Trop-2", Hybridoma. Oct. 1992;11(5):539-45.
Bao et al., "PRSS8 methylation and its significance in esophageal squamous cell carcinoma", Oncotarget. May 10, 2016;7(19):28540-55.
Bardia et al., "Efficacy and Safety of Anti-Trop-2 Antibody Drug Conjugate Sacituzumab Govitecan (IMMU-132) in Heavily Pretreated Patients With Metastatic Triple-Negative Breast Cancer", J Clin Oncol. Mar. 14, 2017 [Epub ahead of print].
Bignotti et al., "Trop-2 protein overexpression is an independent marker for predicting disease recurrence in endometrioid endometrial carcinoma", BMC Clin Pathol. Nov. 14, 2012;12:22.
Chang et al., "Ranpirnase (frog RNase) targeted with a humanized, internalizing, anti-Trop-2 antibody has potent cytotoxicity against diverse epithelial cancer cells", Mol Cancer Ther. Aug. 2010;9(8):2276-86.
Chen et al., "Increased expression of Trop2 correlates with poor survival in extranodal NK/T cell lymphoma, nasal type", Virchows Arch. Nov. 2013;463(5):713-9.
Cubas et al., "Trop2: a possible therapeutic target for late stage epithelial carcinomas", Biochim Biophys Acta. Dec. 2009;1796(2):309-14.
Cubas et al., "Trop2 expression contributes to tumor pathogenesis by activating the ERK MAPK pathway", Mol Cancer. Sep. 21, 2010;9:253.
Fang et al., "Different effects of ERβ and TROP2 expression in Chinese patients with early-stage colon cancer", Tumour Biol. Dec. 2012;33(6):2227-35.
Farivar et al., "Nano—drug Delivery of Apoptosis Activator 2 to AGS Cells by Liposomes Conjugated with Anti-TROP2 Antibody", N Am J Med Sci. Nov. 2012;4(11):582-5.
Friedman et al., "BR96 sFv-PE40, a potent single-chain immunotoxin that selectively kills carcinoma cells", Cancer Res. Jan. 15, 1993;53(2):334-9.
Govindan et al., "Designing immunoconjugates for cancer therapy", Expert Opin Biol Ther. Jul. 2012;12(7):873-90.
Jefferis et al., "Human immunoglobulin allotypes: possible implications for immunogenicity", MAbs. Jul.-Aug. 2009;1(4):332-8.
Kapoor, S., "TROP2 expression and its evolving role in tumor pathogenesis in systemic tumors", Tumour Biol. Jun. 2013;34(3):1967-8.
Koizumi et al., "Novel SN-38-incorporating polymeric micelles, NK012, eradicate vascular endothelial growth factor-secreting bulky tumors", Cancer Res. Oct. 15, 2006;66(20):10048-56.
Lin et al., "Significantly upregulated TACSTD2 and Cyclin D1 correlate with poor prognosis of invasive ductal breast cancer", Exp Mol Pathol. Feb. 2013;94(1):73-8.
Lin et al., "A novel human Fab antibody for Trop2 inhibits breast cancer growth in vitro and in vivo", Int J Cancer. Mar. 1, 2014;134(5):1239-49.
Lipinski et al., "Human trophoblast cell-surface antigens defined by monoclonal antibodies", Proc Natl Acad Sci U S A. Aug. 1981;78(8):5147-50.
Liu et al., "Overexpression of TROP2 predicts poor prognosis of patients with cervical cancer and promotes the proliferation and invasion of cervical cancer cells by regulating ERK signaling pathway", PLoS One. Sep. 2, 20137;8(9):e75864.
Liu et al., "Trop-2-targeting tetrakis-ranpimase has potent antitumor activity against triple-negative breast cancer", Mol Dancer. Mar. 10, 2014;13:53.

(56) References Cited

OTHER PUBLICATIONS

Lorusso et al., "Trastuzumab emtansine: a unique antibody-drug conjugate in development for human epidermal growth factor receptor 2-positive cancer", Clin Cancer Res Oct. 15, 2011;17(20):6437-47.
Ning et al., "TROP2 correlates with microvessel density and poor prognosis in hilar cholangiocarcinoma", J Gastrointest Surg Feb. 2013;17(2):360-8.
Ning et al., "TROP2 expression and its correlation with tumor proliferation and angiogenesis in human gliomas", Neurol Sci Oct. 2013;34(10):1745-50.
Pak et al., "Significance of EpCAM and TROP2 expression in non-small cell lung cancer", World J Surg Oncol. Apr. 6, 2012;10:53.
Pro et al., "Brentuximab vedotin in Hodgkin's lymphoma", Expert Opin Biol Ther. Oct. 2012; 12(10):1415-21.
Ripani et al., "Human Trop-2 is a tumor-associated calcium signal transducer", Int J Cancer. May 29, 1998;76(5):671-6.
Rouleau et al., "PARP inhibition: PARP1 and beyond", Nat Rev Cancer. Apr. 2010;10(4):293-301.
Samol et al., "Safety and tolerability of the poly(ADP-ribose) polymerase (PARP) inhibitor, olaparib (AZD2281) in combination with topotecan for the treatment of patients with advanced solid tumors: a phase I study", Invest New Drugs. Aug. 2012;30(4):1493-500.
Sapra et al., "Long-term tumor regression induced by an antibody-drug conjugate that targets 5T4, an oncofetal antigen expressed on tumor-initiating cells", Mol Cancer Ther. Jan. 2013;12(1):38-47.
Sapra et al., "Novel delivery of SN38 markedly inhibits tumor growth in xenografts, including a camptothecin-11-refractory model", Clin Cancer Res. Mar. 15, 2008;14(6):1888-96.
Sapra et al., "Marked therapeutic efficacy of a novel polyethylene glycol-SN38 conjugate, EZN-2208, in xenograft models of B-cell non-Hodgkin's lymphoma", Haematologica. Oct. 2009;94(10):1456-9.
Sapra et al., "Investigational antibody drug conjugates for solid tumors", Expert Opin Investig Drugs. Aug. 2011;20(8):1131-49.
Sharkey et al., "Targeted therapy of cancer: new prospects for antibodies and immunoconjugates", CA Cancer J Clin Jul.-Aug. 2006;56(4):226-43.
Shi et al., "In vitro and in vivo reactivity of an internalizing antibody, RS7, with human breast cancer", Cancer Res. Dec. 1, 1995;55(23 Suppl):5857s-5863s.
Shor et al., "Enhanced Antitumor Activity of an Anti-5T4 Antibody-Drug Conjugate in Combination with PI3K/mTOR inhibitors or Taxanes", Clin Cancer Res. Jan. 15, 2016;22(2):383-94.
Shvartsur et al., "Trop2 and its overexpression in cancers: regulation and clinical/therapeutic implications", Genes Cancer. Mar. 2015,6(3-4):84-105.
Stein et al., "Radioimmunotherapy of a human lung cancer xenograft with monoclonal antibody RS7: evaluation of (177)Lu and comparison of its efficacy with that of (90)Y and residualizing (131)I", J Nucl Med. Jun. 2001;42(6):967-74.
Stein et al., "Advantage of yttrium-90-labeled over iodine-131-labeled monoclonal antibodies in the treatment of a human lung carcinoma xenograft", Cancer. Dec. 15, 1997;80(12 Suppl):2636-41.
Stepan et al., "Expression of Trop2 cell surface glycoprotein in normal and tumor tissues: potential implications as a Dancer therapeutic target", J Histochem Cytochem. Jul. 2011;59(7):701-10.
Stoyanova et al., "Regulated proteolysis of Trop2 drives epithelial hyperplasia and stem cell self-renewal via β-catenin signaling", Genes Dev. Oct. 15, 2012;26(20):2271-85.
Trerotola et al., "Letter to the editor: efficacy and safety of anti-Trop antibodies, R. Cubas, M. Li, C. Chen and Q. Yao, Biochim Biophys Acta 1796 (2009) 309-1", Biochim Biophys Acta Apr. 2010;1805(2):119-20.
Tsukahara et al., "TROP2 expressed in the trunk of the ureteric duct regulates branching morphogenesis during kidney development", PLoS One. 2011;6(12):e28607.

Varughese et al., "Cervical carcinomas overexpress human trophoblast cell-surface marker (Trop-2) and are highly sensitive to immunotherapy with hRS7, a humanized monoclonal anti-Trop-2 antibody", Am J Obstet Gynecol. Dec. 2011;205(6):567.e1-7.
Vidmar et al., "Biochemical and preliminary X-ray characterization of the tumor-associated calcium signal transducer 2 (Trop2) ectodomain", Protein Expr Purif. Sep. 2013;91(1):69-76.
Voskoglou-Nomikos et al., "Clinical predictive value of the in vitro cell line, human xenograft, and mouse allograft preclinical cancer models", Clin Cancer Res Sep. 15, 2003;9(11):4227-39.
Wang et al., "Identification of Trop-2 as an oncogene and an attractive therapeutic target in colon cancers", Mol Dancer Ther Feb. 2008;7(2):280-5.
Wang et al., "Loss of Trop2 promotes carcinogenesis and features of epithelial to mesenchymal transition in squamous cell carcinoma", Mol Cancer Res. Dec. 2011;9(12):1686-95.
Weisenthal, http://weisenthal.org/feedback.html, Feb. 4, 2002.
Wu et al., "Potential therapeutic target and independent prognostic marker of TROP2 in laryngeal squamous cell carcinoma". Head Neck. Oct. 2013;35(10):1373-8.
Zhao et al., "Novel prodrugs of SN38 using multiarm poly(ethylene glycol) linkers", Bioconjug Chem. Apr. 2008;19(4):849-59.
Ausubel et al., (eds.), Current Protocols in Molecular Biology, pp. 8.2.8-8.2.13, John Wiley & Sons, Inc. (1990).
Ausubel et al., (eds.), Short Protocols in Molecular Biology, pp. 8.8-8.10, John Wiley & Sons, Inc. (1995).
Baines et al., "Purification of Immunoglobulin G (IgG)", Methods in Molecular Biology, vol. 10, pp. 79-104, Manson et al., (eds.), The Human Press (1992).
Bambot et al., "Efficient total gene synthesis of 1.35-kb hybrid alpha-lytic protease gene using the polymerase chain reaction", PCR Methods Appl. Feb. 1993;2(3):266-71.
Baum et al., "Initial clinical results with technetium-99m-labeled LL2 monoclonal antibody fragment in the radioimmunodetection of B-cell lymphomas", Cancer. Feb. 1, 1994 ;73(3 Suppl):896-9.
Beers et al., The Merck Manual of Diagnosis and Therapy, Ch. 180, p. 1474-1476; 17th Ed., Whitehouse Station, NJ, Merck Research Labs (1999).
Belisle et al., "Epitope specificity of the anti-B-cell lymphoma monoclonal antibody, LL2", Proc Am Assoc Cancer Res 1993; 34:481, Abstr #2873.
Bendig, M., "Humanization of Rodent Monoclonal Antibodies by CDR Grafting", Academic Press Inc., New York, NY, vol. 8, (1995), pp. 83-93.
Bhat et al., "Human antilipid A monoclonal antibodies bind to human B cells and the i antigen on cord red blood cells", J Immunol. Nov. 1, 1993 ;151(9):5011-21.
Carter et al., "Humanization of an anti-p185HER2 antibody for human cancer therapy", Proc. Natl. Acad. Sci. USA 89(10):4285-9 (1992).
Coligan et al., (Eds.), Current Protocols in Immunology, vol. 1, pp. 2.5.1-2.6.7; pp. 2.7.1.-2.7.12; pp. 2.8.1-2.8.10; pp. 2.9.1-2.9.3; pp. 2.10.-2.10.4; John Wiley & Sons, Inc., 1991.
Coloma et al., "Design and production of novel tetravalent bispecific antibodies", Nat. Biotechnol. 15(2):159-63 (1997).
Dillon et al., "Use of Polymerase Chain Reaction for the Rapid Construction of Synthetic Genes", Methods in Molecular Biology, vol. 15: PCR Protocols: Current Methods and Applications, White (Ed.), pp. 263-268, Humana Press, Inc. (1993).
Ellis et al., "Engineered anti-CD38 monoclonal antibodies for immunotherapy of multiple myeloma", J Immunol. Jul. 15, 1995;155(2):925-37.
Flavell et al., "Systemic therapy with 3BIT, a triple combination cocktail of anti-CD19, -CD22, and -CD38-saporin immunotoxins, is curative of human B-cell lymphoma in severe combined immuno-deficient mice", Cancer Res. 57:4824-9 (1997).
Foy et al., "In vivo CD40-gp39 interactions are essential for thymus-dependent humoral immunity. II. Prolonged suppression of the humoral immune response by an antibody to the ligand for CD40, gp39", J Exp Med. Nov. 1, 1993;178(5):1567-75.
French et al., "Response of B-cell lymphoma to a combination of bispecific antibodies and saporin", Leuk. Res. 20(7):607-17 (1996).

(56) References Cited

OTHER PUBLICATIONS

Ghetie et al., "Evaluation of ricin A chain-containing immunotoxins directed against CD19 and CD22 antigens on normal and malignant human B-cells as potential reagents for in vivo therapy", Cancer Res. 48(9):2610-7 (1988).
Goldenberg et al., "Targeting, dosimetry, and radioimmunotherapy of B-cell lymphomas with iodine-131-labeled LL2 monoclonal antibody", J Clin Oncol. Apr. 1991;9(4):548-64.
Goldenberg, D. M., "New Developments in Monoclonal Antibodies for Cancer Detection and Therapy", CA Cancer J. Clin. 44(1):43-64 (1994).
Goldenberg et al., "Epratuzumab (Humanized Anti-CD22 MAb) Conjugated with SN-38, a New Antibody-Drug Conjugate (ADC) for the Treatment of Hematologic Tumors: Preclinical Studies Alone and In Combination with Veltuzumab, a Humanized Anti-CD20 MAb", Blood (ASH Annual Meeting Abstracts) 2010 116: Abstract 3941.
Gondo et al., "HLA class II antigen associated invariant chain gene expression in malignant lymphoma", Br. J. Haematol. 67(4):413-7 (1987).
Green et al., "Antigen-specific human monoclonal antibodies from mice engineered with human Ig heavy and light chain YACs", Nature Genetics 7:13-21 (1994).
Gussow et al., "Humanization of monoclonal antibodies", Methods Enzymol. 1991;203:99-121.
Hansen et al., "Internalization and catabolism of radiolabelled antibodies to the MHC class-ll invariant chain by B-cell lymphomas", Biochem. J. 1996, 320:293-300.
Hashida et al., "More useful maleimide compounds for the conjugation of Fab' to horseradish peroxidase through thiol groups in the hinge", J Appl Biochem. Feb.-Apr. 1984;6(1-2):56-63.
Hekman et al., "Initial experience with treatment of human B cell lymphoma with anti-CD19 monoclonal antibody", Dancer Immunol. Immunother. 1991;32(6):364-72.
Hess et al., "Specificity of effector T lymphocytes in autologous graft-versus-host disease: role of the major histocompatibility complex class II invariant chain peptide", Blood 89(6):2203-9 (1997).
Hildebrandt et al., "Expression of CD 21, CD 22, and the mouse erythrocyte receptor on peripheral B lymphocytes in rheumatoid arthritis", Ann Rheum Dis. Jul. 1988;47(7):588-94.
Imuran patient information leaflet, GlaxoSmithKline 7076598/5093, Oct. 2004.
Inaoki et al., "CD19-regulated signaling thresholds control peripheral tolerance and autoantibody production in B lymphocytes", J Exp Med. Dec. 1, 1997;186(11):1923-31.
Jones et al., "Replacing the complementarity-determining regions in a human antibody with those from a mouse" Nature 321(6069):522-5 (1986).
Juweid et al., "99Tcm-LL1: a potential new bone marrow imaging agent", Nucl. Med. Commun. 18(2):142-8 (1997).
Juweid et al., "Treatment of non-Hodgkin's lymphoma with radiolabeled murine, chimeric, or humanized LL2, an anti-CD22 monoclonal antibody", Cancer Res 55(23 Suppl):5899s-5907s (1995).
Kaminski et al., "Radioimmunotherapy of B-cell lymphoma with [131I]anti-B1 (anti-CD20) antibody", N. Engl. J. Med. 329(7):459-65 (1993).
Kiener et al., "Stimulation of CD40 with purified soluble gp39 induces proinflammatory responses in human monocytes", J Immunol. Nov. 15, 1995;155(10):4917-25.
Kiesel et al., "Removal of cells from a malignant B-cell line from bone marrow with immunomagnetic beads and with complement and immunoglobulin switch variant mediated cytolysis", Leuk. Res. 11(12):1119-25 (1987).
Kohler et al., "Continuous cultures of fused cells secreting antibody of predefined specificity", Nature 256:495-7(1975).
Kreitman et al., "Pseudomonas exotoxin-based immunotoxins containing the antibody LL2 or LL2-Fab' induce regression of subcutaneous human B-cell lymphoma in mice", Cancer Res. 53(4):819-25 (1993).
Leonard et al., "Epratuzumab, a new Anti-CD22, humanized, monoclonal antibody for the therapy of non-Hodgkin's lymphoma (NHL): phase I/II trial results", Blood 94:92a-93a, Abstract # 404, (1999).
Leung et al., "Chimerization and humanization of a B-cell Lymphoma specific antibody, LL2", Proc Am Assoc Cancer Res 1993; 34:481, Abstr #2872.
Leung et al., "Chimerization of LL2, a Rapidly Internalizing Antibody Specific for B Cell Lymphoma", Hybridoma 13(6):469-476 (1994).
Leung et al., "Construction and characterization of a humanized, internalizing, b-cell (CD22)-specific, leukemia/lymphma antibody, LL2", Mol. Immunol. 32(17/18):1413-1427 (1995).
Levine et al., "IgM antibody-related polyneuropathies: B-cell depletion chemotherapy using Rituximab", Neurology 52(8):1701-4 (1999).
Li et al., "The epitope specificity and tissue reactivity of four murine monoclonal anti-CD22 antibodies", Cell Immunol. 118(1):85-99 (1989).
Lonberg et al., "Antigen-specific human antibodies from mice comprising four distinct genetic modifications", Nature 368:856-9 (1994).
Longo, D. L., "Immunotherapy for non-Hodgkin's lymphoma", Curr. Opin. Oncol. 8(5):353-9 (1996).
Losman et al., "Baboon anti-idiotype antibodies mimic a carcinoembryonic antigen epitope", Int J Cancer. Aug. 15, 1990;46(2):310-4.
Lundberg, B., "Preparation of drug-carrier emulsions stabilized with phosphatidylcholine-surfactant mixtures", J. Pharm. Sci. 83(1):72-5 (1994).
Lundberg et al., "Submicron lipid emulsions containing amphipathic polyethylene glycol for use as drug-carriers with prolonged circulation time", Int. J. Pharm. 134:119-127 (1996).
ADC Could Benefit Some with Breast Cancer, Cancer Discov. May 2019;9(5):570.
An ADC for Triple-Negative Breast Cancer, Cancer Discov. Jan. 2016;6(1):OF8.
Bardia et al., "Sacituzumab Govitecan-hziy in Triple-Negative Breast Cancer. Reply", N Engl J Med. Jun. 13, 2019;380(24):2382.
Bardia et al., "Sacituzumab Govitecan-hziy in Refractory Metastatic Triple-Negative Breast Cancer", N Engl J Med. Feb. 21, 2019;380(8):741-751.
Burki, TK., "Sacituzumab govitecan activity in advanced breast cancer", Lancet Oncol. May 2017;18(5):e246.
Cardillo et al., "IMMU-140, a Novel SN-38 Antibody-Drug Conjugate Targeting HLA-DR, Mediates Dual Cytotoxic Effects in Hematologic Cancers and Malignant Melanoma", Mol Cancer Ther. Jan. 2018;17(1):150-160.
Cardillo et al., "Sacituzumab Govitecan (IMMU-132), an Anti-Trop-2/SN-38 Antibody-Drug Conjugate: Characterization and Efficacy in Pancreatic, Gastric, and Other Cancers", Bioconjug Chem. May 20, 2015;26(5):919-31.
Chang et al., "Combining ABCG2 Inhibitors with IMMU-132, an Anti-Trop-2 Antibody Conjugate of SN-38, Overcomes Resistance to SN-38 in Breast and Gastric Cancers", Mol Cancer Ther. Aug. 2016;15(8):1910-9.
Dong et al., "Antibody-drug conjugates of 7-ethyl-10-hydroxycamptothecin: Sacituzumab govitecan and labetuzumab govitecan", Eur J Med Chem. Apr. 1, 2019;167:583-593.
Dotan et al., "Phase I/II Trial of Labetuzumab Govitecan (Anti-CEACAM5/SN-38 Antibody-Drug Conjugate) in Patients With Refractory or Relapsing Metastatic Colorectal Cancer", J Clin Oncol. Oct. 10, 2017;35(29):3338-3346.
Goldenberg et al., "The emergence of trophoblast cell-surface antigen 2 (TROP-2) as a novel cancer target", Oncotarget. Jun. 22, 2018;9(48):28989-29006.
Goldenberg et al., "Antibody-drug conjugates targeting TROP-2 and incorporating SN-38: A case study of anti-TROP-2 sacituzumab govitecan", MAbs. Jul. 18, 2019:1-9.
Goldenberg et al., "Trop-2 is a novel target for solid cancer therapy with sacituzumab govitecan (IMMU-132), an antibody-drug conjugate (ADC)", Oncotarget. Sep. 8, 2015;6(26):22496-512.

(56) References Cited

OTHER PUBLICATIONS

Gray et al., "Therapy of Small Cell Lung Cancer (SCLC) with a Topoisomerase-I-inhibiting Antibody-Drug Conjugate (ADC) Targeting Trop-2, Sacituzumab Govitecan", Clin Cancer Res. Oct. 1, 2017;23(19):5711-5719.
Han et al., "Sacituzumab Govitecan (IMMU-132) in treatment-resistant uterine serous carcinoma: A case report", Gynecol Oncol Rep. May 23, 2018;25:37-40.
Heist et al., "Therapy of Advanced Non-Small-Cell Lung Cancer With an SN-38-Anti-Trop-2 Drug Conjugate, Sacituzumab Govitecan", J Clin Oncol Aug. 20, 2017;35(24):2790-2797.
Kaplon et al., "Antibodies to watch in 2019", MAbs. Feb./Mar. 2019;11(2):219-238.
Kaplon et al., "Antibodies to watch in 2018", MAbs. Feb./Mar. 2018;10(2):183-203.
Lu et al., "Advances in antibody therapeutics targeting small-cell lung cancer", Adv Clin Exp Med. Sep. 2018;27(9):1317-1323.
Nagayama et al., "Antibody-Drug Conjugates for the Treatment of Solid Tumors: Clinical Experience and Latest Developments", Target Oncol. Dec. 2017;12(6):719-739.
Ocean et al., "Sacituzumab govitecan (IMMU-132), an anti-Trop-2-SN-38 antibody-drug conjugate for the treatment of diverse epithelial cancers: Safety and pharmacokinetics", Cancer. Oct. 1, 2017;123(19):3843-3854.
Ozaki et al., "Sacituzumab Govitecan-hziy in Triple-Negative Breast Cancer", N Engl J Med. Jun. 13, 2019;380(24):2382.
Ponde et al., "Antibody-Drug Conjugates in Breast Cancer: a Comprehensive Review", Curr Treat Options Oncol. Apr. 1, 2019;20(5):37.
Sahota et al., "Sacituzumab govitecan: an antibody-drug conjugate", Expert Opin Biol Ther. Aug. 2017;17(8): 1027-1031.
Sharkey et al., Selective and Concentrated Accretion of SN-38 with a CEACAM5-Targeting Antibody-Drug Conjugate (ADC), Labetuzumab Govitecan (IMMU-130), Mol Cancer Ther. Jan. 2018;17(1):196-203.
Sharkey et al., "Enhanced Delivery of SN-38 to Human Tumor Xenografts with an Anti-Trop-2-SN-38 Antibody Conjugate (Sacituzumab Govitecan)", Clin Cancer Res. Nov. 15, 2015;21(22):5131-8.
Starodub et al., "First-in-Human Trial of a Novel Anti-Trop-2 Antibody-SN-38 Conjugate, Sacituzumab Govitecan, for the Treatment of Diverse Metastatic Solid Tumors", Clin Cancer Res. Sep. 1, 2015;21(17):3870-8.
Stirrups, R., "Sacituzumab govitecan-hziy for triple-negative breast cancer", Lancet Oncol. Apr. 2019;20(4):e194.
Tray et al., "Antibody-drug conjugates in triple negative breast cancer", Future Oncol. Oct. 2018; 14(25):2651-2661.
Vlachostergios et al., "Antibody-Drug Conjugates in Bladder Cancer", Bladder Cancer. Jul. 30, 2018;4(3):247-259.
Vranic et al., "Potential Novel Therapy Targets in Neuroendocrine Carcinomas of the Breast", Clin Breast Cancer: Apr. 2019;19(2):131-136.
Zangardi et al., "Sacituzumab for the treatment of triple-negative breast cancer: the poster child of future therapy?", Expert Opin Investig Drugs. Feb. 2019;28(2):107-112.
Beckman et al., "Antibody constructs in cancer therapy: protein engineering strategies to improve exposure in solid tumors", Cancer. Jan. 15, 2007;109(2):170-9.
Berenbaum, MC., "Synergy, additivism and antagonism in immunosuppression. A critical review", Clin Exp Immunol. Apr. 1977;28(1):1-18.
Berenbaum, MC., "What is synergy?", Pharmacol Rev. Jun. 1989;41(2):93-141.
Cespedes et al., "Mouse models in oncogenesis and cancer therapy", Clin Transl Oncol. May 2006;8(5):318-29.
Dennis, C., "Cancer: off by a whisker", Nature. Aug. 17, 2006,442(7104):739-41.
Foran, JM., "Antibody-based therapy of non-Hodgkin's lymphoma", Best Pract Res Clin Haematol. Sep. 2002;15(3):449-65.

Fujimori et al., "A modeling analysis of monoclonal antibody percolation through tumors: a binding-site barrier", J Nucl Med. Jul. 1990;31(7):1191-8.
Lundberg et al., "Conjugation of an anti-B-cell lymphoma monoclonal antibody, LL2, to long-circulating drug-carrier lipid emulsions", J. Pharm. Pharmacol. 51(10):1099-105 (1999).
Mack et al., "A small bispecific antibody construct expressed as a functional single-chain molecule with high tumor cell cytotoxicity", Proc. Natl. Acad. Sci. USA 92:7021-7025 (1995).
Maloney et al., "Phase I clinical trial using escalating single-dose infusion of chimeric anti-CD20 monoclonal antibody (IDEC-C2B8) in patients with recurrent B-cell lymphoma", Blood 84(8):2457-66 (1994).
Maloney et al., "IDEC-C2B8 (Rituximab) anti-CD20 monoclonal antibody therapy in patients with relapsed low-grade non-Hodgkin's lymphoma", Blood. Sep. 15, 1997;90(6):2188-95.
Mason et al., "Value of monoclonal anti-CD22 (p135) antibodies for the detection of normal and neoplastic B lymphoid cells", Blood. Mar. 1987;69(3):836-40.
Mills et al., "Diagnostic imaging of non-Hodgkin's lymphoma with anti-lymphomas antibody labeled with Tc-99m", Proc Am Assoc Cancer Res 1993; 34:479, Abstract #2857.
Mole S. E., "Epitope Mapping", Methods in Molecular Biology, vol. 10: Immunochemical Protocols, Manson (Ed.), Humana Press, Inc. (1992).
Morrison et al., "Chimeric human antibody molecules: mouse antigen-binding domains with human constant region domains", Proc Natl Acad Sci USA Nov. 1984;81(21):6851-5.
Murthy et al., "Lymphoma imaging with a new technetium-99m labelled antibody, LL2", Eur J Nucl Med. 1992;19(6):394-401.
Ochakovskaya et al., Therapy of Disseminated B-Cell Lymphoma Xenografts in Severe Combined Immunodeficient Mice with an Anti-CD74 Antibody Conjugated with (111)Indium, (67)Gallium, or (90)Yttrium, Clin. Dancer Res. 7(6):1505-1510 (2001).
Orlandi et al., "Cloning immunoglobulin variable domains for expression by the polymerase chain reaction", Proc. Natl. Acad. Sci. USA 86:3833-3837 (1989).
Pastan et al., "Immunotoxins", Cell 47:641-648 (1986).
Pawlak-Byczkowska et al., "Two new monoclonal antibodies, EPB-1 and EPB-2, reactive with human lymphoma", Cancer Res. 49(16):4568-77 (1989).
Perrota et al., "Response of chronic relapsing ITP of 10 years duration to Rituximab", Blood, vol. 92(10 Suppl.), p. 88b, 1998, Abstract# 3360.
Press et al., "Radiolabeled-antibody therapy of B-cell lymphoma with autologous bone marrow support", N. Engl. J. Med. 329(17):1219-24 (1993).
Press et al., "Phase II trial of 131I-B1 (anti-CD20) antibody therapy with autologous stem cell transplantation for relapsed B cell lymphomas", Lancet 346:336-40 (1995).
Press et al., "Prospects for the management of non-Hodgkin's lymphomas with monoclonal antibodies and immunoconjugates". Cancer J. Sci. Am. 4(Suppl 2):S19-26 (1998).
Protheroe et al., "Remission of inflammatory arthropathy in association with anti-CD20 therapy for non-Hodgkin's lymphoma", Rheumatology (Oxford) 38(11):1150-2 (1999).
Qu et al., "Carbohydrates engineered at antibody constant domains can be used for site-specific conjugation of drugs and chelates", J. Immunol. Methods 213(2):131-44 (1998).
Qu et al., "Internalization and cytotoxic effects of a humanized anti-CD74 antibody, LL1", Proc Am Assoc Cancer Res 2002;43:255, Abstract # 1269.
Queen et al., "A humanized antibody that binds to the interleukin 2 receptor", Proc Natl Acad Sci U S A. Dec. 1989;86(24):10029-33.
Renner et al., "Monoclonal antibodies in the treatment of non-Hodgkin's lymphoma: recent results and future prospects". Leukemia 11(Suppl 2):S55-9 (1997).
Riechmann et al., "Reshaping human antibodies for therapy", Nature 332(6162):323-7 (1988).
Roche et al., "Cell surface HLA-DR-invariant chain complexes are targeted to endosomes by rapid internalization", Proc Natl Acad Sci U S A. Sep. 15, 1993;90(18):8581-5.

(56) References Cited

OTHER PUBLICATIONS

Rowan et al., "Cross-linking of the CAMPATH-1 antigen (CD52) mediates growth inhibition in human B- and T-lymphoma cell lines, and subsequent emergence of CD52-deficient cells", Immunology 95(3):427-36 (1998).
Rudikoff et al., "Single amino acid substitution altering antigen-binding specificity", Proc. Natl. Acad. Sci. USA 79(6):1979-83 (1982).
Rudnick et al., "Affinity and avidity in antibody-based tumor targeting", Cancer Biother Radiopharm. Apr. 2009;24(2):155-61.
Saltzman et al., "Transport rates of proteins in porous materials with known microgeometry", Biophys. J. 55(1):163-71 (1989).
Sandhu, J. S., "Protein engineering of antibodies", Crit. Rev. Biotechnol. 12(5-6):437-62 (1992).
Schwarts-Albiez et al., "The carbohydrate moiety of the CD22 antigen can be modulated by inhibitors of the glycosylation pathway", Leukocyte Typing IV. White Cell Differentiation Antigens, Knapp et al., (Eds.), p. 65-67, Oxford University Press, 1989.
Sherwood et al., "Controlled antibody delivery systems", Biotechnology 10(11):1446-9 (1992).
Shih et al., "Internalization and intracellular processing of an anti-B-cell lymphoma monoclonal antibody, LL2", Int J Dancer 56(4):538-45 (1994).
Singer et al., "Optimal humanization of 1B4, an anti-CD18 murine monoclonal antibody, is achieved by correct choice of human V-region framework sequences", J. Immunol. 150(7):2844-57 (1993).
Stein et al., "Epitope specificity of the anti-(B cell lymphoma) monoclonal antibody, LL2", Cancer Immunol. Immunother. 37(5):293-8 (1993).
Tallarida, RJ., Drug Synergism and Dose Effect Analysis, Ed. Chapman & Hall, 2000, pp. 1-8; 10-13; 57-71.
Taylor et al., "Human immunoglobulin transgenes undergo rearrangement, somatic mutation and class switching in mice that lack endogenous IgM", Int Immunol. Apr. 1994;6(4):579-91.
Theocharis et al., "Characterization of in vivo mutated T cell clones from patients with systemic lupus erythematosus", Clin. Immunol. Immunopathol. 74(2):135-42 (1995).
Tsang et al.,"Reactive oxygen species mediate doxorubicin induced p53-independent apoptosis", Life Sci. Sep. 5, 2003;73(16):2047-58.
Vuist et al., "Potentiation by interleukin 2 of Burkitt's lymphoma therapy with anti-pan B (anti-CD19) monoclonal antibodies in a mouse xenotransplantation model". Cancer Res. 49(14):3783-8 (1989).
Wilson et al., "cDNA cloning of the B cell membrane protein CD22: a mediator of B-B cell interactions", J Exp Med. Jan. 1, 1991;173(1):137-46.
Wilson et al., "Genomic structure and chromosomal mapping of the human CD22 gene", J Immunol. Jun. 1, 1993;150(11):5013-24.
Wosnik et al., "Rapid construction of large synthetic genes: total chemical synthesis of two different versions of the bovine prochymosin gene", Gene. 1987;60(1):115-27.
Wurflein et al., "Evaluating antibodies fortheir capacity to induce cell-mediated lysis of malignant B cells", Cancer Res. Jul. 15, 1998;58(14):3051-8.
Anbalagan et al., "Peptidomimetic Src/pretubulin inhibitor KX-01 alone and in combination with paclitaxel suppresses growth, metastasis in human ER/PR/HER2-negative tumor xenografts", Mol Cancer Ther. Sep. 2012;11(9):1936-47.
Bennouna et al., "Therapeutic strategies for colorectal cancer in Europe and the United States: focus on chemotherapy for advanced colorectal cancer" Int. J. Clin. Oncol. (2002) 7:236-244.
Burkard et al., "Validating cancer drug targets through chemical genetics", Biochim Biophys Acta. Dec. 2010;1806(2):251-7.
Burke et al., "Design, synthesis, and biological evaluation of antibody-drug conjugates comprised of potent camptothecin analogues", Bioconjug Chem. Jun. 2009;20(6):1242-50.
Burnham et al., "Invasion of HeLa cells by group B *Streptococcus* requires the phosphoinositide-3-kinase signalling pathway and modulates phosphorylation of host-cell Akt and glycogen synthase kinase-3", Microbiology. Dec. 2007;153(Pt 12):4240-52.

Cao et al., "Bispecific Antibodies as Novel Bioconjugates" Bioconj. Chem. Nov.-Dec. 1998;9(6):635-44.
Cardillo et al., "Humanized anti-Trop-2 IgG-SN-38 conjugate for effective treatment of diverse epithelial cancers: preclinical studies in human cancer xenograft models and monkeys", Clin Cancer Res May 15, 2011;17(10):3157-69.
Carter et al., Chemotherapy of Cancer; 2nd Edition; John Wiley & Sons, New York, 1981; Appendix C.
Chari et al., "Immunoconjugates Containing Novel Maytansinoids: Promising Anticancer Drugs" Cancer Res. Jan. 1, 1992;52(1):127-31.
Feldmann et al., "Design of effective immunotherapy for human autoimmunity", Nature. Jun. 2, 2005;435(7042):612-9.
Fukuda et al., "Evaluation of novel platinum complexes, inhibitors of topoisomerase I and II in non-small cell lung Dancer (NSCLC) sublines resistant to cisplatin", Anticancer Res. Mar.-Apr. 1995;15(2):393-8.
Garcia-Giron et al., "Phase II trial of fortnightly irinotecan (CPT-11) in the treatment of colorectal cancer patients resistant to previous fluoropyrimidine-based chemotherapy", Clin Transl Oncol Jul. 2005;7(6):244-9.
Gomez-Manzano et al., "Delta-24 increases the expression and activity of topoisomerase I and enhances the antiglioma effect of irinotecan", Clin Cancer Res. Jan. 15, 2006;12(2):556-62.
Govindan et al., "Milatuzumab-SN-38 conjugates for the treatment of CD74+ cancers", Mol Cancer Ther. Jun. 2013;12(6):968-78.
Gueritte-Voegelein et al., "Relationships between the Structure of Taxol Analogues and Their Antimitotic Activity" J. Med. Chem. 1991, 34, 992-998.
Guillemard et al., "Taxane-Antibody Conjugates Afford Potent Cytotoxicity, Enhanced Solubility, and Tumor Target Selectivity" Cancer Res. 61, 694-699, Jan. 15, 2001.
Gura, T., "Systems for identifying new drugs are often faulty", Science. Nov. 7, 1997;278(5340):1041-2.
Hatzakis et al., "Synthesis and single enzyme activity of a clicked lipase-BSA hetero-dimer" Chem. Commun., 2006, 2012-2014.
He et al., "Synthesis and biological evaluation of bis and monocarbonate prodrugs of 10-hydroxycamptothecins", Bioorg Med Chem. Aug. 1, 2004;12(15):4003-8.
Heindel et al., "A Novel Heterobifunctional Linker for Formyl to Thiol Coupling" Bioconjugate Chem. 1991, 2, 427-430.
Horwitz et al., "Antiviral action of camptothecin", Antimicrob Agents Chemother. Nov. 1972;2(5):395-401.
Huang et al., "The Rana catesbeiana rcr Gene Encoding a Cytotoxic Ribonuclease" J. Biol. Chem. 273 (11):6395-6401 (1998).
Kaiser, J., "Cancer. First pass at cancer genome reveals complex landscape", Science. Sep. 8, 2006;313(5792):1370.
King et al., "Monoclonal Antibody Conjugates of Doxorubicin Prepared with Branched Linkers: A Novel Method for Increasing the Potency of Doxorubicin Immunoconjugates" Bioconjugate Chem. 1999, 10, 279-288.
Kreitman et al., "Pseudomonas Exotoxin-based Immunotoxins Containing the Antibody LL2 or LL2-Fab' Induce Regression of Subcutaneous Human B-Cell Lymphoma in Mice" Cancer Res 53, 819-825, Feb. 15, 1993.
Krontiris and Capizzi, Internal Medicine, Chapters 71-72, pp. 699-729; 4th Edition, Jay Stein (Ed.), Elsevier Science, 1994.
Kufe et al., Non-Intercalating Topoisomerase-Targeting Drugs, Holland-Frei Cancer Medicine, Hamilton (ON), BC Decker (2003).
Kufe et al., Topoisomerase Biology, 6th Ed., Holland-Frei Cancer Medicine, Hamilton (ON), BC Decker (2003).
Mahato et al., "Prodrugs for improving tumor targetability and efficiency", Adv Drug Deliv Rev. Jul. 18, 2011;63(8):659-70.
Matsumura, Y., Preclinical and clinical studies of NK012, an SN-38-incorporating polymeric micelles, which is designed based on EPR effect, Adv Drug Deliv Rev. Mar. 18, 2011;63(3):184-92.
Miller et al., "Development of Taxoids with Enhanced Toxicity and Solubility" Poster Presentation, 224th ACS Nat. Meeting, Aug. 18-22, 2002, Boston, MA.
Mine Safety and Health Administration (Special Hazards of Acetylene, Sep. 16, 2011).

(56) References Cited

OTHER PUBLICATIONS

Moon et al., "Antibody Conjugates of 7-Ethyl-10-hydroxycamptothecin (SN-38) for Targeted Cancer Chemotherapy" J. Med. Chem. 2008, 51, 6916-6926.

Newton et al., "Potent and specific antitumor effects of an anti-CD22-targeted cytotoxic ribonuclease: potential for the treatment of non-Hodgkin lymphoma" Blood, 97(2):528-35 (2001).

Paul, W., ed., Fundamental Immunology, 3rd Ed., Raven Press, New York, 1993, p. 292-295.

Perez et al., "Inhibition by the anti-mitotic drug doxorubicin of platelet-activating-factor-induced late eosinophil accumulation in rats" Eur J. Pharmacol. Sep. 4, 1998;356(2-3):239-43.

Reddy et al., "Elimination of Fc Receptor-Dependent Effector Functions of a Modified IgG4 Monoclonal Antibody to Human CD4", J. Immunol. 164:1925-1933 (2000).

Rowlinson-Busza et al., "Targeted delivery of biologic and other antineoplastic agents" Curr. Opin. Oncol. Dec. 1992;4(6):1142-1148.

Sharkey et al., "Epratuzumab-SN-38: a new antibody-drug conjugate for the therapy of hematologic malignancies", Mol Cancer Ther. Jan. 2012; 11(1):224-34.

Sharkey et al., "Combination radioimmunotherapy and chemoimmunotherapy involving different or the same targets improves therapy of human pancreatic carcinoma xenograft models", Mol Cancer Ther. Jun. 2011;10(6):1072-81.

Shih et al., "The Processing and Fate of Antibodies and Their Radiolabels Bound to the Surface of Tumor Cells In Vitro: A Comparison of Nine Radiolabels" J. Nucl. Med. 1994; 35:899-908.

Shih et al., "In vitro and in vivo reactivity of an internalizing antibody, RS7, with human breast cancer", Cancer Res. Dec. 1, 1995;55(23 Suppl):5857s-5863s.

Stanford University Environmental Health and Safety (Information on Azide Compounds, Dec. 2, 2008).

Suzawa et al., "Synthesis of a Novel Duocarmycin Derivative DU-257 and its Application to Immunoconjugate Using Poly(ethylene glycol)-dipeptidyl Linker Capable of Tumor Specific Activation" Bioorg. Med. Chem. 8(8):2175-84 (2000).

Suzawa et al., "Enhanced tumor cell selectivity of adriamycin-monoclonal antibody conjugate via a poly(ethylene glycol)-based cleavable linker" J. Control. Release 79:229-242 (2002).

Trail et al., "Carcinoma Reactive Doxorubicin (DOX) Conjugates: Comparison of BR64-DOX Conjugates Prepared With Disulfide or Thioether Linkers", Proc. Amer. Assoc. Cancer Res., vol. 34, Mar. 1993, #2858, p. 479.

Talmadge et al., "Murine models to evaluate novel and conventional therapeutic strategies for cancer", Am J Pathol. Mar. 2007;170(3):793-804.

Thurber et al., "Antibody tumor penetration: transport opposed by systemic and antigen-mediated clearance", Adv Drug Deliv Rev. Sep. 2008;60(12):1421-34.

Van Noort and Amor, "Cell Biology of Autoimmune Disease", vol. 178, pp. 127-206; International Rev. of Cytology, 1998.

Walker et al., "Synthesis of an Immunoconjugate of Camptothecin" Bioorg. Med. Chem. Lett. 12(2):217-219 (2002).

\* cited by examiner

FIG. 2

Combination index values for IMMU-132 plus olaparib, rucaparib, or talazoparib in TNBC cell lines.

| Cell Line | Single Agent IC₅₀-values (mean ± S.D.) | | | | C.I.-values | | | | | | | | | |
|---|---|---|---|---|---|---|---|---|---|---|---|---|---|---|
| | IMMU-132 (nM) | Olaparib (µM) | Rucaparib (µM) | Talazoparib (nM) | Olaparib + IMMU-132 | | | Rucaparib + IMMU-132 | | | Talazoparib + IMMU-132 | | |
| | | | | | IC₁₀ | IC₂₀ | IC₃₀ | IC₁₀ | IC₂₀ | IC₃₀ | IC₁₀ | IC₂₀ | IC₃₀ |
| HCC1806 | 1.9 ± 0.4 | 7.3 ± 1.4 | 5.4 ± 0.3 | 4.7 ± 1.0 | 0.81 | 0.59 | 0.29 | 1.09 | 0.80 | 0.46 | 1.21 | 0.80 | 0.50 |
| HCC38 | 3.4 ± 0.5 | 28.5 ± 18.7 | 16.9 ± 0.7 | 104.9 ± 44.7 | 0.46 | 0.25 | 0.16 | 1.07 | 0.91 | 0.47 | 0.49 | 0.20 | 0.11 |
| MDA-MB-468 | 3.5 ± 0.4 | 9.8 ± 1.0 | 10.3 ± 0.8 | 322.3 ± 27.7 | 0.87 | 0.49 | 0.22 | 1.01 | 0.63 | 0.34 | 0.37 | 0.15 | 0.07 |
| MDA-MB-231 | 7.5 ± 1.2 | 21.7 ± 6.0 | 7.1 ± 1.0 | 36.3 ± 8.0 | 0.89 | 0.42 | 0.28 | 0.69 | 0.40 | 0.22 | 0.40 | 0.17 | 0.08 |

C.I.-values = Combination Index values determined as described in *Methods*.

IC₁₀, IC₂₀, and IC₃₀ = CI values determined when IMMU-132 or PARPi used at concentrations calculated to cause 10%, 20%, and 30% growth inhibition when used alone, respectively.

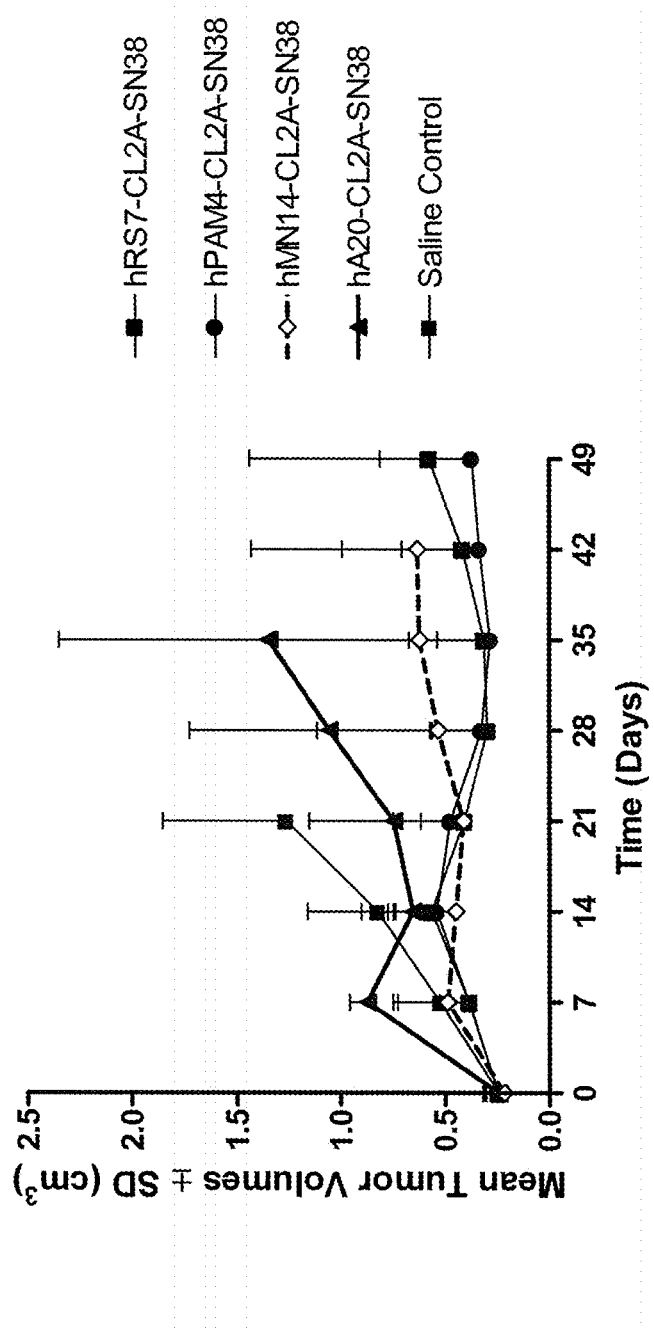

SYNERGISTIC EFFECT OF ANTI-TROP-2 ANTIBODY-DRUG CONJUGATE IN COMBINATION THERAPY FOR TRIPLE-NEGATIVE BREAST CANCER WHEN USED WITH MICROTUBULE INHIBITORS OR PARP INHIBITORS

RELATED APPLICATIONS

This application is a divisional of U.S. patent application Ser. No. 15/481,090, filed Apr. 6, 2017, which was a continuation-in-part of U.S. patent application Ser. No. 15/190,805 (now issued U.S. Pat. No. 9,707,302), filed Jun. 23, 2016, which claimed the benefit under 35 U.S.C. 119(e) of U.S. Provisional Patent Application 62/184,331, filed Jun. 25, 2015, 62/201,361, filed Aug. 5, 2015, 62/250,715, filed Nov. 4, 2015, and 62/263,134, filed Dec. 4, 2015. This application claims the benefit under 35 U.S.C. 119(e) of U.S. Provisional Patent Applications 62/322,429, filed Apr. 14, 2016, and 62/384,423, filed Sep. 7, 2016. The entire text of each priority application is incorporated herein by reference.

SEQUENCE LISTING

The instant application contains a Sequence Listing which has been submitted in ASCII format via EFS-Web and is hereby incorporated by reference in its entirety. Said ASCII copy, created on Mar. 27, 2017, is named IMM368US1_SL.txt and is 7,951 bytes in size.

BACKGROUND OF THE INVENTION

Field of the Invention

The present invention relates to combination therapy with anti-Trop-2 antibody-drug conjugates (ADCs) and one or more microtubule inhibitors and/or PARP (poly ADP ribose polymerase) inhibitors, for treating triple-negative breast cancer (TNBC). Surprisingly, the combination therapy shows synergistic effects, compared to the individual agents alone, in human TNBC patients. The combination therapy is an example of the concept of synthetic lethality, in which targeted inhibition of two separate, but complementary intracellular pathways may be significantly more effective than inhibiting either alone. In preferred embodiments, the drug conjugated to the antibody moiety may be one that induces DNA strand breaks, such as auristatins, colicheamicins, camptothecins (e.g., SN-38) or a prodrug form of 2-pyrrolinodoxorubicine (P2PDox). Exemplary drugs inducing DNA strand breaks include, but are not limited to, SN-38, P2PDox, topotecan, doxorubicin, etoposide, cisplatinum, oxaliplatin, or carboplatin. Most preferably, the ADC comprises SN-38 linked to the hRS7 anti-Trop-2 antibody (sacituzumab govitecan or IMMU-132). The PARP and/or microtubule inhibitors may be administered separately or together with the ADC. Preferably, ADCs are administered at specific dosages and/or specific schedules of administration that optimize their therapeutic effect. The optimized dosages and schedules of administration of antibody-drug conjugates (ADCs) for human therapeutic use disclosed herein show unexpected superior efficacy that could not have been predicted from animal model studies, allowing effective treatment of cancers that are resistant to standard anti-cancer therapies, including irinotecan (CPT-11), paclitaxel or other compounds that induce DNA strand breaks. The methods are of use in treating such diseases as triple-negative breast cancer (TNBC), metastatic colorectal cancer, urothelial cancer, SCLC or NSCLC, as well as other Trop-2-expressing cancers. Most preferably, the cancer is TNBC.

Background of the Invention

Synthetic lethality is a concept wherein the simultaneous loss of function of two different genes results in cell death, whereas loss of just one gene is still compatible with cellular viability (Kaelin, Nat Rev Cancer 2005, 5:689-98). This concept has been applied to cancer therapy in which a cell carrying a genetic mutation is targeted with a chemotherapeutic that blocks the function of another gene used by the cell to overcome this first mutation. In this context, the drug will be more potent in cells carrying the mutation than it would be in others that are genetically intact.

One class of defects susceptible to synthetic lethality is those that affect homologous recombination repair (HRR) of double-stranded DNA (dsDNA) breaks. BRCA1 and BRCA2 are two such genes involved in HRR, and mutational loss of BRCA1/2 makes a cell more susceptible to drugs that block other DNA repair mechanisms (McLornan et al., N Engl J Med 2014, 371:1725-35). Another protein involved in maintaining the integrity of DNA is poly(ADP-ribose) polymerase (PARP) (Satoh & Linhahl, Nature 1992, 356:356-58). PARP is a family of enzymes whose primary function is to repair single-stranded DNA breaks before they advance to double-stranded breaks. PARP inhibitors (PARPi) have been developed to treat multiple cancer types with BRCA1/2 mutations, thereby creating synthetic lethality in the BRCA1/2-defective cells (Benafif & Hall, Onco Targets Ther 2015; 8:519-28).

Clinically, therapy with PARPi has resulted in sustained anti-tumor responses in ovarian (Fong et al., N Engl J Med 2009, 361:123-34; Fong et al., J Clin Oncol 2010, 28:2512-19; Gelmon et al., Lancet Oncol 2011, 12:852-61; Marulonis et al., Cancer 2016, 122:1844-52), prostate (Fong et al., N Engl J Med 2009, 361:123-34), pancreatic (Lowery et al., Oncologist 2011, 16:1397-402), and triple-negative breast cancers (TNBC) (Gelmon et al., Lancet Oncol 2011, 12:852-61; Tutt et al., Lancet 2010, 376:235-44). In patients with TNBC, approximately 25% carry germline mutations of BRCA1/2 (Lips et al., Br J Cancer 2013, 108:2172-77).

In one clinical trial, TNBC patients with germline BRCA1/2 mutations were treated with the PARPi, olaparib. While this therapy demonstrated a higher disease stabilization rate in BRCA1/2-mutant compared to non-mutant patients, there were no sustained responses achieved in either cohort (Gelmon et al., Lancet Oncol 2011, 12:852-61). This is in contrast to Tutt et al. (Lancet 2010, 376:235-44), in which 60% of TNBC patients with germline BRCA1/2 mutations had a partial response and 35% stable disease. This discrepancy is thought to be due, in part, to the large heterogeneity of TNBC and BRCA mutations.

Efforts to improve the effect of PARPi focus mainly on stressing DNA repair pathways by increasing dsDNA breaks with such agents as ionizing radiation or platinum-based therapeutics, while these repair pathways are being blocked with PARPi (Albert et al., Clin Cancer Res 2007, 13:3033-42; Evers et al., Clin Cancer Res 2008, 14:3916-25). In addition to agents that directly interact with DNA to cause breaks, agents that inhibit topoisomerase I (Topo I), including irinotecan, have been shown to synergize with PARPi to deter the growth of a range of human tumor cell lines, including those of lung, ovarian, colon, and breast cancers (Delaney et al., Clin Cancer Res 2000, 6:2860-7; Zhang et al., Nucleic Acids Res 2011, 39:3607-20). These efforts demonstrate that by combining a DNA-damaging agent with a HRR synthetic lethality-based therapy, improved anti-tumor effects can be achieved compared to each single modality.

Sacituzumab govitecan (IMMU-132) is an antibody drug-conjugate composed of the active metabolite of irinotecan, SN-38, conjugated to an anti-Trop-2 antibody (drug:Ab ratio=7.6) (Goldenberg et al., *Oncotarget* 2015, 6:22496-512). Preclinically, IMMU-132 has significant efficacy across a broad range of Trop-2-positive human cancer xenograft models, including non-small-cell lung cancer (NSCLC), pancreatic, colon, gastric cancers, and TNBC (Goldenberg et al., *Oncotarget* 2015, 6:22496-512; Cardillo et al., *Bioconjug Chem* 2015, 26: 919-31; Cardillo et al., *Clin Cancer Res* 2011, 17:3157-69). In both gastric and TNBC tumor cells, IMMU-132 specifically mediated dsDNA breaks in Trop-2-expressing cells (Goldenberg et al., *Oncotarget* 2015, 6:22496-512; Cardillo et al., *Bioconjug Chem* 2015, 26:919-31). In a current clinical trial (ClinicalTrials.gov, NCT01631552), IMMU-132 has achieved objective responses against a range of solid tumors, including small-cell lung carcinoma (Starodub et al., *American Society of Clinical Oncology (ASCO) Annual Meeting*, Chicago, Ill., Jun. 3-6, 2016, Abstract no. 8559), NSCLC (Camidge et al., *American Society of Clinical Oncology (ASCO) Annual Meeting*, Chicago, Ill., Jun. 3-6, 2016, Abstract no. 9011), and TNBC (Bardia et al., 2015 *San Antonio Breast Cancer Symposium*, San Antonio, Tex., Dec. 8-12, 2015, Abstract no. PD3-06). In TNBC patients, with a median of 5 prior therapies, IMMU-132 treatment achieved a confirmed objective response rate of 31%. This therapy was well-tolerated over multiple cycles lasting as long as 1 year, with neutropenia being the major adverse event (Bardia et al., 2015 *San Antonio Breast Cancer Symposium*, San Antonio, Tex., Dec. 8-12, 2015, Abstract no. PD3-06).

A need exists for more effective methods of preparing and administering anti-Trop-2 ADCs, such as antibody-SN-38 conjugates, and more effective combination therapy with drugs such as microtubule inhibitors and/or PARP inhibitors.

SUMMARY OF THE INVENTION

In preferred embodiments, the invention involves combination therapy using an anti-Trop-2 ADC, in combination with a synergistic drug such as a microtubule inhibitor and/or PARP inhibitor. More preferably, the combination exhibits synergistic effects for treatment of cancer in humans, most preferably for TNBC. The anti-Trop-2 antibody is preferably conjugated to a CPT moiety, such as SN-38, or to an anthracycline, such as pro-2PDOX. Most preferably, the combination therapy is of use to treat cancers that have relapsed from or proven refractory to prior treatment with standard cancer therapies.

Preferably, the antibody moiety of the ADC is an IgG antibody or antigen-binding antibody fragment. The antibody can be of various isotypes, preferably human IgG1, IgG2, IgG3 or IgG4, more preferably comprising human IgG1 hinge and constant region sequences. The antibody or fragment thereof can be a chimeric human-mouse, a chimeric human-primate, a humanized (human framework and murine hypervariable (CDR) regions), or fully human antibody, as well as variations thereof, such as half-IgG4 antibodies (referred to as "unibodies"), as described by van der Neut Kolfschoten et al. (*Science* 2007; 317:1554-1557). More preferably, the antibody or fragment thereof may be designed or selected to comprise human constant region sequences that belong to specific allotypes, which may result in reduced immunogenicity when the antibody or ADC is administered to a human subject. Preferred allotypes for administration include a non-G1m1 allotype (nG1m1), such as G1m3, G1m3,1, G1m3,2 or G1m3,1,2. More preferably, the allotype is selected from the group consisting of the nG1m1, G1m3, nG1m1, 2 and Km3 allotypes.

As used herein, the abbreviation "CPT" may refer to camptothecin or any of its derivatives, such as SN-38, unless expressly stated otherwise. In a preferred embodiment, a drug moiety conjugated to a subject antibody is selected from camptothecin (CPT) and its analogs and derivatives and is more preferably SN-38. However, other drug moieties that may be utilized include anthracyclines (e.g., doxorubicin (DOX), epirubicin, morpholinodoxorubicin (morpholino-DOX), cyanomorpholino-doxorubicin (cyanomorpholino-DOX), 2-pyrrolinodoxorubicin (2-PDOX), and a prodrug form of 2-PDOX (pro-2-PDOX). Preferably, the antibody or fragment thereof links to at least one chemotherapeutic moiety; preferably 1 to about 5 drug moieties; more preferably 6 to 8 drug moieties, most preferably about 6 to about 12 drug moieties.

In certain preferred embodiments, an ADC, such as sacituzumab govitecan, may be used in combination therapy with at least one microtubule inhibitor. A number of microtubule inhibitors are known in the art, such as vinca alkaloids (e.g., vincristine, vinblastine), taxanes (e.g., paclitaxel), maytansinoids (e.g., mertansine) and auristatins. Other known microtubule inhibitors include demecolcine, nocodazole, epothilone, docetaxel, discodermolide, colchicine, combrestatin, podophyllotoxin, CI-980, phenylahistins, steganacins, curacins, 2-methoxy estradiol, E7010, methoxy benzenesuflonamides, vinorelbine, vinflunine, vindesine, dolastatins, spongistatin, rhizoxin, tasidotin, halichondrins, hemiasterlins, cryptophycin 52, MMAE and eribulin mesylate (see, e.g., Dumontet & Jordan, 2010, *Nat Rev Drug Discov* 9:790-803). Any such known microtubule inhibitor may be used in combination with a subject antibody-drug conjugate (ADC). Preferably, the microtubule inhibitor is one that exhibits synergistic effects when used in combination with an ADC. One potent example is SN-38-conjugated antibody, such as sacituzumab govitecan expressed by many solid cancers. Most preferably, the microtubule inhibitor is paclitaxel or eribulin mesylate.

In other preferred embodiments, the ADC may be used in combination therapy with at least one PARP inhibitor. A number of PARP inhibitors are known in the art, such as olaparib, talazoparib (BMN-673), rucaparib, veliparib, niraparib, iniparib, CEP 9722, MK 4827, BGB-290, ABT-888, AG014699, BSI-201, CEP-8983 and 3-aminobenzamide (see, e.g., Rouleau et al., 2010, *Nat Rev Cancer* 10:293-301, Bao et al., 2015, *Oncotarget* [Epub ahead of print, Sep. 22, 2015]). Any such known PARP inhibitor may be used in combination with an anti-Trop-2 ADC. Preferably, the PARP inhibitor is one that exhibits synergistic effects when used in combination with the ADC. This has been validated when using an SN-38-conjugated antibody, such as sacituzumab govitecan. Most preferably, the PARP inhibitor is olaparib, talazoparib or rucaparib.

In another alternative, the drug may be a Bruton kinase inhibitor, such as such as ibrutinib (PCI-32765), PCI-45292, CC-292 (AVL-292), ONO-4059, GDC-0834, LFM-A13 or RN486; or a PI3K inhibitor, such as idelalisib, Wortmannin, demethoxyviridin, perifosine, PX-866, IPI-145 (duvelisib), BAY 80-6946, BEZ235, RP6530, TGR1202, SF1126, INK1117, GDC-0941, BKM120, XL147, XL765, Palomid 529, GSK1059615, ZSTK474, PWT33597, IC87114, TG100-115, CAL263, PI-103, GNE477, CUDC-907, AEZS-136 or LY294002.

Various embodiments may concern use of the subject methods and compositions to treat a cancer, including but not limited to non-Hodgkin's lymphomas, B-cell acute and chronic lymphoid leukemias, Burkitt lymphoma, Hodgkin's lymphoma, acute large B-cell lymphoma, hairy cell leukemia, acute myeloid leukemia, chronic myeloid leukemia, acute lymphocytic leukemia, chronic lymphocytic leukemia, T-cell lymphomas and leukemias, multiple myeloma, Waldenstrom's macroglobulinemia, carcinomas, melanomas, sarcomas, gliomas, bone, and skin cancers. The carcinomas may include carcinomas of the oral cavity, esophagus, gastrointestinal tract, pulmonary tract, lung, stomach, colon, rectum, breast, ovary, prostate, uterus, endometrium, cervix, urinary bladder, pancreas, bone, brain, connective tissue, thyroid, liver, gall bladder, urinary bladder (urothelial), kidney, skin, central nervous system and testes.

In certain embodiments the ADC may be used in combination with surgery, radiation therapy, chemotherapy, immunotherapy with naked antibodies, including checkpoint-inhibiting antibodies, radioimmunotherapy, immunomodulators, vaccines, and the like. Most preferably, the ADC is used in combination with a PARP inhibitor and/or microtubule inhibitor. These combination therapies can allow lower doses of each therapeutic to be given in such combinations, thus reducing certain severe side effects, and potentially reducing the courses of therapy required. When there is no or minimal overlapping toxicity, full doses of each can also be given.

Preferred optimal dosing of ADCs by, for example, i.v. administration may include a dosage of between 1 mg/kg and 20 mg/kg, more preferably 4 to 16 mg/kg, most preferably 8 to 10 mg/kg, preferably given either weekly, twice weekly, every other week, or every third week. The optimal dosing schedule may include treatment cycles of two consecutive weeks of therapy followed by one, two, three or four weeks of rest, or alternating weeks of therapy and rest, or one week of therapy followed by two, three or four weeks of rest, or three weeks of therapy followed by one, two, three or four weeks of rest, or four weeks of therapy followed by one, two, three or four weeks of rest, or five weeks of therapy followed by one, two, three, four or five weeks of rest, or administration once every two weeks, once every three weeks or once a month. Treatment may be extended for any number of cycles, preferably at least 2, at least 4, at least 6, at least 8, at least 10, at least 12, at least 14, or at least 16 cycles. Exemplary dosages of use may include 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, and 18 mg/kg. However, in alternative embodiments, wherein the ADC is administered subcutaneously, preferred dosages would be in the range of 1.5 to 4.0 mg/kg. A subcutaneous dosage may be administered at a single site, or may alternatively be administered at multiple sites, each of which may receive a dosage of 1.5 to 4.0 mg/kg. In certain preferred embodiments, an initial treatment of ADC administered intravenously may be followed by a maintenance dosage administered subcutaneously.

The person of ordinary skill will realize that a variety of factors, such as age, general health, specific organ function or weight, as well as effects of prior therapy on specific organ systems (e.g., bone marrow) may be considered in selecting an optimal dosage of ADC, and that the dosage and/or frequency of administration may be increased or decreased during the course of therapy. The dosage may be repeated as needed, with evidence of tumor shrinkage observed after as few as 4 to 8 doses. The optimized dosages and schedules of administration disclosed herein show unexpected superior efficacy and reduced toxicity in human subjects, which could not have been predicted from animal model studies. Surprisingly, the superior efficacy allows treatment of tumors that were previously found to be resistant to one or more standard anti-cancer therapies, including the parental compound, CPT-11, from which SN-38 is derived in vivo.

The subject methods may include use of CT and/or PET/CT, or MRI, to measure tumor response at regular intervals. Blood levels of tumor markers, such as CEA (carcinoembryonic antigen), CA19-9, AFP, CA 15.3, or PSA, may also be monitored. Dosages and/or administration schedules may be adjusted as needed, according to the results of imaging and/or marker blood levels.

A surprising result with the instant claimed compositions and methods is the unexpected tolerability of high doses of antibody-drug conjugate when given to patients, even with repeated infusions, with only relatively low-grade toxicities of nausea and vomiting, or manageable neutropenia. Preferably, the incidence of grade 3 or higher side effects, such as anemia, diarrhea, nausea, vomiting or neutropenia, is limited to 26% or less of the treated population. More preferably, the incidence of grade 3 or higher diarrhea and neutropenia occurs in 26% or less of the treated population. A further surprising result is the lack of accumulation of the antibody-drug conjugate, unlike other products that have conjugated SN-38 to albumin, PEG or other carriers, to nontarget tissues or target tissues where the MAb is not accessible. The lack of accumulation is associated with improved tolerability and lack of serious toxicity even after repeated or increased dosing. These surprising results allow optimization of dosage and delivery schedule, with unexpectedly high efficacies and low toxicities; i.e., a higher therapeutic index than when the parental drug to SN-38, irinotecan, is given alone or in combination with other drugs. This is underscored by the black box warning on the product labeling of irinotecan, required by FDA, stating the high severe early and late diarrhea resulting from therapy with irinotecan. This is not experienced to the same extent and frequency with these SN-38-containing ADCs. Even febrile neutropenia is much lower with the SN-38-ADCs described herein than with irinotecan therapy.

The claimed methods provide for shrinkage of solid tumors, in individuals with previously resistant cancers, of 15% or more, preferably 20% or more, preferably 30% or more, more preferably 40% or more in size (as measured by summing the longest diameter of target lesions, as per RECIST or RECIST 1.1). The person of ordinary skill will realize that tumor size may be measured by a variety of different techniques, such as total tumor volume, maximal tumor size in any dimension or a combination of size measurements in several dimensions. This may be with standard radiological procedures, such as computed tomography, magnet resonance imaging, ultrasonography, and/or positron-emission tomography. The means of measuring size is less important than observing a trend of decreasing tumor size with ADC treatment, preferably resulting in elimination of the tumor. However, to comply with RECIST guidelines, CT or MRI is preferred on a serial basis, and should be repeated to confirm measurements.

While the ADC may be administered as a periodic bolus injection, in alternative embodiments the ADC may be administered by continuous infusion. In order to increase the Cmax and extend the PK of the ADC in the blood, a continuous infusion may be administered for example by indwelling catheter. Such devices are known in the art, such as HICKMAN®, BROVIAC® or PORT-A-CATH® catheters (see, e.g., Skolnik et al., *Ther Drug Monit* 32:741-48, 2010) and any such known indwelling catheter may be used. A variety of continuous infusion pumps are also known in the art and any such known infusion pump may be used. The dosage range for continuous infusion may be between 0.1 and 3.0 mg/kg per day. More preferably, these ADCs can be administered by intravenous infusions over relatively short periods of 2 to 5 hours, more preferably 2-3 hours.

In particularly preferred embodiments, the ADCs and dosing schedules may be efficacious in patients resistant to standard therapies. For example, sacituzumab govitecan (hRS7-SN-38) may be administered to a patient who has not responded to prior therapy with irinotecan, the parent agent of SN-38. Surprisingly, the irinotecan-resistant patient may show a partial or even a complete response to sacituzumab govitecan. The ability of the ADC to specifically target the tumor tissue may overcome tumor resistance by improved targeting and enhanced delivery of the therapeutic agent. A specific preferred subject may be a patient with a Trop-2-positive breast, ovarian, cervical, endometrial, lung, prostate, colon, rectum, stomach, esophageal, bladder (urothelial), renal, pancreatic, brain, thyroid, epithelial or head-and-neck cancer. Preferably, the cancer is metastatic cancer. More preferably, the patient has previously failed treatment with at least one standard anti-cancer therapy. Most preferably, the patient has previously failed therapy with irinotecan (CPT-11), the parent compound of SN-38. In alternative preferred embodiments, the cancer is TNBC, non-TNBC, endometrial, lung, or ovarian cancer.

BRIEF DESCRIPTION OF THE FIGURES

FIG. 6. In vivo therapy of athymic nude mice, bearing Capan 1 human pancreatic carcinoma, with MAb-CL2A-SN-38 conjugates.

DETAILED DESCRIPTION OF THE INVENTION

Definitions

Figure 1:
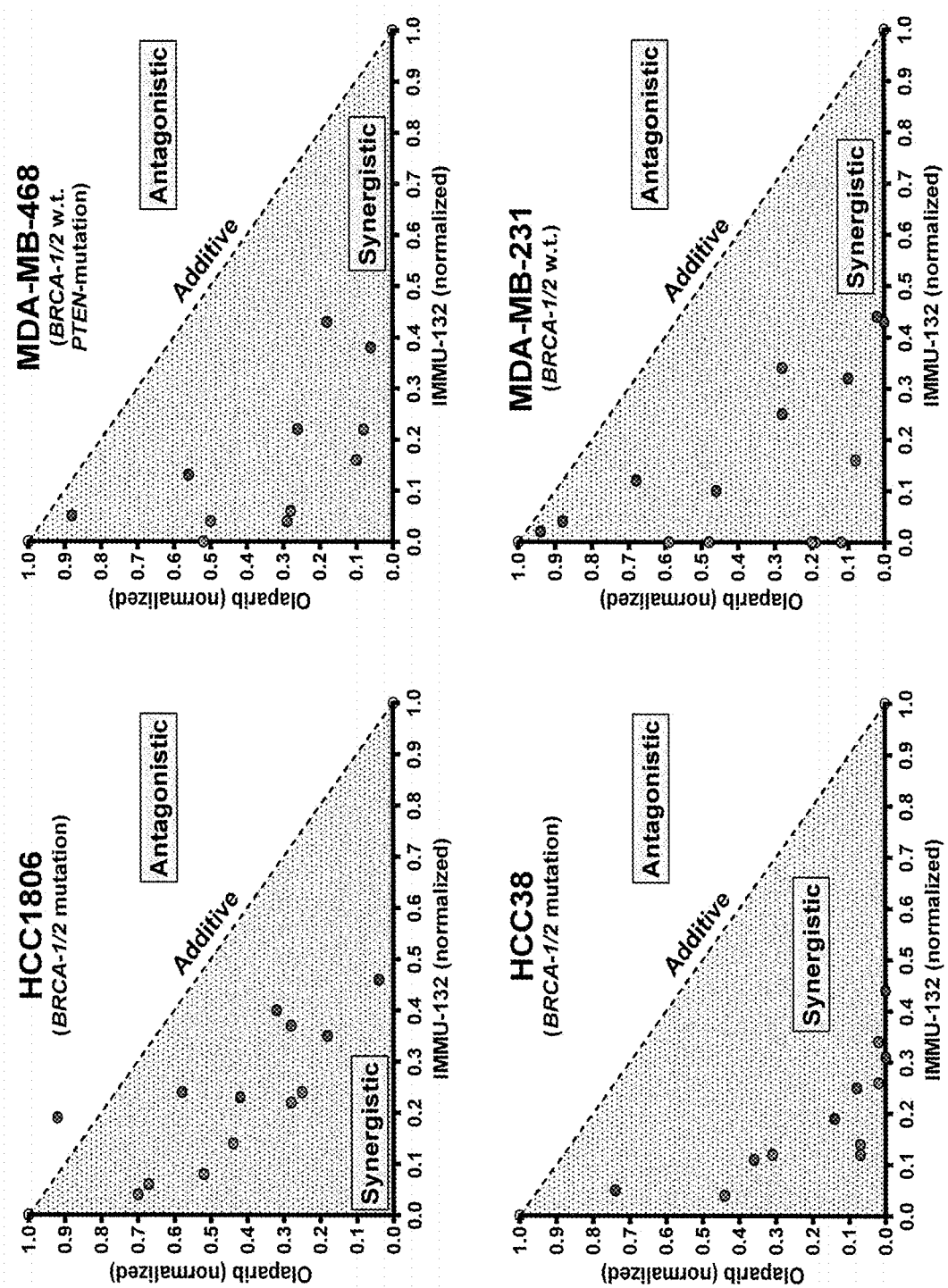
FIG. 1. Synergy of IMMU-132 plus Olaparib in 4 breast cancer cell lines. Dose/response curves for each agent alone were first tested to determine single agent $IC_{10}$-, $IC_{20}$-, or $IC_{30}$-values after a 96-h incubation. In combination assays, one agent (e.g., IMMU-132) was tested on a given cell line across a range of concentrations (i.e., dose/response curves). One set of wells only received IMMU-132. Another set received IMMU-132 as dose/response with a constant amount of olaparib (e.g., $IC_{10}$-concentration). Two other sets used olaparib at $IC_{20}$- or $IC_{30}$-concentrations. For each IMMU-132 dose/response curve, the $IC_{50}$-value was determined from these data. These values were then normalized and plotted as isobolograms. Human breast cancer cell lines tested were HCC1806 (BRCA-1/2 mutation), HCC38 (BRCA-1/2/mutation), MDA-MB-468 (BRCA-1/2 w.t., PTEN mutation) and MDA-MB-231 (BRCA-1/2 w.t.). Red dots FIG. 2. Combination index values for IMMU-132 plus olaparib, rucaparib or talazoparib in four TNBC cell lines. CI values were determined as described in Example 1.

In the description that follows, a number of terms are used and the following definitions are provided to facilitate understanding of the claimed subject matter. Terms that are not expressly defined herein are used in accordance with their plain and ordinary meanings.

Unless otherwise specified, a or an means "one or more."

The term about is used herein to mean plus or minus ten percent (10%) of a value. For example, "about 100" refers to any number between 90 and 110.

An antibody, as used herein, refers to a full-length (i.e., naturally occurring or formed by normal immunoglobulin gene fragment recombinatorial processes) immunoglobulin molecule (e.g., an IgG antibody) or an antigen-binding portion of an immunoglobulin molecule, such as an antibody fragment. An antibody or antibody fragment may be conjugated or otherwise derivatized within the scope of the claimed subject matter. Such antibodies include but are not limited to IgG1, IgG2, IgG3, IgG4 (and IgG4 subforms), as well as IgA isotypes. As used below, the abbreviation "MAb" may be used interchangeably to refer to an antibody, antibody fragment, monoclonal antibody or multispecific antibody.

An antibody fragment is a portion of an antibody such as F(ab')$_2$, F(ab)$_2$, Fab', Fab, Fv, scFv (single chain Fv), single domain antibodies (DABs or VHHs) and the like, including the half-molecules of IgG4 cited above (van der Neut Kolfschoten et al. (Science 2007; 317(14 September):1554-1557). Regardless of structure, an antibody fragment of use binds with the same antigen that is recognized by the intact antibody. The term "antibody fragment" also includes synthetic or genetically engineered proteins that act like an antibody by binding to a specific antigen to form a complex. For example, antibody fragments include isolated fragments consisting of the variable regions, such as the "Fv" fragments consisting of the variable regions of the heavy and light chains and recombinant single chain polypeptide molecules in which light and heavy variable regions are connected by a peptide linker ("scFv proteins"). The fragments may be constructed in different ways to yield multivalent and/or multispecific binding forms.

A naked antibody is generally an entire antibody that is not conjugated to a therapeutic agent. A naked antibody may exhibit therapeutic and/or cytotoxic effects, for example by Fc-dependent functions, such as complement fixation (CDC) and ADCC (antibody-dependent cell cytotoxicity). However, other mechanisms, such as apoptosis, anti-angiogenesis, anti-metastatic activity, anti-adhesion activity, inhibition of heterotypic or homotypic adhesion, and interference in signaling pathways, may also provide a therapeutic effect. Naked antibodies include polyclonal and monoclonal antibodies, naturally occurring or recombinant antibodies, such as chimeric, humanized or human antibodies and fragments thereof. In some cases a "naked antibody" may also refer to a "naked" antibody fragment. As defined herein, "naked" is synonymous with "unconjugated," and means not linked or conjugated to a therapeutic agent.

A chimeric antibody is a recombinant protein that contains the variable domains of both the heavy and light antibody chains, including the complementarity determining regions (CDRs) of an antibody derived from one species, preferably a rodent antibody, more preferably a murine antibody, while the constant domains of the antibody molecule are derived from those of a human antibody. For veterinary applications, the constant domains of the chimeric antibody may be derived from that of other species, such as a primate, cat or dog.

A humanized antibody is a recombinant protein in which the CDRs from an antibody from one species; e.g., a murine antibody, are transferred from the heavy and light variable chains of the murine antibody into human heavy and light variable domains (framework regions). The constant domains of the antibody molecule are derived from those of a human antibody. In some cases, specific residues of the framework region of the humanized antibody, particularly those that are touching or close to the CDR sequences, may be modified, for example replaced with the corresponding residues from the original murine, rodent, subhuman primate, or other antibody.

A human antibody is an antibody obtained, for example, from transgenic mice that have been "engineered" to produce human antibodies in response to antigenic challenge. In this technique, elements of the human heavy and light chain loci are introduced into strains of mice derived from embryonic stem cell lines that contain targeted disruptions of the endogenous heavy chain and light chain loci. The transgenic mice can synthesize human antibodies specific for various antigens, and the mice can be used to produce human antibody-secreting hybridomas. Methods for obtaining human antibodies from transgenic mice are described by Green et al., *Nature Genet.* 7:13 (1994), Lonberg et al., *Nature* 368:856 (1994), and Taylor et al., *Int. Immun.* 6:579 (1994). A fully human antibody also can be constructed by genetic or chromosomal transfection methods, as well as phage display technology, all of which are known in the art. See for example, McCafferty et al., *Nature* 348:552-553 (1990) for the production of human antibodies and fragments thereof in vitro, from immunoglobulin variable domain gene repertoires from unimmunized donors. In this technique, human antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see e.g. Johnson and Chiswell, *Current Opinion in Structural Biology* 3:5564-571 (1993). Human antibodies may also be generated by in vitro activated B cells. See U.S. Pat. Nos. 5,567,610 and 5,229,275, the Examples section of each of which is incorporated herein by reference.

A therapeutic agent is an atom, molecule, or compound that is useful in the treatment of a disease. Examples of therapeutic agents include, but are not limited to, antibodies, antibody fragments, immunoconjugates, drugs, cytotoxic agents, pro-apopoptotic agents, toxins, nucleases (including DNAses and RNAses), hormones, immunomodulators, chelators, boron compounds, photoactive agents or dyes, radionuclides, oligonucleotides, interference RNA, siRNA, RNAi, anti-angiogenic agents, chemotherapeutic agents, cyokines, chemokines, prodrugs, enzymes, binding proteins or peptides or combinations thereof.

An immunoconjugate is an antibody, antigen-binding antibody fragment, antibody complex or antibody fusion protein that is conjugated to at least one therapeutic agent. Conjugation may be covalent or non-covalent. Preferably, conjugation is covalent.

As used herein, the term antibody fusion protein is a recombinantly-produced antigen-binding molecule in which one or more natural antibodies, single-chain antibodies or antibody fragments are linked to another moiety, such as a protein or peptide, a toxin, a cytokine, a hormone, etc. In certain preferred embodiments, the fusion protein may comprise two or more of the same or different antibodies, antibody fragments or single-chain antibodies fused together, which may bind to the same epitope, different epitopes on the same antigen, or different antigens.

An immunomodulator is a therapeutic agent that when present, alters, suppresses or stimulates the body's immune system. Typically, an immunomodulator of use stimulates immune cells to proliferate or become activated in an immune response cascade, such as macrophages, dendritic cells, B-cells, and/or T-cells. However, in some cases an immunomodulator may suppress proliferation or activation of immune cells. An example of an immunomodulator as described herein is a cytokine, which is a soluble small protein of approximately 5-20 kDa that is released by one cell population (e.g., primed T-lymphocytes) on contact with specific antigens, and which acts as an intercellular mediator between cells. As the skilled artisan will understand, examples of cytokines include lymphokines, monokines, interleukins, and several related signaling molecules, such as tumor necrosis factor (TNF) and interferons. Chemokines are a subset of cytokines. Certain interleukins and interferons are examples of cytokines that stimulate T cell or other immune cell proliferation. Exemplary interferons include interferon-$\alpha$, interferon-$\beta$, interferon-$\gamma$ and interferon-$\lambda$.

CPT is an abbreviation for camptothecin, and as used in the present application CPT represents camptothecin itself or an analog or derivative of camptothecin, such as SN-38. The structures of camptothecin and some of its analogs, with the numbering indicated and the rings labeled with letters A-E, are given in formula 1 in Chart 1 below.

Chart 1

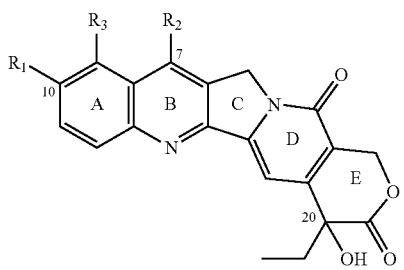

(1)

CPT: $R_1=R_2=R_3=H$
10-Hydroxy-CPT: $R_1=OH$; $R_2=R_3=H$
CPT-11: $R_1=$

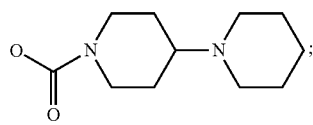

$R_2$=ethyl; $R_3$=H
SN-38: $R_1=OH$; $R_2$=ethyl; $R_3$=H
Topotecan: $R_1=OH$; $R_2=H$; $R_3=CH_2-N(CH_3)_2$ Anti-Trop-2 Antibodies The subject ADCs include at least one antibody or fragment thereof that binds to Trop-2. In a specific preferred embodiment, the anti-Trop-2 antibody may be a humanized RS7 antibody (see, e.g., U.S. Pat. No. 7,238,785, incorporated herein by reference in its entirety), comprising the light chain CDR sequences CDR1 (KASQDVSIAVA, SEQ ID NO:1); CDR2 (SASYRYT, SEQ ID NO:2); and CDR3 (QQHYITPLT, SEQ ID NO:3) and the heavy chain CDR sequences CDR1 (NYGMN, SEQ ID NO:4); CDR2 (WINTYTGEPTYTDDFKG, SEQ ID NO:5) and CDR3 (GGFGSSYWYFDV, SEQ ID NO:6).

The RS7 antibody was a murine IgG₁ raised against a crude membrane preparation of a human primary squamous cell lung carcinoma. (Stein et al., *Cancer Res.* 50: 1330, 1990) The RS7 antibody recognizes a 46-48 kDa glycoprotein, characterized as cluster 13. (Stein et al., *Int J Cancer Supp.* 8:98-102, 1994) The antigen was designated as EGP-1 (epithelial glycoprotein-1), but is also referred to as Trop-2.

Trop-2 is a type-I transmembrane protein and has been cloned from both human (Fornaro et al., *Int J Cancer* 1995; 62:610-8) and mouse cells (Sewedy et al., *Int J Cancer* 1998; 75:324-30). In addition to its role as a tumor-associated calcium signal transducer (Ripani et al., *Int J Cancer* 1998; 76:671-6), the expression of human Trop-2 was shown to be necessary for tumorigenesis and invasiveness of colon cancer cells, which could be effectively reduced with a polyclonal antibody against the extracellular domain of Trop-2 (Wang et al., *Mol Cancer Ther* 2008; 7:280-5).

The growing interest in Trop-2 as a therapeutic target for solid cancers (Cubas et al., *Biochim Biophys Acta* 2009; 1796:309-14) is attested by further reports that documented the clinical significance of overexpressed Trop-2 in breast (Huang et al., *Clin Cancer Res* 2005; 11:4357-64), colorectal (Ohmachi et al., *Clin Cancer Res* 2006; 12:3057-63; Fang et al., *Int J Colorectal Dis* 2009; 24:875-84), and oral squamous cell (Fong et al., *Modern Pathol* 2008; 21:186-91) carcinomas. The latest evidence that prostate basal cells expressing high levels of Trop-2 are enriched for in vitro and in vivo stem-like activity is particularly noteworthy (Goldstein et al., *Proc Natl Acad Sci USA* 2008; 105:20882-7).

Flow cytometry and immunohistochemical staining studies have shown that the RS7 MAb detects antigen on a variety of tumor types, with limited binding to normal human tissue (Stein et al., *Cancer Res.* 50: 1330, 1990). Trop-2 is expressed primarily by carcinomas such as carcinomas of the lung, stomach, urinary bladder, breast, ovary, uterus, and prostate. Localization and therapy studies using radiolabeled murine RS7 MAb in animal models have demonstrated tumor targeting and therapeutic efficacy (Stein et al., *Cancer Res.* 50: 1330, 1990). Strong RS7 staining has been demonstrated in tumors from the lung, breast, bladder, ovary, uterus, stomach, and prostate. (Stein et al., *Int J Cancer* 55:938, 1993) The lung cancer cases comprised both squamous cell carcinomas and adenocarcinomas. (Stein et al., *Int J Cancer* 55:938, 1993) Both cell types stained strongly, indicating that the RS7 antibody does not distinguish between histologic classes of non-small-cell carcinoma of the lung.

The RS7 MAb is rapidly internalized into target cells (Stein et al., *Int J Cancer* 55:938, 1993). The internalization rate constant for RS7 MAb is intermediate between the internalization rate constants of two other rapidly internalizing MAbs, which have been demonstrated to be useful for immunoconjugate production. (Stein et al., *Int J Cancer* 55:938, 1993). It is well documented that internalization of immunoconjugates is a requirement for anti-tumor activity. (Pastan et al., *Cell* 47:641, 1986) Internalization of drug immunoconjugates has been described as a major factor in anti-tumor efficacy. (Yang et al., *Proc. Nat'l Acad. Sci. USA* 85: 1189, 1988) Thus, the RS7 antibody exhibits several important properties for therapeutic applications.

While the hRS7 antibody is preferred, other anti-Trop-2 antibodies are known and/or publicly available and in alternative embodiments may be utilized in the subject ADCs. While humanized or human antibodies are preferred for reduced immunogenicity, in alternative embodiments a chimeric antibody may be of use. As discussed below, methods of antibody humanization are well known in the art and may be utilized to convert an available murine or chimeric antibody into a humanized form.

Anti-Trop-2 antibodies are commercially available from a number of sources and include LS-C126418, LS-C178765, LS-C126416, LS-C126417 (LifeSpan BioSciences, Inc., Seattle, Wash.); 10428-MM01, 10428-MM02, 10428-R001, 10428-R030 (Sino Biological Inc., Beijing, China); MR54 (eBioscience, San Diego, Calif.); sc-376181, sc-376746, Santa Cruz Biotechnology (Santa Cruz, Calif.); MM0588-49D6, (Novus Biologicals, Littleton, Colo.); ab79976, and ab89928 (ABCAM®, Cambridge, Mass.).

Other anti-Trop-2 antibodies have been disclosed in the patent literature. For example, U.S. Publ. No. 2013/0089872 discloses anti-Trop-2 antibodies K5-70 (Accession No. FERM BP-11251), K5-107 (Accession No. FERM BP-11252), K5-116-2-1 (Accession No. FERM BP-11253), T6-16 (Accession No. FERM BP-11346), and T5-86 (Accession No. FERM BP-11254), deposited with the International Patent Organism Depositary, Tsukuba, Japan. U.S. Pat. No. 5,840,854 disclosed the anti-Trop-2 monoclonal antibody BR110 (ATCC No. HB11698). U.S. Pat. No. 7,420,040 disclosed an anti-Trop-2 antibody produced by hybridoma cell line AR47A6.4.2, deposited with the IDAC (International Depository Authority of Canada, Winnipeg, Canada) as accession number 141205-05. U.S. Pat. No. 7,420,041 disclosed an anti-Trop-2 antibody produced by hybridoma cell line AR52A301.5, deposited with the IDAC as accession number 141205-03. U.S. Publ. No. 2013/0122020 disclosed anti-Trop-2 antibodies 3E9, 6G11, 7E6, 15E2, 18B1. Hybridomas encoding a representative antibody were deposited with the American Type Culture Collection (ATCC), Accession Nos. PTA-12871 and PTA-12872. U.S. Pat. No. 8,715,662 discloses anti-Trop-2 antibodies produced by hybridomas deposited at the AID-ICLC (Genoa, Italy) with deposit numbers PD 08019, PD 08020 and PD 08021. U.S. Patent Application Publ. No. 20120237518 discloses anti-Trop-2 antibodies 77220, KM4097 and KM4590. U.S. Pat. No. 8,309,094 (Wyeth) discloses antibodies A1 and A3, identified by sequence listing. The Examples section of each patent or patent application cited above in this paragraph is incorporated herein by reference. Non-patent publication Lipinski et al. (1981, *Proc Natl. Acad Sci USA*, 78:5147-50) disclosed anti-Trop-2 antibodies 162-25.3 and 162-46.2.

Numerous anti-Trop-2 antibodies are known in the art and/or publicly available. As discussed below, methods for preparing antibodies against known antigens were routine in the art. The sequence of the human Trop-2 protein was also known in the art (see, e.g., GenBank Accession No. CAA54801.1). Methods for producing humanized, human or chimeric antibodies were also known. The person of ordinary skill, reading the instant disclosure in light of general knowledge in the art, would have been able to make and use the genus of anti-Trop-2 antibodies in the subject ADCs.

General Antibody Techniques

Techniques for preparing monoclonal antibodies against virtually any target antigen are well known in the art. See, for example, Köhler and Milstein, *Nature* 256: 495 (1975), and Coligan et al. (eds.), CURRENT PROTOCOLS IN IMMUNOLOGY, VOL. 1, pages 2.5.1-2.6.7 (John Wiley & Sons 1991). The person of ordinary skill will realize that, where human subjects are to be treated, the antibodies preferably bind to human antigens. Briefly, monoclonal antibodies can be obtained by injecting mice with a composition comprising an antigen, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A or Protein-G Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

After the initial raising of antibodies to the immunogen, the antibodies can be sequenced and subsequently prepared by recombinant techniques. Humanization and chimerization of murine antibodies and antibody fragments are well known to those skilled in the art, as discussed below.

The skilled artisan will realize that the claimed methods and compositions may utilize any of a wide variety of antibodies known in the art. Antibodies of use may be commercially obtained from a wide variety of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and/or have published variable region sequences and are available for use in the claimed methods and compositions. See, e.g., U.S. Pat. Nos. 7,312,318; 7,282,567; 7,151,164; 7,074,403; 7,060,802; 7,056,509; 7,049,060; 7,045,132; 7,041,803; 7,041,802; 7,041,293; 7,038,018; 7,037,498; 7,012,133; 7,001,598; 6,998,468; 6,994,976; 6,994,852; 6,989,241; 6,974,863; 6,965,018; 6,964,854; 6,962,981; 6,962,813; 6,956,107; 6,951,924; 6,949,244; 6,946,129; 6,943,020; 6,939,547; 6,921,645; 6,921,645; 6,921,533; 6,919,433; 6,919,078; 6,916,475; 6,905,681; 6,899,879; 6,893,625; 6,887,468; 6,887,466; 6,884,594; 6,881,405; 6,878,812; 6,875,580; 6,872,568; 6,867,006; 6,864,062; 6,861,511; 6,861,227; 6,861,226; 6,838,282; 6,835,549; 6,835,370; 6,824,780; 6,824,778; 6,812,206; 6,793,924; 6,783,758; 6,770,450; 6,767,711; 6,764,688; 6,764,681; 6,764,679; 6,743,898; 6,733,981; 6,730,307; 6,720,155; 6,716,966; 6,709,653; 6,693,176; 6,692,908; 6,689,607; 6,689,362; 6,689,355; 6,682,737; 6,682,736; 6,682,734; 6,673,344; 6,653,104; 6,652,852; 6,635,482; 6,630,144; 6,610,833; 6,610,294; 6,605,441; 6,605,279; 6,596,852; 6,592,868; 6,576,745; 6,572,856; 6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040, 6,451,310; 6,444,206; 6,441,143; 6,432,404; 6,432,402; 6,419,928; 6,413,726; 6,406,694; 6,403,770; 6,403,091; 6,395,276; 6,395,274; 6,387,350; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459; 6,331,175; 6,306,393; 6,254,868; 6,187,287; 6,183,744; 6,129,914; 6,120,767; 6,096,289; 6,077,499; 5,922,302; 5,874,540; 5,814,440; 5,798,229; 5,789,554; 5,776,456; 5,736,119; 5,716,595; 5,677,136; 5,587,459; 5,443,953, 5,525,338, the Examples section of each of which is incorporated herein by reference. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art. Isolated antibodies may be conjugated to therapeutic agents that induce DNA strand breaks, such as camptothecins or anthracyclines, using the techniques disclosed herein.

Chimeric and Humanized Antibodies

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. Methods for constructing chimeric antibodies are well known in the art (e.g., Leung et al., 1994, *Hybridoma* 13:469).

A chimeric monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. To preserve the stability and antigen specificity of the humanized monoclonal, one or more human FR residues may be replaced by the mouse counterpart residues. Humanized monoclonal antibodies may be used for therapeutic treatment of subjects. Techniques for production of humanized monoclonal antibodies are well known in the art. (See, e.g., Jones et al., 1986, *Nature,* 321:522; Riechmann et al., *Nature,* 1988, 332:323; Verhoeyen et al., 1988, *Science,* 239:1534; Carter et al., 1992, *Proc. Nat'l Acad. Sci. USA,* 89:4285; Sandhu, *Crit. Rev. Biotech.,* 1992, 12:437; Tempest et al., 1991, *Biotechnology* 9:266; Singer et al., *J. Immun.,* 1993, 150:2844.)

Other embodiments may concern non-human primate antibodies. General techniques for raising therapeutically useful antibodies in baboons may be found, for example, in Goldenberg et al., WO 91/11465 (1991), and in Losman et al., *Int. J. Cancer* 46: 310 (1990). In another embodiment, an antibody may be a human monoclonal antibody. Such antibodies may be obtained from transgenic mice that have been engineered to produce specific human antibodies in response to antigenic challenge, as discussed below.

Human Antibodies

Methods for producing fully human antibodies using either combinatorial approaches or transgenic animals transformed with human immunoglobulin loci are known in the art (e.g., Mancini et al., 2004, *New Microbiol.* 27:315-28; Conrad and Scheller, 2005, *Comb. Chem. High Throughput Screen.* 8:117-26; Brekke and Loset, 2003, *Curr. Opin. Phamacol.* 3:544-50; each incorporated herein by reference). Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

In one alternative, the phage display technique may be used to generate human antibodies (e.g., Dantas-Barbosa et al., 2005, *Genet. Mol. Res.* 4:126-40, incorporated herein by reference). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.) Recombinant Fab were cloned from the μ, γ and κ chain antibody repertoires and inserted into a phage display library (Id.) RNAs were converted to cDNAs and used to make Fab cDNA libraries using specific primers against the heavy and light chain immunoglobulin sequences (Marks et al., 1991, *J. Mol. Biol.* 222:581-97, incorporated herein by reference). Library construction was performed according to Andris-Widhopf et al. (2000, In: *Phage Display Laboratory Manual,* Barbas et al. (eds), 1$^{st}$ edition, Cold Spring Harbor Laboratory Press, Cold Spring Harbor, N.Y. pp. 9.1 to 9.22, incorporated herein by reference). The final Fab fragments were digested with restriction endonucleases and inserted into the bacteriophage genome to make the phage display library. Such libraries may be screened by standard phage display methods. The skilled artisan will realize that this technique is exemplary only and any known method for making and screening human antibodies or antibody fragments by phage display may be utilized.

In another alternative, transgenic animals that have been genetically engineered to produce human antibodies may be used to generate antibodies against essentially any immunogenic target, using standard immunization protocols as discussed above. Methods for obtaining human antibodies from transgenic mice are described by Green et al., *Nature Genet.* 7:13 (1994), Lonberg et al., *Nature* 368:856 (1994), and Taylor et al., *Int. Immun.* 6:579 (1994). A non-limiting example of such a system is the XENOMOUSE® (e.g., Green et al., 1999, *J. Immunol. Methods* 231:11-23, incorporated herein by reference) from Abgenix (Fremont, Calif.). In the XENOMOUSE® and similar animals, the mouse antibody genes have been inactivated and replaced by functional human antibody genes, while the remainder of the mouse immune system remains intact.

The XENOMOUSE® was transformed with germline-configured YACs (yeast artificial chromosomes) that contained portions of the human IgH and Ig kappa loci, including the majority of the variable region sequences, along accessory genes and regulatory sequences. The human variable region repertoire may be used to generate antibody producing B cells, which may be processed into hybridomas by known techniques. A XENOMOUSE® immunized with a target antigen will produce human antibodies by the normal immune response, which may be harvested and/or produced by standard techniques discussed above. A variety of strains of XENOMOUSE® are available, each of which is capable of producing a different class of antibody. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XENOMOUSE® system but may utilize any transgenic animal that has been genetically engineered to produce human antibodies.

Production of Antibody Fragments

Some embodiments of the claimed methods and/or compositions may concern antibody fragments. Such antibody fragments may be obtained, for example, by pepsin or papain digestion of whole antibodies by conventional methods. For example, antibody fragments may be produced by enzymatic cleavage of antibodies with pepsin to provide a 5S fragment denoted F(ab')$_2$. This fragment may be further cleaved using a thiol reducing agent and, optionally, a blocking group for the sulfhydryl groups resulting from cleavage of disulfide linkages, to produce 3.5S Fab' monovalent fragments. Alternatively, an enzymatic cleavage using pepsin produces two monovalent Fab fragments and an Fc fragment. Exemplary methods for producing antibody fragments are disclosed in U.S. Pat. Nos. 4,036,945; 4,331,647; Nisonoff et al., 1960, *Arch Biochem Biophys,* 89:230; Porter, 1959, *Biochem J,* 73:119; Edelman et al., 1967, METHODS IN ENZYMOLOGY, page 422 (Academic Press), and Coligan et al. (eds.), 1991, CURRENT PROTOCOLS IN IMMUNOLOGY, (John Wiley & Sons).

Other methods of cleaving antibodies, such as separation of heavy chains to form monovalent light-heavy chain fragments, further cleavage of fragments or other enzymatic, chemical or genetic techniques also may be used, so long as the fragments bind to the antigen that is recognized by the intact antibody. For example, Fv fragments comprise an association of $V_H$ and $V_L$ chains. This association can be noncovalent, as described in Inbar et al., 1972, *Proc. Nat'l. Acad. Sci. USA,* 69:2659. Alternatively, the variable chains may be linked by an intermolecular disulfide bond or cross-linked by chemicals such as glutaraldehyde. See Sandhu, 1992, *Crit. Rev. Biotech.*, 12:437.

Preferably, the Fv fragments comprise $V_H$ and $V_L$ chains connected by a peptide linker. These single-chain antigen binding proteins (scFv) are prepared by constructing a structural gene comprising DNA sequences encoding the $V_H$ and $V_L$ domains, connected by an oligonucleotides linker sequence. The structural gene is inserted into an expression vector that is subsequently introduced into a host cell, such as *E. coli*. The recombinant host cells synthesize a single polypeptide chain with a linker peptide bridging the two V domains. Methods for producing scFvs are well-known in the art. See Whitlow et al., 1991, *Methods: A Companion to Methods in Enzymology* 2:97; Bird et al., 1988, *Science*, 242:423; U.S. Pat. No. 4,946,778; Pack et al., 1993, *Bio/Technology*, 11:1271, and Sandhu, 1992, *Crit. Rev. Biotech.*, 12:437.

Another form of an antibody fragment is a single-domain antibody (dAb), sometimes referred to as a single chain antibody. Techniques for producing single-domain antibodies are well known in the art (see, e.g., Cossins et al., *Protein Expression and Purification*, 2007, 51:253-59; Shuntao et al., *Molec Immunol* 2006, 43:1912-19; Tanha et al., *J. Biol. Chem.* 2001, 276:24774-780). Other types of antibody fragments may comprise one or more complementarity-determining regions (CDRs). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See Larrick et al., 1991, *Methods: A Companion to Methods in Enzymology* 2:106; Ritter et al. (eds.), 1995, MONOCLONAL ANTIBODIES: PRODUCTION, ENGINEERING AND CLINICAL APPLICATION, pages 166-179 (Cambridge University Press); Birch et al., (eds.), 1995, MONOCLONAL ANTIBODIES: PRINCIPLES AND APPLICATIONS, pages 137-185 (Wiley-Liss, Inc.)

Antibody Variations

In certain embodiments, the sequences of antibodies, such as the Fc portions of antibodies, may be varied to optimize the physiological characteristics of the conjugates, such as the half-life in serum. Methods of substituting amino acid sequences in proteins are widely known in the art, such as by site-directed mutagenesis (e.g. Sambrook et al., *Molecular Cloning, A laboratory manual*, $2^{nd}$ Ed, 1989). In preferred embodiments, the variation may involve the addition or removal of one or more glycosylation sites in the Fc sequence (e.g., U.S. Pat. No. 6,254,868, the Examples section of which is incorporated herein by reference). In other preferred embodiments, specific amino acid substitutions in the Fc sequence may be made (e.g., Hornick et al., 2000, *J Nucl Med* 41:355-62; Hinton et al., 2006, *J Immunol* 176:346-56; Petkova et al. 2006, *Int Immunol* 18:1759-69; U.S. Pat. No. 7,217,797; each incorporated herein by reference).

Target Antigens and Exemplary Antibodies

In certain embodiments, the subject ADC may be administered alone, or else in combination with one or more antibodies that recognize and/or bind to human antigens that are expressed at high levels on cancer cells and that are expressed predominantly or exclusively on diseased cells versus normal tissues. More preferably, the antibodies internalize rapidly following binding. An exemplary rapidly internalizing antibody is the LL1 (anti-CD74) antibody, with a rate of internalization of approximately $8\times10^6$ antibody molecules per cell per day (e.g., Hansen et al., 1996, *Biochem J.* 320:293-300). Thus, a "rapidly internalizing" antibody may be one with an internalization rate of about $1\times10^6$ to about $1\times10^7$ antibody molecules per cell per day. Antibodies of use in the claimed compositions and methods may include MAbs with properties as recited above. Exemplary antibodies of use for therapy of, for example, cancer include but are not limited to LL1 (anti-CD74), LL2 or RFB4 (anti-CD22), veltuzumab (hA20, anti-CD20), rituximab (anti-CD20), obinutuzumab (GA101, anti-CD20), lambrolizumab (anti-PD-1 receptor), nivolumab (anti-PD-1 receptor), ipilimumab (anti-CTLA-4), RS7 (anti-epithelial glycoprotein-1 (EGP-1, also known as Trop-2)), PAM4 or KC4 (both anti-mucin), MN-14 (anti-carcinoembryonic antigen (CEA, also known as CD66e or CEACAM5), MN-15 or MN-3 (anti-CEACAM6), Mu-9 (anti-colon-specific antigen-p), Immu 31 (an anti-alpha-fetoprotein), R1 (anti-IGF-1R), A19 (anti-CD19), TAG-72 (e.g., CC49), Tn, J591 or HuJ591 (anti-PSMA (prostate-specific membrane antigen)), AB-PG1-XG1-026 (anti-PSMA dimer), D2/B (anti-PSMA), G250 (an anti-carbonic anhydrase IX MAb), L243 (anti-HLA-DR) alemtuzumab (anti-CD52), bevacizumab (anti-VEGF), cetuximab (anti-EGFR), gemtuzumab (anti-CD33), ibritumomab tiuxetan (anti-CD20); panitumumab (anti-EGFR); tositumomab (anti-CD20); PAM4 (aka clivatuzumab, anti-mucin) and trastuzumab (anti-ErbB2). Such antibodies are known in the art (e.g., U.S. Pat. Nos. 5,686,072; 5,874,540; 6,107,090; 6,183,744; 6,306,393; 6,653,104; 6,730.300; 6,899,864; 6,926,893; 6,962,702; 7,074,403; 7,230,084; 7,238,785; 7,238,786; 7,256,004; 7,282,567; 7,300,655; 7,312,318; 7,585,491; 7,612,180; 7,642,239; and U.S. Patent Application Publ. No. 20050271671; 20060193865; 20060210475; 20070087001; the Examples section of each incorporated herein by reference.) Specific known antibodies of use include hPAM4 (U.S. Pat. No. 7,282,567), hA20 (U.S. Pat. No. 7,151,164), hA19 (U.S. Pat. No. 7,109,304), hIMMU-31 (U.S. Pat. No. 7,300,655), hLL1 (U.S. Pat. No. 7,312,318,), hLL2 (U.S. Pat. No. 5,789,554), hMu-9 (U.S. Pat. No. 7,387,772), hL243 (U.S. Pat. No. 7,612,180), hMN-14 (U.S. Pat. No. 6,676,924), hMN-15 (U.S. Pat. No. 8,287,865), hR1 (U.S. patent application Ser. No. 14/061,1767), hRS7 (U.S. Pat. No. 7,238,785), hMN-3 (U.S. Pat. No. 7,541,440), AB-PG1-XG1-026 (U.S. patent application Ser. No. 11/983,372, deposited as ATCC PTA-4405 and PTA-4406) and D2/B (WO 2009/130575) the text of each recited patent or application is incorporated herein by reference with respect to the Figures and Examples sections.

Other useful antigens that may be targeted include carbonic anhydrase IX, B7, CCL19, CCL21, CSAp, HER-2/neu, BrE3, CD1, CD1a, CD2, CD3, CD4, CD5, CD8, CD11A, CD14, CD15, CD16, CD18, CD19, CD20 (e.g., C2B8, hA20, 1F5 MAbs), CD21, CD22, CD23, CD25, CD29, CD30, CD32b, CD33, CD37, CD38, CD40, CD40L, CD44, CD45, CD46, CD52, CD54, CD55, CD59, CD64, CD67, CD70, CD74, CD79a, CD80, CD83, CD95, CD126, CD133, CD138, CD147, CD154, CEACAM5, CEACAM6, CTLA-4, alpha-fetoprotein (AFP), VEGF (e.g., AVASTIN®, fibronectin splice variant), ED-B fibronectin (e.g., L19), EGP-1 (Trop-2), EGP-2 (e.g., 17-1A), EGF receptor (ErbB1) (e.g., ERBITUX®), ErbB2, ErbB3, Factor H, FHL-1, Flt-3, folate receptor, Ga 733,GRO-β, HMGB-1, hypoxia inducible factor (HIF), HM1.24, HER-2/neu, insulin-like growth factor (ILGF), IFN-γ, IFN-α, IFN-β, IFN-λ, IL-2R, IL-4R, IL-6R, IL-13R, IL-15R, IL-17R, IL-18R, IL-2, IL-6, IL-8, IL-12, IL-15, IL-17, IL-18, IL-25, IP-10, IGF-1R, Ia, HM1.24, gangliosides, HCG, the HLA-DR antigen to which L243 binds, CD66 antigens, i.e., CD66a-d or a combination thereof, MAGE, mCRP, MCP-1, MIP-1A, MIP-1B, macrophage migration-inhibitory factor (MIF), MUC1, MUC2, MUC3, MUC4, MUC5ac, placental growth factor (P1GF), PSA (prostate-specific antigen), PSMA, PAM4 antigen, PD-1 receptor, NCA-95, NCA-90, A3, A33, Ep-CAM, KS-1, Le(y), mesothelin, 5100, tenascin, TAC, Tn antigen, Thomas-Friedenreich antigens, tumor necrosis antigens, tumor angiogenesis antigens, TNF-α, TRAIL receptor (R1 and R2), Trop-2, VEGFR, RANTES, T101, as well as cancer stem cell antigens, complement factors C3, C3a, C3b, C5a, C5, and an oncogene product.

A comprehensive analysis of suitable antigen (Cluster Designation, or CD) targets on hematopoietic malignant cells, as shown by flow cytometry and which can be a guide to selecting suitable antibodies for drug-conjugated immunotherapy, is Craig and Foon, *Blood* prepublished online Jan. 15, 2008; DOL 10.1182/blood-2007-11-120535.

The CD66 antigens consist of five different glycoproteins with similar structures, CD66a-e, encoded by the carcinoembryonic antigen (CEA) gene family members, BCG, CGM6, NCA, CGM1 and CEA, respectively. These CD66 antigens (e.g., CEACAM6) are expressed mainly in granulocytes, normal epithelial cells of the digestive tract and tumor cells of various tissues. Also included as suitable targets for cancers are cancer testis antigens, such as NY-ESO-1 (Theurillat et al., *Int. J. Cancer* 2007; 120(11):2411-7), as well as CD79a in myeloid leukemia (Kozlov et al., *Cancer Genet. Cytogenet.* 2005; 163(1):62-7) and also B-cell diseases, and CD79b for non-Hodgkin's lymphoma (Poison et al., *Blood* 110(2):616-623). A number of the aforementioned antigens are disclosed in U.S. Provisional Application Ser. No. 60/426,379, entitled "Use of Multi-specific, Non-covalent Complexes for Targeted Delivery of Therapeutics," filed Nov. 15, 2002. Cancer stem cells, which are ascribed to be more therapy-resistant precursor malignant cell populations (Hill and Perris, *J. Natl. Cancer Inst.* 2007; 99:1435-40), have antigens that can be targeted in certain cancer types, such as CD133 in prostate cancer (Maitland et al., *Ernst Schering Found. Sympos. Proc.* 2006; 5:155-79), non-small-cell lung cancer (Donnenberg et al., *J. Control Release* 2007; 122(3):385-91), and glioblastoma (Beier et al., *Cancer Res.* 2007; 67(9):4010-5), and CD44 in colorectal cancer (Dalerba er al., *Proc. Natl. Acad. Sci. USA* 2007; 104(24) 10158-63), pancreatic cancer (Li et al., *Cancer Res.* 2007; 67(3):1030-7), and in head and neck squamous cell carcinoma (Prince et al., *Proc. Natl. Acad. Sci. USA* 2007; 104(3)973-8).

For multiple myeloma therapy, suitable targeting antibodies have been described against, for example, CD38 and CD138 (Stevenson, *Mol Med* 2006; 12(11-12):345-346; Tassone et al., *Blood* 2004; 104(12):3688-96), CD74 (Stein et al., ibid.), CS1 (Tai et al., *Blood* 2008; 112(4):1329-37, and CD40 (Tai et al., 2005; *Cancer Res.* 65(13):5898-5906).

Macrophage migration inhibitory factor (MIF) is an important regulator of innate and adaptive immunity and apoptosis. It has been reported that CD74 is the endogenous receptor for MIF (Leng et al., 2003, *J Exp Med* 197:1467-76). The therapeutic effect of antagonistic anti-CD74 antibodies on MIF-mediated intracellular pathways may be of use for treatment of a broad range of disease states, such as cancers of the bladder, prostate, breast, lung, colon and chronic lymphocytic leukemia (e.g., Meyer-Siegler et al., 2004, *BMC Cancer* 12:34; Shachar & Haran, 2011, *Leuk Lymphoma* 52:1446-54); autoimmune diseases such as rheumatoid arthritis and systemic lupus erythematosus (Morand & Leech, 2005, *Front Biosci* 10:12-22; Shachar & Haran, 2011, *Leuk Lymphoma* 52:1446-54); kidney diseases such as renal allograft rejection (Lan, 2008, *Nephron Exp Nephrol.* 109:e79-83); and numerous inflammatory diseases (Meyer-Siegler et al., 2009, *Mediators Inflamm* epub Mar. 22, 2009; Takahashi et al., 2009, *Respir Res* 10:33; Milatuzumab (hLL1) is an exemplary anti-CD74 antibody of therapeutic use for treatment of MIF-mediated diseases.

Bispecific and Multispecific Antibodies

Bispecific antibodies are useful in a number of biomedical applications. For instance, a bispecific antibody with binding sites for a tumor cell surface antigen and for a T-cell surface receptor can direct the lysis of specific tumor cells by T cells. Bispecific antibodies recognizing gliomas and the CD3 epitope on T cells have been successfully used in treating brain tumors in human patients (Nitta, et al. *Lancet.* 1990; 355:368-371). A preferred bispecific antibody is an anti-CD3 X anti-Trop-2 antibody. Such bispecific mAbs may be used in combination with the subject ADC.

Numerous methods to produce bispecific or multispecific antibodies are known, as disclosed, for example, in U.S. Pat. No. 7,405,320, the Examples section of which is incorporated herein by reference. Bispecific antibodies can be produced by the quadroma method, which involves the fusion of two different hybridomas, each producing a monoclonal antibody recognizing a different antigenic site (Milstein and Cuello, *Nature,* 1983; 305:537-540).

Another method for producing bispecific antibodies uses heterobifunctional cross-linkers to chemically tether two different monoclonal antibodies (Staerz, et al. *Nature,* 1985; 314:628-631; Perez, et al. *Nature,* 1985; 316:354-356). Bispecific antibodies can also be produced by reduction of each of two parental monoclonal antibodies to the respective half molecules, which are then mixed and allowed to reoxidize to obtain the hybrid structure (Staerz and Bevan. *Proc Natl Acad Sci USA.* 1986; 83:1453-1457). Another alternative involves chemically cross-linking two or three separately purified Fab' fragments using appropriate linkers. (See, e.g., European Patent Application 0453082).

Other methods include improving the efficiency of generating hybrid hybridomas by gene transfer of distinct selectable markers via retrovirus-derived shuttle vectors into respective parental hybridomas, which are fused subsequently (DeMonte, et al. *Proc Natl Acad Sci USA.* 1990, 87:2941-2945); or transfection of a hybridoma cell line with expression plasmids containing the heavy and light chain genes of a different antibody.

Cognate $V_H$ and $V_L$ domains can be joined with a peptide linker of appropriate composition and length (usually consisting of more than 12 amino acid residues) to form a single-chain Fv (scFv) with binding activity. Methods of manufacturing scFvs are disclosed in U.S. Pat. Nos. 4,946,778 and 5,132,405, the Examples section of each of which is incorporated herein by reference. Reduction of the peptide linker length to less than 12 amino acid residues prevents pairing of $V_H$ and $V_L$ domains on the same chain and forces pairing of $V_H$ and $V_L$ domains with complementary domains on other chains, resulting in the formation of functional multimers. Polypeptide chains of $V_H$ and $V_L$ domains that are joined with linkers between 3 and 12 amino acid residues form predominantly dimers (termed diabodies). With linkers between 0 and 2 amino acid residues, trimers (termed triabody) and tetramers (termed tetrabody) are favored, but the exact patterns of oligomerization appear to depend on the composition as well as the orientation of V-domains ($V_H$-linker-$V_L$ or $V_L$-linker-$V_H$), in addition to the linker length.

These techniques for producing multispecific or bispecific antibodies exhibit various difficulties in terms of low yield, necessity for purification, low stability or the labor-intensiveness of the technique. More recently, a technique known as "dock and lock" (DNL) has been utilized to produce combinations of virtually any desired antibodies, antibody fragments and other effector molecules (see, e.g., U.S. Pat. Nos. 7,521,056; 7,527,787; 7,534,866; 7,550,143; 7,666,400; 7,858,070; 7,871,622; 7,906,121; 7,906,118; 8,163,291; 7,901,680; 7,981,398; 8,003,111 and 8,034,352, the Examples section of each of which incorporated herein by reference). The technique utilizes complementary protein binding domains, referred to as anchoring domains (AD) and dimerization and docking domains (DDD), which bind to each other and allow the assembly of complex structures, ranging from dimers, trimers, tetramers, quintamers and hexamers. These form stable complexes in high yield without requirement for extensive purification. The DNL technique allows the assembly of monospecific, bispecific or multispecific antibodies. Any of the techniques known in the art for making bispecific or multispecific antibodies may be utilized in the practice of the presently claimed methods.

In various embodiments, a conjugate as disclosed herein may be part of a composite, multispecific antibody. Such antibodies may contain two or more different antigen binding sites, with differing specificities. The multispecific composite may bind to different epitopes of the same antigen, or alternatively may bind to two different antigens.

Antibody Allotypes

Immunogenicity of therapeutic antibodies is associated with increased risk of infusion reactions and decreased duration of therapeutic response (Baert et al., 2003, *N Engl J Med* 348:602-08). The extent to which therapeutic antibodies induce an immune response in the host may be determined in part by the allotype of the antibody (Stickler et al., 2011, *Genes and Immunity* 12:213-21). Antibody allotype is related to amino acid sequence variations at specific locations in the constant region sequences of the antibody. The allotypes of IgG antibodies containing a heavy chain γ-type constant region are designated as Gm allotypes (1976, *J Immunol* 117:1056-59).

For the common IgG1 human antibodies, the most prevalent allotype is G1m1 (Stickler et al., 2011, *Genes and Immunity* 12:213-21). However, the G1m3 allotype also occurs frequently in Caucasians (Id.). It has been reported that G1m1 antibodies contain allotypic sequences that tend to induce an immune response when administered to non-G1m1 (nG1m1) recipients, such as G1m3 patients (Id.). Non-G1m1 allotype antibodies are not as immunogenic when administered to G1m1 patients (Id.).

The human G1m1 allotype comprises the amino acids aspartic acid at Kabat position 356 and leucine at Kabat position 358 in the CH3 sequence of the heavy chain IgG1. The nG1m1 allotype comprises the amino acids glutamic acid at Kabat position 356 and methionine at Kabat position 358. Both G1m1 and nG1m1 allotypes comprise a glutamic acid residue at Kabat position 357 and the allotypes are sometimes referred to as DEL and EEM allotypes. A non-limiting example of the heavy chain constant region sequences for G1m1 and nG1m1 allotype antibodies is shown for the exemplary antibodies rituximab (SEQ ID NO:7) and veltuzumab (SEQ ID NO:8).

```
Rituximab heavy chain variable region sequence
                                          (SEQ ID NO: 7)
ASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDK

KAEPKSCDKTHTCPPCPAPELLGGPSVFLFPPKPKDTLMISRTPEVTC

VVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFF

LYSKLTVDKSRWQQGNVFSCSVMHEALHNHYTQKSLSLSPGK

Veltuzumab heavy chain variable region
                                          (SEQ ID NO: 8)
ASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDK

RVEPKSCDKTHTCPPCPAPELLGGPSVFLFPPKPKDTLMISRTPEVTC

VVVDVSHEDPEVKFNWYVDGVEVHNAKTKPREEQYNSTYRVVSVLTVL

HQDWLNGKEYKCKVSNKALPAPIEKTISKAKGQPREPQVYTLPPSREE

MTKNQVSLTCLVKGFYPSDIAVEWESNGQPENNYKTTPPVLDSDGSFF

LYSKLTVDKSRWQQGNVFSCSVMHEALHNHYTQKSLSLSPGK
```

Jefferis and Lefranc (2009, *mAbs* 1:1-7) reviewed sequence variations characteristic of IgG allotypes and their effect on immunogenicity. They reported that the G1m3 allotype is characterized by an arginine residue at Kabat position 214, compared to a lysine residue at Kabat 214 in the G1m17 allotype. The nG1m1,2 allotype was characterized by glutamic acid at Kabat position 356, methionine at Kabat position 358 and alanine at Kabat position 431. The G1m1,2 allotype was characterized by aspartic acid at Kabat position 356, leucine at Kabat position 358 and glycine at Kabat position 431. In addition to heavy chain constant region sequence variants, Jefferis and Lefranc (2009) reported allotypic variants in the kappa light chain constant region, with the Km1 allotype characterized by valine at Kabat position 153 and leucine at Kabat position 191, the Km1,2 allotype by alanine at Kabat position 153 and leucine at Kabat position 191, and the Km3 allotypoe characterized by alanine at Kabat position 153 and valine at Kabat position 191.

With regard to therapeutic antibodies, veltuzumab and rituximab are, respectively, humanized and chimeric IgG1 antibodies against CD20, of use for therapy of a wide variety of hematological malignancies. Table 1 compares the allotype sequences of rituximab vs. veltuzumab. As shown in Table 1, rituximab (G1m17,1) is a DEL allotype IgG1, with an additional sequence variation at Kabat position 214 (heavy chain CH1) of lysine in rituximab vs. arginine in veltuzumab. It has been reported that veltuzumab is less immunogenic in subjects than rituximab (see, e.g., Morchhauser et al., 2009, *J Clin Oncol* 27:3346-53; Goldenberg et al., 2009, *Blood* 113:1062-70; Robak & Robak, 2011, *BioDrugs* 25:13-25), an effect that has been attributed to the difference between humanized and chimeric antibodies. However, the difference in allotypes between the EEM and DEL allotypes likely also accounts for the lower immunogenicity of veltuzumab.

TABLE 1

Allotypes of Rituximab vs. Veltuzumab

| | Complete allotype | 214 | (allotype) | 356/358 | (allotype) | 431 | (allotype) |
|---|---|---|---|---|---|---|---|
| | | | Heavy chain position and associated allotypes | | | | |
| Rituximab | G1m17,1 | K | 17 | D/L | 1 | A | — |
| Veltuzumab | G1m3 | R | 3 | E/M | — | A | — |

In order to reduce the immunogenicity of therapeutic antibodies in individuals of nG1m1 genotype, it is desirable to select the allotype of the antibody to correspond to the G1m3 allotype, characterized by arginine at Kabat 214, and the nG1m1,2 null-allotype, characterized by glutamic acid at Kabat position 356, methionine at Kabat position 358 and alanine at Kabat position 431. Surprisingly, it was found that repeated subcutaneous administration of G1m3 antibodies over a long period of time did not result in a significant immune response. In alternative embodiments, the human IgG4 heavy chain in common with the G1m3 allotype has arginine at Kabat 214, glutamic acid at Kabat 356, methionine at Kabat 359 and alanine at Kabat 431. Since immunogenicity appears to relate at least in part to the residues at those locations, use of the human IgG4 heavy chain constant region sequence for therapeutic antibodies is also a preferred embodiment. Combinations of G1m3 IgG1 antibodies with IgG4 antibodies may also be of use for therapeutic administration.

Conjugation Protocols

The preferred conjugation protocol is based on a thiol-maleimide, a thiol-vinylsulfone, a thiol-bromoacetamide, or a thiol-iodoacetamide reaction that is facile at neutral or acidic pH. This obviates the need for higher pH conditions for conjugations as, for instance, would be necessitated when using active esters. Further details of exemplary conjugation protocols are described below in the Examples section.

Therapeutic Treatment

In another aspect, the invention relates to a method of treating a subject, comprising administering a therapeutically effective amount of an ADC as described herein to a subject, preferably in combination with a PARP inhibitor and/or microtubule inhibitor. Such therapeutics can be given once or repeatedly, depending on the disease state and tolerability of the conjugate, and can also be used optionally in combination with other therapeutic modalities, such as surgery, external radiation, radioimmunotherapy, immunotherapy, chemotherapy, antisense therapy, interference RNA therapy, gene therapy, and the like. Each combination will be adapted to the tumor type, stage, patient condition and prior therapy, and other factors considered by the managing physician.

As used herein, the term "subject" refers to any animal (i.e., vertebrates and invertebrates) including, but not limited to mammals, including humans. It is not intended that the term be limited to a particular age or sex. Thus, adult and newborn subjects, as well as fetuses, whether male or female, are encompassed by the term. Doses given herein are for humans, but can be adjusted to the size of other mammals, as well as children, in accordance with weight or square meter size. Where an ADC is administered to a human subject, the person of ordinary skill will realize that the target antigen to which the ADC binds will be a human antigen.

In a preferred embodiment, ADCs comprising an anti-EGP-1 (anti-Trop-2) antibody, such as the hRS7 Mab, can be used to treat carcinomas such as carcinomas of the esophagus, pancreas, lung, stomach, colon and rectum, urinary bladder, breast, ovary, uterus, kidney and prostate, as disclosed in U.S. Pat. Nos. 7,238,785; 7,517,964 and 8,084,583, the Examples section of which is incorporated herein by reference. An hRS7 antibody is a humanized antibody that comprises light chain complementarity-determining region (CDR) sequences CDR1 (KASQDVSIAVA, SEQ ID NO:1); CDR2 (SASYRYT, SEQ ID NO:2); and CDR3 (QQHYITPLT, SEQ ID NO:3) and heavy chain CDR sequences CDR1 (NYGMN, SEQ ID NO:4); CDR2 (WINTYTGEPTYTDDFKG, SEQ ID NO:5) and CDR3 (GGFGSSYWYFDV, SEQ ID NO:6).

In another preferred embodiment, a therapeutic agent used in combination with the ADCs of this invention may comprise one or more isotopes. Radioactive isotopes useful for treating diseased tissue include, but are not limited to—$^{111}$In, $^{177}$Lu, $^{212}$Bi, $^{213}$Bi, $^{211}$At, $^{62}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, $^{227}$Th and $^{211}$Pb. The therapeutic radionuclide preferably has a decay-energy in the range of 20 to 6,000 keV, preferably in the ranges 60 to 200 keV for an Auger emitter, 100-2,500 keV for a beta emitter, and 4,000-6,000 keV for an alpha emitter. Maximum decay energies of useful beta-particle-emitting nuclides are preferably 20-5,000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, I-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213, Th-227 and Fm-255. Decay energies of useful alpha-particle-emitting radionuclides are preferably 2,000-10,000 keV, more preferably 3,000-8,000 keV, and most preferably 4,000-7,000 keV. Additional potential radioisotopes of use include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb, and the like.

Radionuclides and other metals may be delivered, for example, using chelating groups attached to an ADC. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates, such as macrocyclic polyethers for complexing $^{223}$Ra, may be used.

Therapeutic agents of use in combination with the ADCs described herein also include, for example, chemotherapeutic drugs such as vinca alkaloids, anthracyclines, epidophyllotoxins, taxanes, antimetabolites, tyrosine kinase inhibitors, Bruton tyrosine kinase inhibitors, microtubule inhibitors, PARP inhibitors, PI3K inhibitors, alkylating agents, antibiotics, Cox-2 inhibitors, antimitotics, antiangiogenic and proapoptotic agents, particularly doxorubicin, methotrexate, taxol, other camptothecins, and others from these and other classes of anticancer agents, and the like. Other cancer chemotherapeutic drugs include nitrogen mustards, alkyl sulfonates, nitrosoureas, triazenes, folic acid analogs, pyrimidine analogs, purine analogs, platinum coordination complexes, hormones, and the like. Suitable chemotherapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable chemotherapeutic agents, such as experimental drugs, are known to those of skill in the art.

Exemplary drugs of use include, but are not limited to, 5-fluorouracil, afatinib, aplidin, azaribine, anastrozole, anthracyclines, axitinib, AVL-101, AVL-291, bendamustine, bleomycin, bortezomib, bosutinib, bryostatin-1, busulfan, calicheamycin, camptothecin, carboplatin, 10-hydroxycamptothecin, carmustine, celebrex, chlorambucil, cisplatin (CDDP), Cox-2 inhibitors, irinotecan (CPT-11), SN-38, carboplatin, cladribine, camptothecans, crizotinib, cyclophosphamide, cytarabine, dacarbazine, dasatinib, dinaciclib, docetaxel, dactinomycin, daunorubicin, doxorubicin, 2-pyrrolinodoxorubicine (2PDOX), pro-2PDOX, cyanomorpholino doxorubicin, doxorubicin glucuronide, epirubicin glucuronide, erlotinib, estramustine, epidophyllotoxin, erlotinib, entinostat, estrogen receptor binding agents, etoposide (VP16), etoposide glucuronide, etoposide phosphate, exemestane, fingolimod, floxuridine (FUdR), 3',5'-O-dioleoyl-FudR (FUdR-dO), fludarabine, flutamide, farnesyl-protein transferase inhibitors, flavopiridol, fostamatinib, ganetespib, GDC-0834, GS-1101, gefitinib, gemcitabine, hydroxyurea, ibrutinib, idarubicin, idelalisib, ifosfamide, imatinib, L-asparaginase, lapatinib, lenolidamide, leucovorin, LFM-A13, lomustine, mechlorethamine, melphalan, mercaptopurine, 6-mercaptopurine, methotrexate, mitoxantrone, mithramycin, mitomycin, mitotane, navelbine, neratinib, nilotinib, nitrosurea, olaparib, plicomycin, procarbazine, paclitaxel, PCI-32765, pentostatin, PSI-341, raloxifene, semustine, sorafenib, streptozocin, SU11248, sunitinib, tamoxifen, temazolomide (an aqueous form of DTIC), transplatinum, thalidomide, thioguanine, thiotepa, teniposide, topotecan, uracil mustard, vatalanib, vinorelbine, vinblastine, vincristine, vinca alkaloids and ZD1839. Such agents may be part of the conjugates described herein or may alternatively be administered in combination with the described conjugates, either prior to, simultaneously with or after the conjugate. Alternatively, one or more therapeutic naked antibodies as are known in the art may be used in combination with the described conjugates. Exemplary therapeutic naked antibodies are described above.

In preferred embodiments, a therapeutic agent to be used in combination with a DNA-breaking antibody conjugate (e.g., an SN-38-ADC) is a microtubule inhibitor, such as a vinca alkaloid, a taxanes, a maytansinoid or an auristatin. Exemplary known microtubule inhibitors include paclitaxel, vincristine, vinblastine, mertansine, epothilone, docetaxel, discodermolide, combrestatin, podophyllotoxin, CI-980, phenylahistins, steganacins, curacins, 2-methoxy estradiol, E7010, methoxy benzenesuflonamides, vinorelbine, vinflunine, vindesine, dolastatins, spongistatin, rhizoxin, tasidotin, halichondrins, hemiasterlins, cryptophycin 52, MMAE and eribulin mesylate.

In an alternative preferred embodiment, a therapeutic agent to be used in combination with a DNA-breaking ADC, such as an SN-38-antibody conjugate, is a PARP inhibitor, such as olaparib, talazoparib (BMN-673), rucaparib, veliparib, CEP 9722, MK 4827, BGB-290, ABT-888, AG014699, BSI-201, CEP-8983 or 3-aminobenzamide.

In another alternative, a therapeutic agent used in combination with an ADC is a Bruton kinase inhibitor, such as ibrutinib (PCI-32765), PCI-45292, CC-292 (AVL-292), ONO-4059, GDC-0834, LFM-A13 or RN486.

In yet another alternative, a therapeutic agent used in combination with an ADC is a PI3K inhibitor, such as idelalisib, Wortmannin, demethoxyviridin, perifosine, PX-866, IPI-145 (duvelisib), BAY 80-6946, BEZ235, RP6530, TGR1202, SF1126, INK1117, GDC-0941, BKM120, XL147, XL765, Palomid 529, GSK1059615, ZSTK474, PWT33597, IC87114, TG100-115, CAL263, PI-103, GNE477, CUDC-907, AEZS-136 or LY294002.

Therapeutic agents that may be used in concert with the ADCs also may comprise toxins conjugated to targeting moieties. Toxins that may be used in this regard include ricin, abrin, ribonuclease (RNase), DNase I, Staphylococcal enterotoxin-A, pokeweed antiviral protein, gelonin, diphtheria toxin, *Pseudomonas* exotoxin, and *Pseudomonas* endotoxin. (See, e.g., Pastan. et al., *Cell* (1986), 47:641, and Sharkey and Goldenberg, C A *Cancer J Clin.* 2006 July-August; 56(4):226-43.) Additional toxins suitable for use herein are known to those of skill in the art and are disclosed in U.S. Pat. No. 6,077,499.

Yet another class of therapeutic agent may comprise one or more immunomodulators. Immunomodulators of use may be selected from a cytokine, a stem cell growth factor, a lymphotoxin, an hematopoietic factor, a colony stimulating factor (CSF), an interferon (IFN), erythropoietin, thrombopoietin and a combination thereof. Specifically useful are lymphotoxins such as tumor necrosis factor (TNF), hematopoietic factors, such as interleukin (IL), colony stimulating factor, such as granulocyte-colony stimulating factor (G-CSF) or granulocyte macrophage-colony stimulating factor (GM-CSF), interferon, such as interferons-α, -β, -γ or -λ, and stem cell growth factor, such as that designated "S1 factor". Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-α and -ß; mullerian-inhibiting substance; mouse gonadotropin-associated peptide; inhibin; activin; vascular endothelial growth factor; integrin; thrombopoietin (TPO); nerve growth factors such as NGF-ß; platelet-growth factor; transforming growth factors (TGFs) such as TGF-α and TGF-ß; insulin-like growth factor-I and -II; erythropoietin (EPO); osteoinductive factors; interferons such as interferon-α, -β, and -γ; colony stimulating factors (CSFs) such as macrophage-CSF (M-CSF); interleukins (ILs) such as IL-1, IL-1α, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21, IL-25, LIF, kit-ligand or FLT-3, angiostatin, thrombospondin, endostatin, tumor necrosis factor and lymphotoxin (LT). As used herein, the term cytokine includes proteins from natural sources or from recombinant cell culture and biologically active equivalents of the native sequence cytokines.

Chemokines of use include RANTES, MCAF, MIP1-alpha, MIP1-Beta and IP-10.

The person of ordinary skill will realize that the subject ADCs may be used alone or in combination with one or more other therapeutic agents, such as a second antibody, second antibody fragment, second immunoconjugate, radionuclide, toxin, drug, chemotherapeutic agent, radiation therapy, chemokine, cytokine, immunomodulator, enzyme, hormone, oligonucleotide, RNAi or siRNA. Preferably, the therapeutic agent is a PARP inhibitor, a microtubule inhibitor, a Bruton kinase inhibitor or a PI3K inhibitor.

Checkpoint Inhibitor Antibodies

In certain embodiments, the subject ADC and/or PARPi or microtubule inhibitor may be used in further combination with a checkpoint inhibitor. Studies with checkpoint inhibitor antibodies for cancer therapy have generated unprecedented response rates in cancers previously thought to be resistant to cancer treatment (see, e.g., Ott & Bhardwaj, 2013, Frontiers in Immunology 4:346; Menzies & Long, 2013, Ther Adv Med Oncol 5:278-85; Pardoll, 2012, Nature Reviews 12:252-264; Mavilio & Lugli,). Therapy with antagonistic checkpoint blocking antibodies against CTLA-4, PD-1 and PD-L1 are one of the most promising new avenues of immunotherapy for cancer and other diseases. In contrast to the majority of anti-cancer agents, checkpoint inhibitor do not target tumor cells directly, but rather target lymphocyte receptors or their ligands in order to enhance the endogenous antitumor activity of the immune system. (Pardoll, 2012, Nature Reviews 12:252-264) Because such antibodies act primarily by regulating the immune response to diseased cells, they may be used in combination with other therapeutic modalities, such as the subject ADC, PARPi and/or microtubule inhibitors, to enhance the anti-tumor effect of the combination therapy.

Programmed cell death protein 1 (PD-1, also known as CD279) encodes a cell surface membrane protein of the immunoglobulin superfamily, which is expressed in B cells and NK cells (Shinohara et al., 1995, Genomics 23:704-6; Blank et al., 2007, Cancer Immunol Immunother 56:739-45; Finger et al., 1997, Gene 197:177-87; Pardoll, 2012, Nature Reviews 12:252-264). Anti-PD1 antibodies have been used for treatment of melanoma, non-small-cell lung cancer, bladder cancer, prostate cancer, colorectal cancer, head and neck cancer, triple-negative breast cancer, leukemia, lymphoma and renal cell cancer (Topalian et al., 2012, N Engl J Med 366:2443-54; Lipson et al., 2013, Clin Cancer Res 19:462-8; Berger et al., 2008, Clin Cancer Res 14:3044-51; Gildener-Leapman et al., 2013, Oral Oncol 49:1089-96; Menzies & Long, 2013, Ther Adv Med Oncol 5:278-85).

Exemplary anti-PD1 antibodies include lambrolizumab (MK-3475, MERCK), nivolumab (BMS-936558, BRISTOL-MYERS SQUIBB), and pidilizumab (CT-011, CURETECH LTD.). Anti-PD1 antibodies are commercially available, for example from ABCAM® (AB137132), BIOLEGEND® (EH12.2H7, RMP1-14) and AFFYMETRIX EBIOSCIENCE (J105, J116, MIH4).

Programmed cell death 1 ligand 1 (PD-L1, also known as CD274) is a ligand for PD-1, found on activated T cells, B cells, myeloid cells and macrophages. The complex of PD-1 and PD-L1 inhibits proliferation of CD8+ T cells and reduces the immune response (Topalian et al., 2012, N Engl J Med 366:2443-54; Brahmer et al., 2012, N Eng J Med 366:2455-65). Anti-PDL1 antibodies have been used for treatment of non-small cell lung cancer, melanoma, colorectal cancer, renal-cell cancer, pancreatic cancer, gastric cancer, ovarian cancer, breast cancer, and hematologic malignancies (Brahmer et al., N Eng J Med 366:2455-65; Ott et al., 2013, Clin Cancer Res 19:5300-9; Radvanyi et al., 2013, Clin Cancer Res 19:5541; Menzies & Long, 2013, Ther Adv Med Oncol 5:278-85; Berger et al., 2008, Clin Cancer Res 14:13044-51).

Exemplary anti-PDL1 antibodies include MDX-1105 (MEDAREX), MEDI4736 (MEDIMMUNE) MPDL3280A (GENENTECH) and BMS-936559 (BRISTOL-MYERS SQUIBB). Anti-PDL1 antibodies are also commercially available, for example from AFFYMETRIX EBIOSCIENCE (MIH1).

Cytotoxic T-lymphocyte antigen 4 (CTLA-4, also known as CD152) is also a member of the immunoglobulin superfamily that is expressed exclusively on T-cells. CTLA-4 acts to inhibit T cell activation and is reported to inhibit helper T cell activity and enhance regulatory T cell immunosuppressive activity (Pardoll, 2012, Nature Reviews 12:252-264). Anti-CTL4A antibodies have been used in clinical trials for treatment of melanoma, prostate cancer, small cell lung cancer, non-small cell lung cancer (Robert & Ghiringhelli, 2009, Oncologist 14:848-61; Ott et al., 2013, Clin Cancer Res 19:5300; Weber, 2007, Oncologist 12:864-72; Wada et al., 2013, J Transl Med 11:89).

Exemplary anti-CTLA4 antibodies include ipilimumab (Bristol-Myers Squibb) and tremelimumab (PFIZER). Anti-CTLA4 antibodies are commercially available, for example from ABCAM® (AB134090), SINO BIOLOGICAL INC. (11159-H03H, 11159-H08H), and THERMO SCIENTIFIC PIERCE (PA5-29572, PA5-23967, PA5-26465, MA1-12205, MA1-35914). Ipilimumab has recently received FDA approval for treatment of metastatic melanoma (Wada et al., 2013, J Transl Med 11:89).

These and other known checkpoint inhibitor antibodies may be used in combination with ADCs and/or PARPi or microtubule inhibitors for improved cancer therapy.

Formulation and Administration

Suitable routes of administration of the ADCs and/or drugs include, without limitation, parenteral, subcutaneous, rectal, transmucosal, intestinal administration, intramuscular, intramedullary, intrathecal, direct intraventricular, intravenous, intravitreal, intraperitoneal, intranasal, or intraocular injections. The preferred routes of administration are parenteral. Alternatively, one may administer the compound in a local rather than systemic manner, for example, via injection of the compound directly into a solid tumor. Certain drugs, such as microtubule inhibitors and/or PARP inhibitors, may be designed to be administered orally.

ADCs can be formulated according to known methods to prepare pharmaceutically useful compositions, whereby the ADC is combined in a mixture with a pharmaceutically suitable excipient. Sterile phosphate-buffered saline is one example of a pharmaceutically suitable excipient. Other suitable excipients are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

In a preferred embodiment, the ADC is formulated in Good's biological buffer (pH 6-7), using a buffer selected from the group consisting of N-(2-acetamido)-2-aminoethanesulfonic acid (ACES); N-(2-acetamido)iminodiacetic acid (ADA); N,N-bis(2-hydroxyethyl)-2-aminoethanesulfonic acid (BES); 4-(2-hydroxyethyl)piperazine-1-ethanesulfonic acid (HEPES); 2-(N-morpholino)ethanesulfonic acid (MES); 3-(N-morpholino)propanesulfonic acid (MOPS); 3-(N-morpholinyl)-2-hydroxypropanesulfonic acid (MOPSO); and piperazine-N,N'-bis(2-ethanesulfonic acid) [Pipes]. More preferred buffers are MES or MOPS, preferably in the concentration range of 20 to 100 mM, more preferably about 25 mM. Most preferred is 25 mM MES, pH 6.5. The formulation may further comprise 25 mM trehalose and 0.01% v/v polysorbate 80 as excipients, with the final buffer concentration modified to 22.25 mM as a result of added excipients. The preferred method of storage is as a lyophilized formulation of the conjugates, stored in the temperature range of −20° C. to 2° C., with the most preferred storage at 2° C. to 8° C.

The ADC can be formulated for intravenous administration via, for example, bolus injection, slow infusion or continuous infusion. Preferably, the antibody of the present invention is infused over a period of less than about 4 hours, and more preferably, over a period of less than about 3 hours. For example, the first 25-50 mg could be infused within 30 minutes, preferably even 15 min, and the remainder infused over the next 2-3 hrs. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Additional pharmaceutical methods may be employed to control the duration of action of the therapeutic conjugate. Control release preparations can be prepared through the use of polymers to complex or adsorb the ADC. For example, biocompatible polymers include matrices of poly(ethylene-co-vinyl acetate) and matrices of a polyanhydride copolymer of a stearic acid dimer and sebacic acid. Sherwood et al., *Bio/Technology* 10: 1446 (1992). The rate of release of an ADC from such a matrix depends upon the molecular weight, the amount of ADC within the matrix, and the size of dispersed particles. Saltzman et al., *Biophys. J.* 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

Generally, the dosage of an administered ADC for humans will vary depending upon such factors as the patient's age, weight, height, sex, general medical condition and previous medical history. Dosages of ADC for administration by, for example, intravenous and/or subcutaneous administration are discussed above. The dosage may be repeated as needed, for example, once per week for 4-10 weeks, once per week for 8 weeks, or once per week for 4 weeks. It may also be given less frequently, such as every other week for several months, or monthly or quarterly for many months, as needed in a maintenance therapy. The dosage is preferably administered multiple times, once or twice a week, or as infrequently as once every 3 or 4 weeks. A minimum dosage schedule of 4 weeks, more preferably 8 weeks, more preferably 16 weeks or longer may be used. The schedule of administration may comprise administration once or twice a week, on a cycle selected from the group consisting of: (i) weekly; (ii) every other week; (iii) one week of therapy followed by two, three or four weeks off; (iv) two weeks of therapy followed by one, two, three or four weeks off; (v) three weeks of therapy followed by one, two, three, four or five week off; (vi) four weeks of therapy followed by one, two, three, four or five week off; (vii) five weeks of therapy followed by one, two, three, four or five week off; (viii) monthly and (ix) every 3 weeks. The cycle may be repeated 2, 4, 6, 8, 10, 12, 16 or 20 times or more. Alternatively, an ADC may be administered as one dosage every 2 or 3 weeks, repeated for a total of at least 3 dosages. Or, twice per week for 4-6 weeks. The dosing schedule can optionally be repeated at other intervals and dosage may be given through various parenteral routes, with appropriate adjustment of the dose and schedule.

In preferred embodiments, the ADCs are of use for therapy of cancer. Examples of cancers include, but are not limited to, carcinoma, lymphoma, glioblastoma, melanoma, sarcoma, and leukemia, myeloma, or lymphoid malignancies. More particular examples of such cancers are noted below and include: squamous cell cancer (e.g., epithelial squamous cell cancer), Ewing sarcoma, Wilms tumor, astrocytomas, glioblastomas, lung cancer including small-cell lung cancer, non-small cell lung cancer, adenocarcinoma of the lung and squamous carcinoma of the lung, cancer of the peritoneum, gastric or stomach cancer including gastrointestinal cancer, pancreatic cancer, glioblastoma multiforme, cervical cancer, ovarian cancer, liver cancer, bladder cancer, hepatoma, hepatocellular carcinoma, neuroendocrine tumors, medullary thyroid cancer, differentiated thyroid carcinoma, breast cancer, ovarian cancer, colon cancer, rectal cancer, endometrial cancer or uterine carcinoma, salivary gland carcinoma, kidney or renal cancer, prostate cancer, vulvar cancer, anal carcinoma, penile carcinoma, as well as head-and-neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

Other examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gall-bladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Polycythemia vera, Parathyroid Cancer, Penile Cancer, Pheochromocytoma, Pituitary Tumor, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenström's macroglobulinemia, Wilms' tumor, and any other hyperproliferative disease, besides neoplasia, located in an organ system listed above.

The methods and compositions described and claimed herein may be used to treat malignant or premalignant conditions and to prevent progression to a neoplastic or malignant state, including but not limited to those disorders described above. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, Basic Pathology, 2d Ed., W. B. Saunders Co., Philadelphia, pp. 68-79 (1976)).

Dysplasia is frequently a forerunner of cancer, and is found mainly in the epithelia. It is the most disorderly form of non-neoplastic cell growth, involving a loss in individual cell uniformity and in the architectural orientation of cells. Dysplasia characteristically occurs where there exists chronic irritation or inflammation. Dysplastic disorders which can be treated include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders which can be treated include, but are not limited to, benign dysproliferative disorders (e.g., benign tumors, fibrocystic conditions, tissue hypertrophy, intestinal polyps or adenomas, and esophageal dysplasia), leukoplakia, keratoses, Bowen's disease, Farmer's Skin, solar cheilitis, and solar keratosis.

In preferred embodiments, the method of the invention is used to inhibit growth, progression, and/or metastasis of cancers, in particular those listed above.

Additional hyperproliferative diseases, disorders, and/or conditions include, but are not limited to, progression, and/or metastases of malignancies and related disorders such as leukemia (including acute leukemias; e.g., acute lymphocytic leukemia, acute myelocytic leukemia [including myeloblastic, promyelocytic, myelomonocytic, monocytic, and erythroleukemia]) and chronic leukemias (e.g., chronic myelocytic [granulocytic] leukemia and chronic lymphocytic leukemia), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendroglioma, meningioma, melanoma, neuroblastoma, and retinoblastoma.

Kits

Various embodiments may concern kits containing components suitable for treating diseased tissue in a patient. Exemplary kits may contain at least one ADC as described herein. A kit may also include a drug selected from microtubule inhibitors and PARP inhibitors. If the composition containing components for administration is not formulated for delivery via the alimentary canal, such as by oral delivery, a device capable of delivering the kit components through some other route may be included. One type of device, for applications such as parenteral delivery, is a syringe that is used to inject the composition into the body of a subject. Inhalation devices may also be used.

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions to a person using a kit for its use.

EXAMPLES

Various embodiments of the present invention are illustrated by the following examples, without limiting the scope thereof.

Example 1

Synergistic Effect of Anti-Trop-2 Antibody-Drug Conjugate (ADC) in Combination Therapy with PARP Inhibitors In current clinical trials (ClinicalTrials.gov, NCT01631552), triple-negative breast cancer (TNBC) patients treated with IMMU-132 (also known as sacituzumab govitecan), which is composed of the active metabolite of irinotecan, SN-38, conjugated to an hRS7 anti-Trop-2 antibody (drug:Ab ratio=7.6), shows manageable toxicity and very encouraging responses in relapsed/refractory cases (e.g., Cardillo et al. *Clin Cancer Res* 2017 [Epub ahead of print]; Cardillo et al. *Bioconjug Chem* 2015, 26:919-31). Preclinical studies were performed to determine the utility of combinations of IMMU-132 with poly(adenosine diphosphoribose) polymerase (PARP) inhibitors in mice bearing BRCA1/2-defective (HCC1806) and wild-type (MDA-MB-468) TNBC tumor xenografts.

The purpose of this study was to determine whether combining an antibody-drug conjugate that induces DNA strand breaks, such as sacituzumab govitecan, with PARP inhibitors (e.g., olaparib) in cancer (e.g., nude mice bearing TNBC xenografts) improves anti-tumor effects. The person of ordinary skill will realize that the unexpected superior effects of the combination of antibody-SN-38 conjugates with PARP inhibitors are not limited to the specific exemplary antibody, drug, or PARP inhibitor but rather are characteristic of the classes of antibodies against tumor-associated antigens (TAAs), drugs that induce DNA strand breaks, and PARP inhibitors.

Experimental Procedures

Cell lines, antibody-drug conjugates, and PARP-inhibitors. All human cancer cell lines were purchased from the American Type Culture Collection (ATCC; Manassas, Va.). Each cell line was maintained according to the recommendations of ATCC, routinely tested for mycoplasma using MYCOALERT® Mycoplasma Detection Kit (Lonza; Rockland, Me.), and authenticated by short tandem repeat (STR) assay by the ATCC. Cells were in culture less than 6 months when employed in experiments. IMMU-132 and a control ADC (anti-CD20 hA20-SN-38) were prepared at Immunomedics, Inc., as described previously (Cardillo et al., *Clin Cancer Res* 2011; 17:3157-69). PARPi (olaparib, talazoparib, and rucaparib) were purchased and dissolved in DMSO according to the manufacturer's recommendations (Selleck Chemicals, Houston, Tex.).

In vitro studies. Human TNBC cell lines were incubated with IMMU-132 and olaparib, talazoparib or rucaparib to determine a combination index number and whether the interaction was synergistic, as well as incubating with SN-38 or IMMU-132±olaparib with analysis by Western blot or flow cytometry (FACS) for double-stranded DNA breaks, as evidenced by increases in phosphorylated histone H2AX (p-H2AX).

In vivo studies. NCr female athymic nude (nu/nu) mice, 4-8 weeks old, were purchased from Taconic Farms (Germantown, N.Y.). Xenografts were established by harvesting cells from tissue culture and mixing 1:1 with matrigel, such that each mouse received a total of $1\times10^7$ cells s.c. in the right flank. Tumor volume (TV) was determined by measurements in two dimensions using calipers, with volumes defined as: $L\times w^2/2$, where L is the longest dimension of the tumor and w the shortest. The lyophilized IMMU-132 and control ADC (anti-CD20, hA20-CL2A-SN-38) were reconstituted and diluted as required in sterile saline. Olaparib was diluted in 2-hydroxy-propyl-β-cyclodextran/PBS (10% w/v) and administered i.p. to the mice. Talazoparib and rucaparib were diluted in 10% DMAc/5% Kolliphor HS15/85% PBS and administered p.o. to the animals.

Mice bearing TNBC tumors were treated with olaparib, talazoparib, or rucaparib (as indicated) plus IMMU-132 (qwkly) for 4 wks. Study survival endpoint was tumor progression to >1.0 cm³. A partial response is defined as shrinking the tumor >30% from initial size. Stable disease is when the tumor volume remains between 70% and 120% of initial size. Time-to-tumor progression (TTP) was determined as time when tumor grew more than 20% from its nadir. Hematologic toxicity of combined IMMU-132 and olaparib was assessed in female BALB/c mice.

Synergistic effects by in vitro assay. A clonogenic assay may be used to determine survival fraction of cells (Ibrahim et al., 2012, *Cancer Discovery* 2:1036-47). Briefly, 350-800 cells were plated in 6-well flat bottom cell culture plates in duplicates. Twenty-four hours after plating, cells were washed and fresh medium was added in the presence or absence of increasing doses of ADC and/or PARP inhibitor alone and in combination. Media containing the PARP inhibitor and/or ADC was refreshed on day 4. Colonies were fixed and stained after 7 days of treatment with 1.5 ml of 6.0% glutaraldehyde and 0.5% crystal violet and colonies were counted by standard procedures. The surviving fraction (SF) of cells is calculated as follows:

$$SF = \frac{\text{Number of colonies formed after treatment}}{\text{Number of cells seeded} \times \text{Plating Efficiency}}$$

where $$\text{Plating Efficiency} = \frac{\text{Number of colonies formed in control}}{\text{Number of cells seeded}}$$

The interaction between ADC and PARP inhibitor was assessed using the multiple drug effects analysis method of Chou and Talalay (1984, *Adv Enzyme Regul* 22:27-55). This method quantitatively describes the interaction between two or more drugs, with values less than 1 indicating synergistic interactions, values greater than 1 indicating antagonistic interactions, and values equal to 1 indicating additive interactions.

A critical-Z test was performed on the survival data of treatment and control groups with P≤0.05 for any mouse deemed an outlier. Such mice were removed from further statistical analysis. Statistical analysis of tumor growth was based on area-under-the-curve (AUC). Profiles of individual tumor growth were obtained through linear-curve modeling. An F-test was employed to determine equality of variance between groups prior to statistical analysis of growth curves. A two-tailed t-test was used to assess statistical significance between the various treatment groups and controls, except for the saline control, where a one-tailed t-test was used in the comparison. Survival studies were analyzed using Kaplan-Meier plots (log-rank analysis), using the Prism GraphPad Software (v6.05) package (Advanced Graphics Software, Inc.; Encinitas, Calif.). Significance was set at P≤0.05.

Results

Initial studies were performed with IMMU-132±olaparib. In vitro, olaparib combined with SN-38 or IMMU-132 increased p-H2AX levels. Cytotoxicity assays revealed this interaction is synergistic in both BRCA1/2-defective and wild-type TNBC cell lines. In vivo, IMMU-132 plus olaparib had significant anti-tumor effects in both HCC1806 and MDA-MB-468 tumor-bearing mice when compared to single-agent responses (P<0.0017 and <0.004, respectively). In all studies, the combination of IMMU-132 with PARPi was well tolerated, with no observable toxicities (e.g., weight loss).

FIG. 1 shows the synergistic activity of IMMU-132 plus olaparib in four different human TNBC cell lines. Dose/response curves for each agent alone were first tested to determine single agent $IC_{10}$-, $IC_{20}$-, or $IC_{30}$-values after a 96-h incubation. In combination assays, one agent (e.g., IMMU-132) was tested on a given cell line across a range of concentrations (i.e., dose/response curves). One set of wells only received IMMU-132. Another set received IMMU-132 as dose/response with a constant amount of olaparib (e.g., $IC_{10}$-concentration). Two other sets used olaparib at $IC_{20}$- or $IC_{30}$-concentrations. For each IMMU-132 dose/response curve, the $IC_{50}$-value was determined from these data. These values were then normalized and plotted as isobolograms. Isobolograms of normalized $IC_{50}$-values from three separate experiments for each cell line testing the interaction of IMMU-132 and olaparib clearly showed a synergistic interaction between IMMU-132 and olaparib in each of the human breast cancer cell lines tested (FIG. 1).

The synergistic effect of combination therapy with IMMU-132 was not limited to olaparib, but rather was observed with a variety of PARPi inhibitors. Isobolograms for IMMU-132 were also clearly enhanced when combined with rucaparib, or talazoparib (not shown), demonstrating a synergistic interaction in all four cell lines (not shown). $IC_{50}$-values for IMMU-132 alone were 1.9 to 7.5 nM, whereas olaparib and rucaparib $IC_{50}$-values were 5.4 to 28.5 µM (FIG. 2). While talazoparib was more potent (4.7 to 322 nM) than either olaparib or rucaparib, $IC_{50}$-values for IMMU-132 indicated it was >2-fold more potent than talazoparib (FIG. 2). Calculated combinatorial index (C.I.) values demonstrate that even when combined with $IC_{10}$-concentrations, an additive effect was achievable (i.e., C.I.=1.0), but this was further enhanced to synergy (i.e., C.I.<1.0) when as little as $IC_{20}$-concentrations were used (FIG. 2). Importantly, this synergy occurred in both BRCA1/2-mutated and -wild-type cell lines.

Assessment of dsDNA breaks at 24-h incubation was measured in TNBC cell lines for IMMU-132 and PARPi combinations (not shown). Four TNBC cell lines were tested with IMMU-132 and olaparib (not shown). Poly(ADR-ribose) (PAR) was not detected in any of the olaparib-treated cells, while IMMU-132 alone had only a minor effect on PAR levels (not shown). When combined, PAR was still not detected, which was due to inhibition, not loss of PARP, as indicated by equivalent levels of full-length PARP (FL-PARP) present in all samples (not shown). Increased dsDNA breaks, as evidenced by increases in p-H2A.X (Bonner et al., *Nat Rev Cancer* 2008, 8:957-67), were observed in all four cell lines treated with olaparib alone, although the level in MDA-MB-231 was only 30% above untreated controls, which were set to 1.0, whereas MDA-MB-468 cells showed a 2.5-fold increase (highest response) (not shown). In three of the four cell lines, IMMU-132 treatment alone also resulted in increased p-H2A.X levels with 9 nM SN-38-equivalents of IMMU-132 (187 ng/mL of the antibody-drug conjugate, or ADC), demonstrating a >2.5-fold increase (range 2.5- to 13.9-fold) (not shown). Only the BRCA1/2-wild-type MDA-MB-231 was seemingly resistant to single-agent IMMU-132 or olaparib. However, when IMMU-132 (9 nM) was combined with olaparib, there was >5-fold increase in p-H2A.X in all four cell lines, including MDA-MB-231, which exhibited a 5.7-fold increase in p-H2A.X levels. Even at 3 nM SN-38-equivalents of IMMU-132 (62 ng/mL of the ADC), when combined with olaparib, levels of p-H2A.X rose >76% above that achieved by each agent alone in all four cell lines, with the highest response in MDA-MB-231 (171%), followed by HCC1806 (136%), MDA-MB-468(116%), and HCC38 (76%) (not shown).

Rucaparib and talazoparib were used at 10- and 100-fold lower concentrations, respectively, when combined with IMMU-132 in HCC1806 (not shown). Likewise, the amount of IMMU-132 required to demonstrate increases in dsDNA breaks, when combined with these two PARPi, was lower (0.1, 1, and 3 nM SN-38-equivalents) (not shown). Rucaparib alone resulted in a 1.6-fold increase in dsDNA breaks, whereas 0.1 nM SN-38 equivalents of IMMU-132 (2 ng/mL of the ADC) resulted in a 2.2-fold increase (not shown). Together, IMMU-132 plus rucaparib further increased the amount of dsDNA breaks 3.9-fold, which is 77% higher than either single agent (not shown). Talazoparib and IMMU-132 combined demonstrated a dose-response with the amount of dsDNA breaks increasing by 78% at the lowest IMMU-132 concentration to 216% at the highest concentration (not shown). These data demonstrate that three different PARPi, when combined with IMMU-132, result in increased DNA damage in the form of double-stranded breaks above that observed with single agent treatments, which is consistent with the in vitro cytotoxicity assays demonstrating synergistic growth-inhibition when IMMU-132 was combined with these PARPi.

Changes in cell cycle mediated by IMMU-132 plus olaparib. Cell cycle changes were assessed in all four TNBC cell lines when IMMU-132 and olaparib were incubated with asynchronistic cells for 24 h (not shown). Greater than 80% of the cells in the untreated groups were in the $G_1$-phase (not shown). Cells began to accumulate in S-phase when exposed to either olaparib or IMMU-132 alone (not shown). However, the combination demonstrated an even greater percentage of cells in S-phase, with a concomitant decrease in the percentage of cells in $G_1$-phase and little change in $G_{2/M}$ (not shown). For both BRCA1/2-mutated cells, as well as BRCA1/2-wild-type MDA-MB-231, the combination of IMMU-132 and olaparib resulted in a greater than 2-fold increase in the percentage of cells in the S-phase relative to each agent alone (not shown). MDA-MB-468 demonstrated the least increase in the percentage of cells in S-phase relative to single agent treatment, but this was due primarily to the greater effect each agent alone had, with more than 32% and 50% of the cells in S-phase upon treatment with olaparib or IMMU-132 alone, respectively (not shown). Even so, the combination increased the number of cells in S-phase by 12% over IMMU-132 alone (not shown). Similar results were observed when IMMU-132 was combined with rucaparib (1 µM) or talazoparib (0.2 µM), in which the combination of IMMU-132 plus either PARPi increased the percentage of cells in S-phase for all four cell lines, relative to single agent treatment (not shown).

Improved efficacy of IMMU-132 in mice bearing TNBC tumors when combined with olaparib or talazoparib. Therapeutic efficacy of combining IMMU-132 with olaparib was tested in HCC1806 and MDA-MB-468 tumor xenografts (FIG. 3). Importantly, in both experiments the dose and schedule of IMMU-132 administered to the animals was chosen to give only a modest therapeutic effect in order to detect a potential interaction between IMMU-132 and olaparib.

In mice bearing HCC1806 tumors (FIG. 3A), the combination therapy resulted in a significant anti-tumor effect when compared to all other treatment groups (P<0.0017, AUC; not shown). In this group, all of the mice exhibited a partial response, with 30% being tumor-free (i.e., complete response) when the experiment ended on therapy day 108. Mean time-to-tumor-progression (TTP) for this group was 36.9±8.1 days (Table 2). In contrast, tumors in mice given IMMU-132 or olaparib monotherapy progressed with mean TTP's of 17.6±3.9 and 9.1±4.8 days, respectively. Between the two monotherapy groups, IMMU-132 significantly delayed tumor progression when compared to olaparib therapy (P=0.0009). Overall, the combination had a significantly greater delay in TTP when compared to either single-agent therapy group (P<0.0001). Of note, this combination proved to be well-tolerated by the mice, with no appreciable loss in body weight (not shown). Even mice treated with 4-fold more IMMU-132 (500 µg twice weekly×4 weeks) combined with olaparib demonstrated no significant loss in weight (not shown).

In mice bearing MDA-MB-468 tumors, the combination of IMMU-132 plus olaparib had a significant anti-tumor effect when compared to all other treatment groups, including IMMU-132 monotherapy (P<0.0040; AUC, data not shown). In terms of response rate, 30% of mice treated with only IMMU-132 exhibited a partial response, as did 20% of the animals treated with olaparib (Table 2). In contrast, all of the mice in the combination group exhibited a partial response, with a TTP of 55.2±6.5 days, which was significantly better than all the other groups (P<0.0004) except IMMU-132 alone, which approached significance at a TTP of 45.1±13.6 days (P=0.0604). As in the HCC1806 tumor model, the mice tolerated the combination of IMMU-132 and olaparib without loss of body weight (not shown).

Figure 3A:
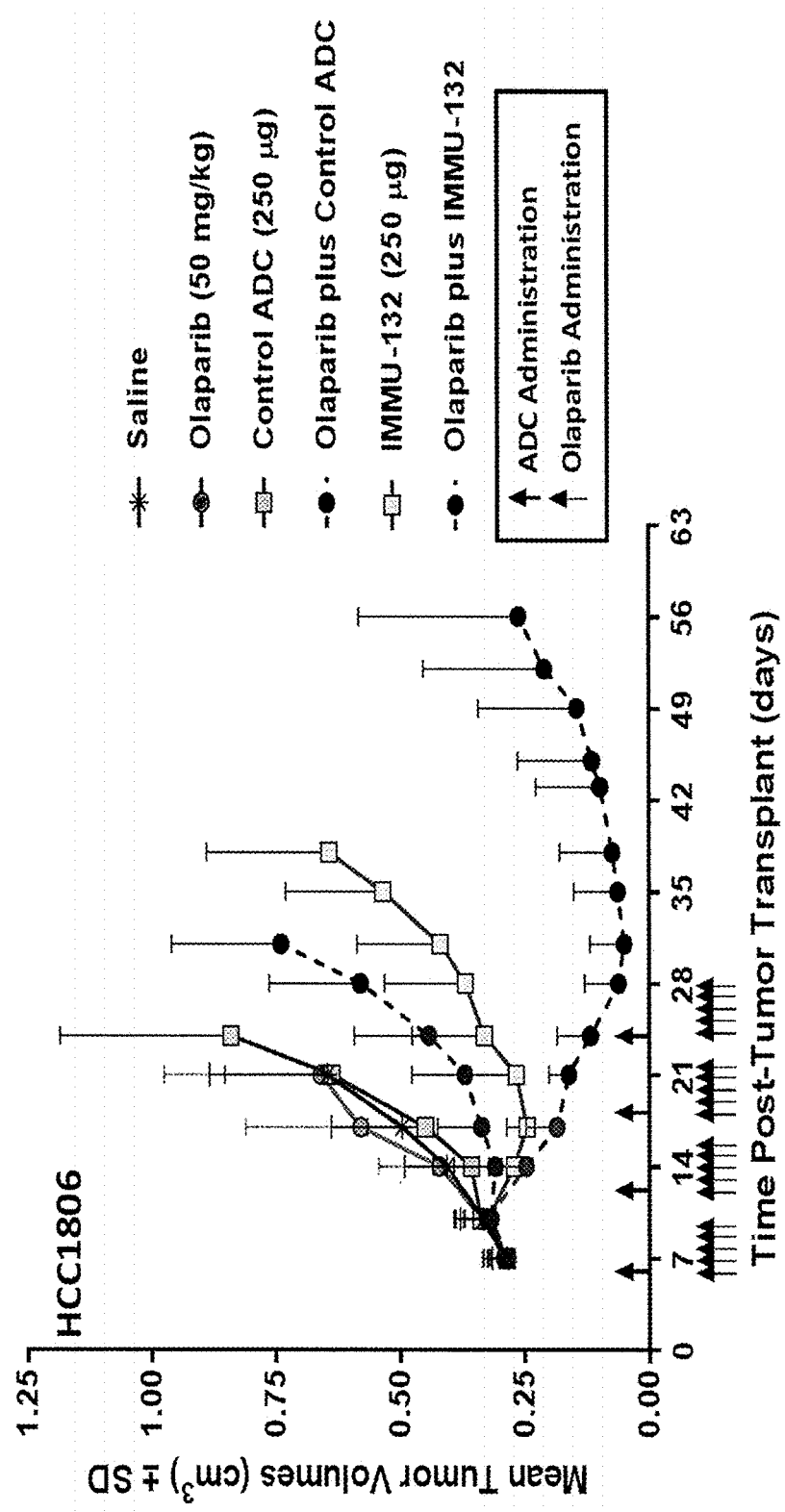
FIG. 3A. Therapeutic efficacy of IMMU-132 plus PARPi in BRCA1/2-deficient and -wild-type TNBC tumor-xenograft disease models. Tumors were established and disease end-points are described in Example 1. All the ADCs and controls were administered in the amounts indicated (lower arrows=PARPi injections, upper arrows=ADC injections). Mice bearing HCC1806 tumors (N=9-10) were injected with IMMU-132 weekly for 4 weeks and with olaparib daily (Monday through Friday) for 4 weeks. All IMMU-132 and control ADC injections were administered as i.v. Olaparib was administered i.p.
Figure 3B:
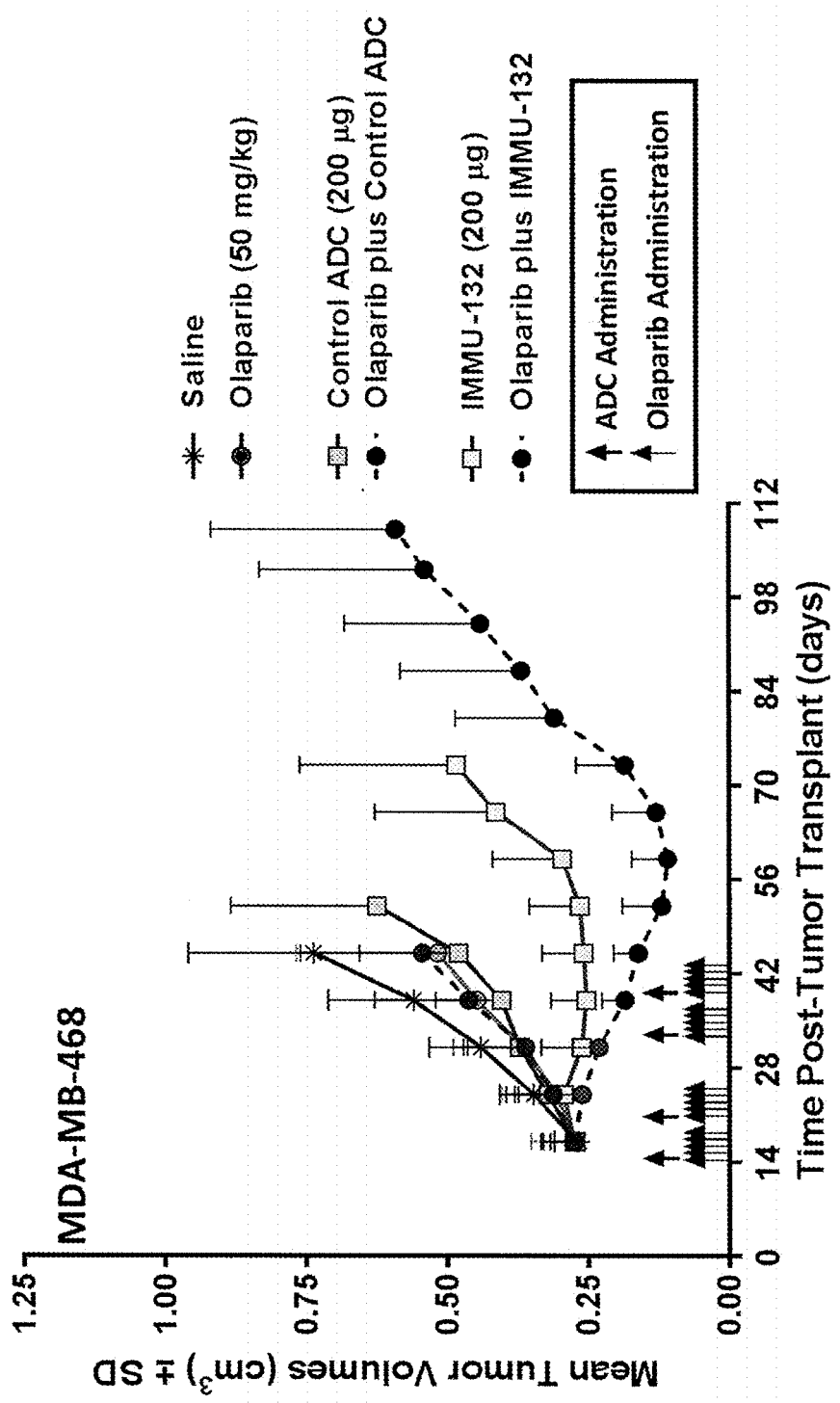
FIG. 3B. Therapeutic efficacy of IMMU-132 plus PARPi in BRCA1/2-deficient and -wild-type TNBC tumor-xenograft disease models. Tumors were established and disease end-points are described in Example 1. All the ADCs and controls were administered in the amounts indicated (lower arrows=PARPi injections, upper arrows=ADC injections). MDA-MB-468 tumor-bearing mice (N=9-10) were injected weekly with IMMU-132 for two weeks with one week off before repeating. Likewise, olaparib was administered daily (M-F) for two weeks with one week off before repeating. All IMMU-132 and control ADC injections were administered as i.v. Olaparib was administered i.p.
Figure 3C:
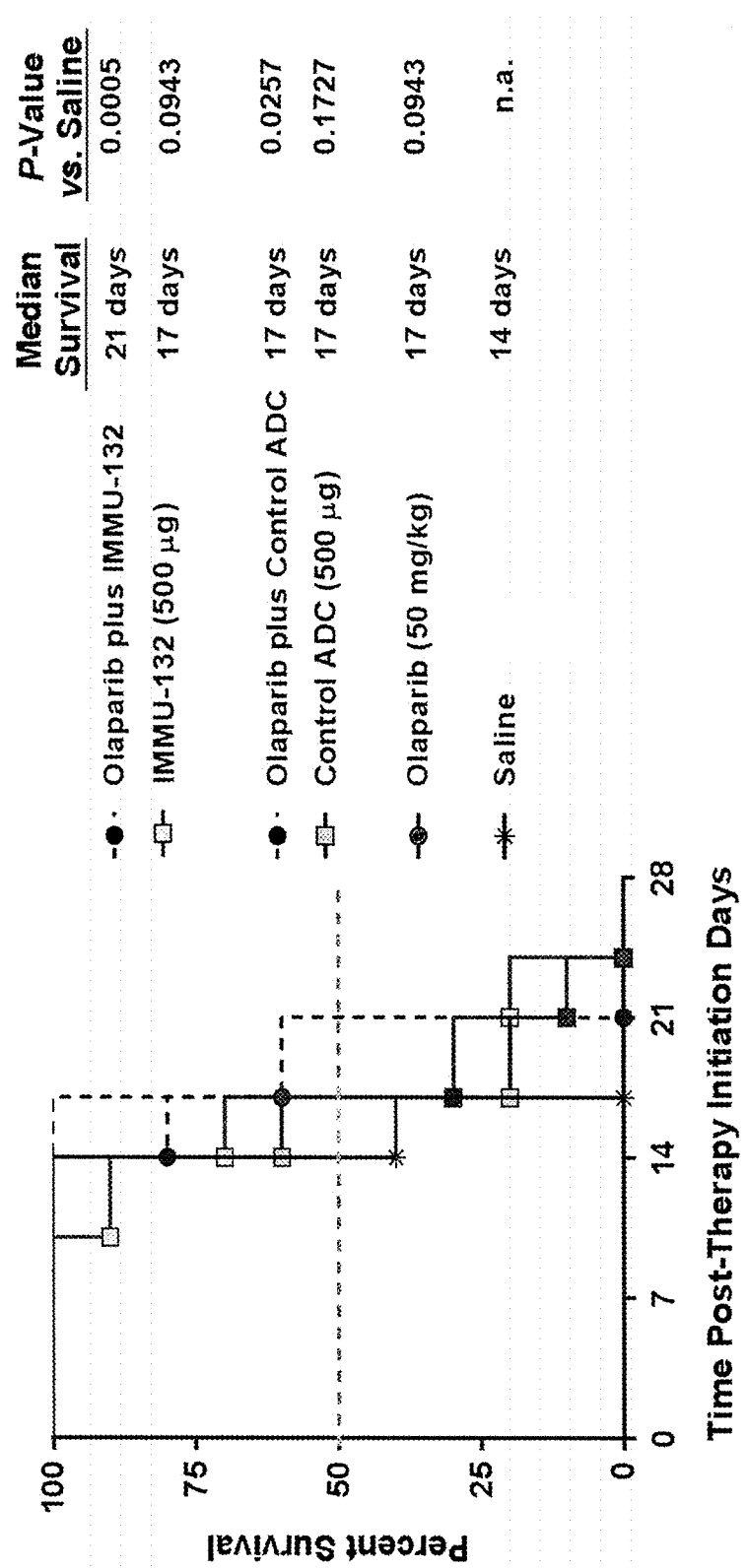
FIG. 3C. Survival curves for mice with human TNBC xenografts treated with IMMU-132 and/or olaparib. Tumors were established and disease end-points are described in Example 1. Mice bearing MDA-MB-231 tumors (N=10) were treated with IMMU-132 and olaparib under the same schedule as the HCC1806 mice.

Given the ability of IMMU-132 and olaparib to improve efficacy significantly compared to single-agent therapy in MDA-MB-468 tumors, which carry wild-type BRCA1/2, another therapy study utilized mice bearing MDA-MB-231 tumors that likewise are wild-type for BRCA1/2, but demonstrated synergy when IMMU-132 and PARPi were combined in vitro. Olaparib alone had no anti-tumor effects in mice bearing MDA-MB-231 tumors, with median survival no different than saline control mice (FIG. 3C). Not unexpectedly, IMMU-132 alone did not significantly improve the overall survival of the treated animals, since the cell line was shown previously to be resistant to this therapy (Goldenberg et al., Oncotarget 2015, 6:22496-512). However, when mice were treated with the combination of IMMU-132 plus olaparib, there was a significant increase in median survival from 14 to 21 days (P=0.0005) (FIG. 3C). These results show, unexpectedly, that even in tumors resistant to PARPi and IMMU-132 monotherapies, the combination is able to overcome this resistance and impart a survival benefit.

Figure 3D:
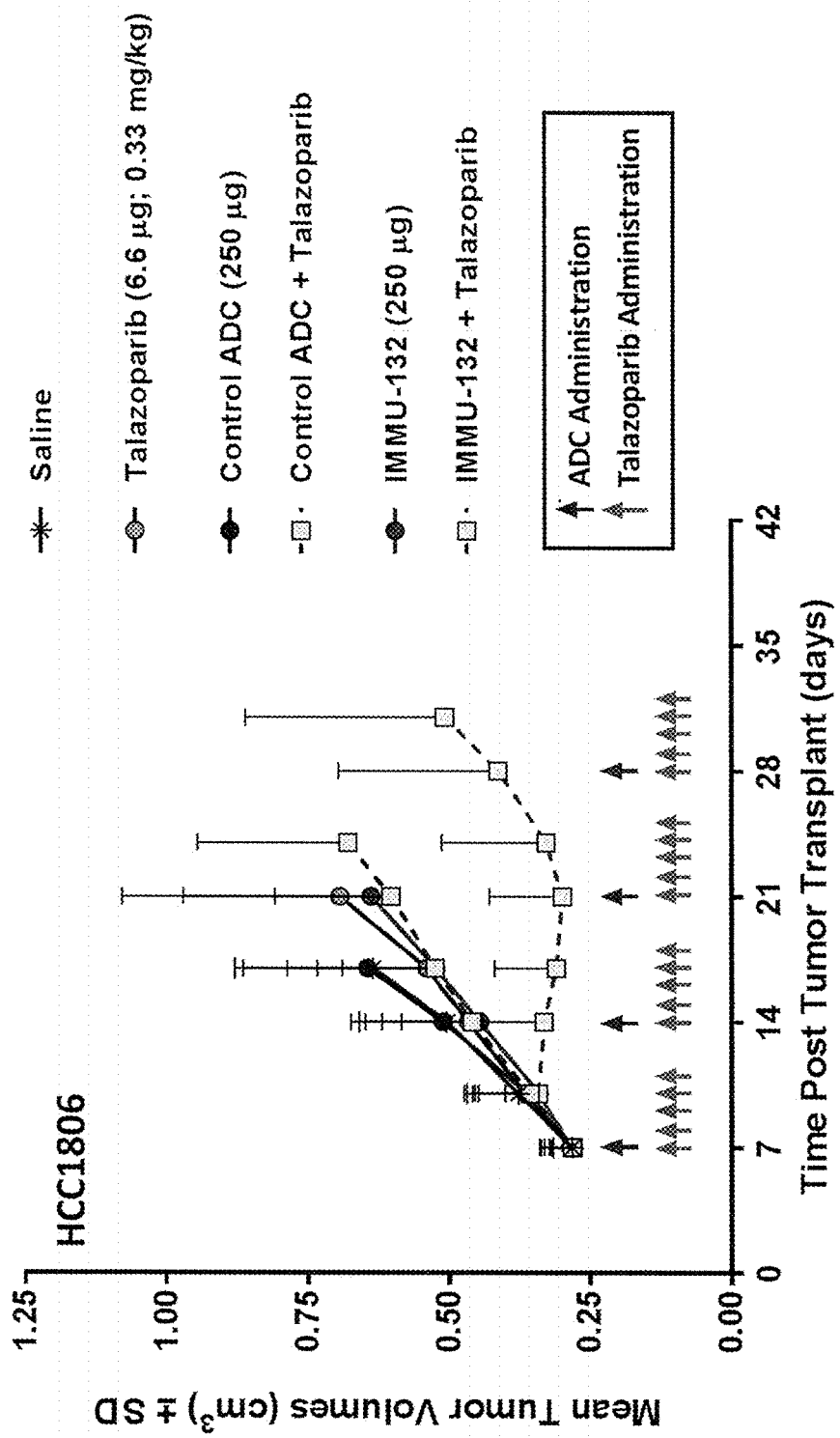
FIG. 3D. Therapeutic efficacy of IMMU-132 plus PARPi in BRCA1/2-deficient and -wild-type TNBC tumor-xenograft disease models. Tumors were established and disease end-points are described in Example 1. All the ADCs and controls were administered in the amounts indicated (lower arrows=PARPi injections, upper arrows=ADC injections). Mice bearing HCC1806 tumors (N=9-10) were treated with IMMMU-132 weekly for four weeks and talazoparib daily (M-F) for 4 weeks. All IMMU-132 and control ADC injections were administered as i.v. Talazoparib was administered p.o.

Since talazoparib's potency was greater than olaparib in vitro, both alone and when combined with IMMU-132, mice bearing HCC1806 tumors were treated with the combination of IMMU-132 and talazoparib (FIG. 3D). Whereas mice in the olaparib experiments were treated with 50 mg/kg, talazoparib-treated animals were given only 0.33 mg/kg. As observed in the olaparib experiments, IMMU-132 plus talazoparib had a significant anti-tumor effect when compared to all other treatments, including monotherapy with IMMU-132 or talazoparib (P<0.0088, AUC) (FIG. 3D). Mean TTP

TABLE 2

Time to tumor progression for TNBC tumor-bearing mice treated with IMMU-132 plus olaparib.

| | HCC1806 | | | | MDA-MB-468 | | | |
| --- | --- | --- | --- | --- | --- | --- | --- | --- |
| Treatment | N | % PR (TF) | TTP (days) | Combination vs. Controls (P-value) | N | % PR (TF) | TTP (days) | Combination vs. Controls (P-value) |
| IMMU-132 plus Olaparib | 10 | 100 (3) | 36.9 ± 8.1 | N.A. | 10 | 100 (1) | 55.2 ± 6.5 | N.A. |
| Control ADC plus Olaparib | 10 | 0 (0) | 12.1 ± 5.8 | <0.0001 | 10 | 20 (2) | 16.6 ± 14.0 | <0.0001 |
| IMMU-132 | 9* | 22 (0) | 17.6 ± 3.9 | <0.0001 | 10 | 30 (1) | 45.1 ± 13.6 | 0.0604 |
| Olaparib | 9* | 11 (0) | 9.1 ± 4.8 | <0.0001 | 10 | 20 (2) | 10.5 ± 3.7 | <0.0001 |
| Control ADC | 10 | 0 (0) | 6.3 ± 4.5 | <0.0001 | 10 | 0 (0) | 20.3 ± 20.7 | 0.0004 |
| Saline | 10 | 0 (0) | 7.7 ± 5.0 | <0.0001 | 9* | 0 (0) | 8.6 ± 3.1 | <0.0001 |

N = Number of mice per group.
% PR = Percent of mice that exhibited a partial response to treatment.
TF = Number of mice tumor-free when experiment ended.
TTP = Time to Tumor Progression for mice not tumor-free.
N.A. = Not Applicable.
*One animal in the group was deemed an outlier.

was 21.8±9.6 days, which was >2.8-fold longer than any of the other treatment groups (P<0.0021, Table 3). Similar to the combinations with olaparib, IMMU-132 plus talazoparib did not result in any observable toxicity in the mice (not shown).

TABLE 3

Time to tumor progression for HCC1806 tumor-bearing mice treated with IMMU-132 plus talazoparib

| Treatment | N | TTP (days) | Combination vs. Control (P-value) |
|---|---|---|---|
| IMMU-132 + Talazoparib | 10 | 21.8 ± 9.6 | N.A. |
| Control ADC + Talazoparib | 10 | 6.8 ± 5.4 | 0.0004 |
| IMMU-132 | 9* | 7.9 ± 6.6 | 0.0021 |
| Talazoparib | 9* | 5.9 ± 5.9 | 0.0005 |
| Control ADC | 10 | 4.6 ± 2.1 | 0.0003 |
| Saline | 10 | 4.2 ± 1.9 | 0.0001 |

N = Number of mice per groups.
TTP = Time to Tumor Progression.
N.A. = Not Applicable.
*One animal in the group was deemed an outlier.

Figure 4:
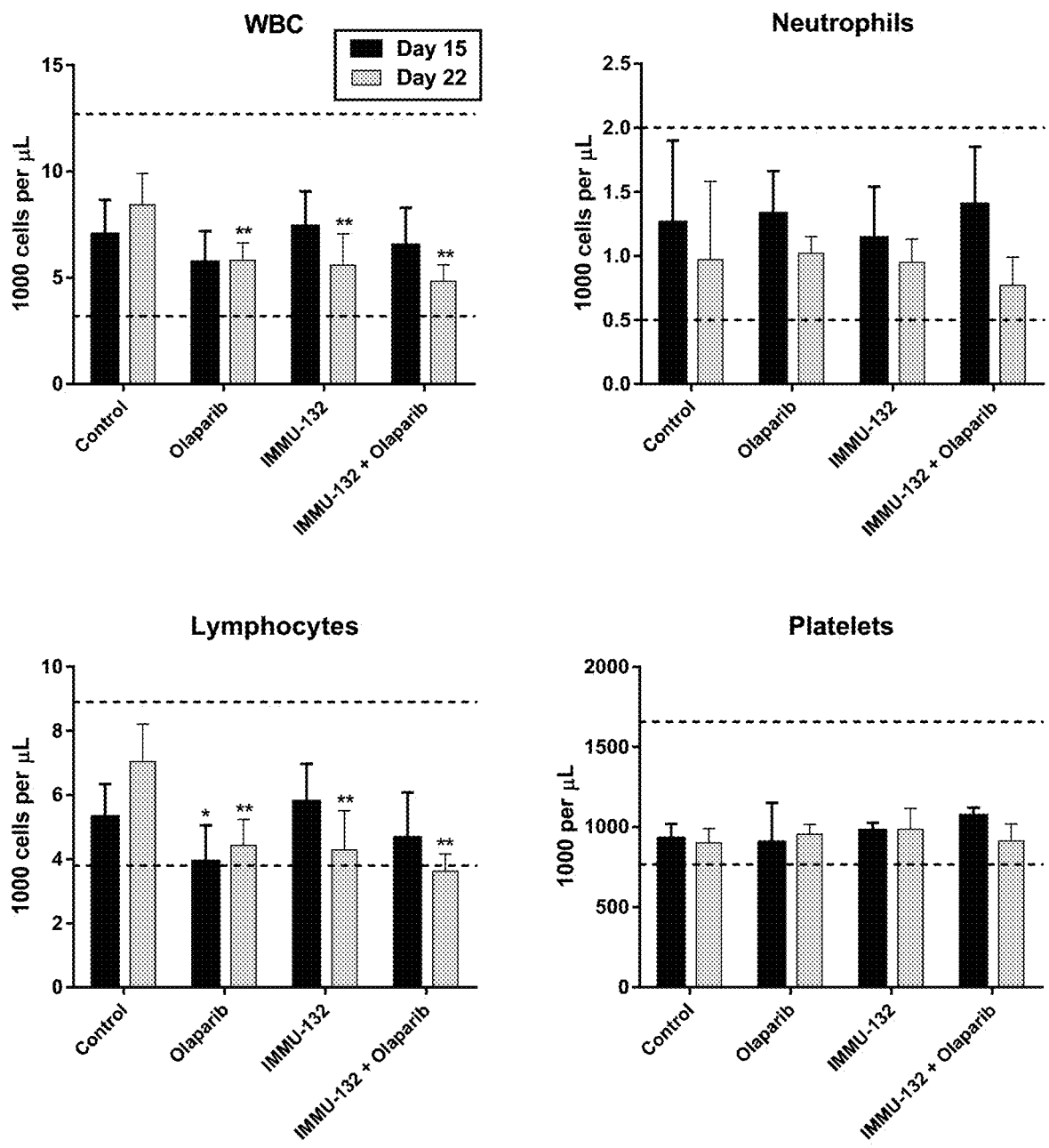
FIG. 4. Tolerability of IMMU-132 plus olaparib in naive BALB/c mice. Female BALB/c mice were placed into four different treatment groups and administered IMMU-132 (250 μg), olaparib (50 mg/kg), or both. Control mice receive only saline and olaparib diluent on the same schedule as IMMU-132 and olaparib, respectively. Whole blood was removed from five mice on day 15 (7 days post-final IMMU-132 injection and 3 days post-final olaparib injection) and five mice on day 22 (14 days post-final IMMU-132 injection and 10 days post-final olaparib injection) for automated CBC determinations. Dotted lines represent upper and lower end of the normal range for each parameter, respectively. A one-tailed t-Test was used to assess statistical differences after an F-test to determine equality of variance. *P<0.05 versus day 15 control values. **P<0.012 versus day 22 control values.

Hematologic tolerability of IMMU-132 plus olaparib in naive BALB/c mice. Naive BALB/c mice were administered a two-week course of IMMU-132 plus olaparib therapy to ascertain any possible myelotoxicity. On day 15 (i.e., 7 days after the last IMMU-132 injection and 3 days after last dose of olaparib), there was no evidence of hematological toxicity in any of the mice (FIG. 4). In particular, the combination did not result in any significant drop in total white blood cell (WBC) or lymphocyte counts. Most importantly, there was no evidence of neutropenia or thrombocytopenia in any of these mice (FIG. 4).

At day 15, only mice treated with olaparib monotherapy demonstrated a significant drop in lymphocytes relative to vehicle control animals (P=0.0481), although the mean (3.92±1.13 K/μL) remained within the normal range (3.8 to 8.9 K/μL). After a further 7 days (i.e., day 22), the assessment of toxicity was determined in the remaining mice. At this time-point, all three treatments showed a significant drop in WBC and lymphocyte counts relative to control animals (P<0.0012) (FIG. 4). However, most of these values still remained within an acceptable range, with the lowest values found in those mice treated with the combination, which fell just below the lower end of the normal range (mean lymphocyte count of 3.62±0.54 K/μL versus 7.04±1.17 K/μL for control, P=0.003) (FIG. 4). These results indicate that the combination of IMMU-132 and olaparib, which has been shown to elicit anti-tumor effects in TNBC tumor-bearing mice, is not associated with any significant myelotoxicity, and indicates a high therapeutic window.

Discussion

Exploitation of defects to a cell's HRR pathways has gained widespread interest as a means to induce synthetic lethality in various human cancers, including TNBC (Kaelin, *Nat Rev Cancer* 2005, 5:689-98; McLornan et al. *N Engl J Med* 2014, 371:1725-35). Of particular interest are those drugs that target PARP (Lord et al. *Annu Rev Med* 2015, 66:455-70; Audeh, *Pharmgenomics Pers Med* 2014, 7:307-16). While some clinical studies have suggested that use of PARPi can provide meaningful responses, other trials have shown no significant improvements in clinical outcome (Gelmon et al. *Lancet Oncol* 2011, 12:852-61; Tutt et al. *Lancet* 2010, 376:235-44). Given these mixed results, new approaches seek to combine PARPi with other DNA-damaging agents, such as platinum-based drugs, microtubule inhibitors, or irinotecan (Delaney et al. *Clin Cancer Res* 2000, 6:2860-7; Dent et al. *Breast Cancer Res* 2013, 15:R88; Davidson et al. *Invest New Drugs* 2013, 31:461-8; Karginova et al. *Mol Cancer Ther* 2015, 14:920-30; Boerner et al. *PLoS One* 2015, 10:e0119614).

Here, we examined the effect of combining several PARPi (olaparib, rucaparib, and talazoparib) with an anti-Trop-2 Topo I-inhibiting ADC, IMMU-132. All three PARPi synergized with IMMU-132 to inhibit the growth of four human TNBC cell lines. This occurred independently of BRCA1/2 status, as evidenced by the synergistic growth-inhibition in vitro of two cell lines with wild-type BRCA1/2. IMMU-132 combined with these PARPi increased the dsDNA breaks above that observed with each single agent, and the accumulation of cells in the S-phase of the cell cycle. Most importantly, in mice bearing either a BRCA1/2-mutated TNBC tumor (HCC1806) or ones with wild-type BRCA1/2 (MDA-MB-468 and MDA-MB-231), the combination of IMMU-132 plus a PARPi resulted in significant anti-tumor effects above those observed with monotherapy. These results clearly illustrate the clinical benefit derived by combining IMMU-132 with a PARPi in TNBC.

Topo I is an enzyme utilized by the cell to allow unwinding of the DNA strand during transcription and replication (Wang, *Nat Rev Mol Cell Biol* 2002, 3-430-40). PARP-1, the most abundant of the PARP proteins, has been found to co-localize with Topo I throughout the cell cycle. However, upon DNA damage, PARP-1 dissociates from Topo I, resulting in reduced activity of this enzyme (Yung et al. *J Biol Chem* 2004, 279:39686-96). We hypothesized that by combining the Topo I inhibitor carried by IMMU-132 (i.e., SN-38) with a PARPi, there would be an accumulation of dsDNA breaks due to the inability of the remaining HRR pathways in the cell to repair this damage with high fidelity, resulting in apoptosis and cell death. Additionally, in cells lacking functional BRCA1/2 or are otherwise deficient in HRR, the more error-prone, non-homologous end-joining (NHEJ) pathway is utilized, further compromising the cell towards irreparable DNA damage and apoptosis (Plummer, *Clin Cancer Res* 2010, 16:4527-31). Others have found that in both BRCA1-wild-type and -mutated TNBC cell lines, the combination of CPT-11 (the pro-drug of SN-38) and a PARPi could result in synergistic growth-inhibition in vitro (Boerner et al. *PLoS One* 2015, 10:e0119614). However, no previous study has examined the effect of combination therapy with a camptothecin-antibody drug conjugate and PARPi.

We demonstrated herein that IMMU-132, when combined with olaparib, rucaparib, or talazoparib, mediates synergistic tumor cell growth-inhibition and increased dsDNA breaks in both BRCA1/2-mutated and -wild-type cell lines. These data confirm the ability of IMMU-132-mediated inhibition of Topo I, when combined with PARPi, to synergize growth-inhibition in human TNBC cells regardless of BRCA1/2 mutational status.

HRR pathways are more active during the late S/G2-phase of the cell cycle, whereas the more error-prone NHEJ repair pathway is most evident throughout the S-phase (Rothkamm et al. *Mol Cell Biol* 2003, 23:5706-15). Cells with HRR defects, as well as those exposed to PARPi, will arrest at $G_2$/M-phase (McCabe et al. *Cancer Res* 2006, 66:8109-15; Chuang et al. *Breast Cancer Res Treat* 2012, 134:649-59). While we found that PARPi (olaparib, rucaparib, and talazoparib) and IMMU-132 exposure resulted in small increases in the number of cells in the $G_2$/M-phase of the cell cycle, it was also evident that there was greater accumulation in the S-phase. Most importantly, the combination demonstrated an even greater percentage of cells in S-phase, with a concomitant decrease in the percentage of cells in $G_1$- and little change in the $G_2$/M-phase. Interestingly, the interaction of PARP-1 and Topo I was found to be most concentrated during the S-phase (Yung et al. *J Biol Chem* 2004, 279:39686-96). Our data are consistent with this and suggests that when using a PARPi combined with IMMU-132, we are disrupting this PARP-1/Topo 1 interaction, resulting in accumulation in the S-phase and thus towards the more error-prone NHEJ repair pathway that predominates during this phase of the cell cycle. Combining IMMU-132 therapy with a PARPi (olaparib or talazoparib) in mice bearing both BRCA1/2-mutated and -wild-type tumors demonstrated significant anti-tumor effects greater than that observed with monotherapy.

Others have demonstrated improved efficacy when a PARPi is combined with a DNA-damaging chemotherapeutic in mice bearing human TNBC xenografts (Karginova et al. *Mol Cancer Ther* 2015, 14:920-30; Boerner et al. *PLoS One* 2015, 10:e0119614). In one example, CPT-11 was used in combination with veliparib to improve the therapeutic outcome significantly in mice bearing s.c. MX-1 TNBC tumors (Boerner et al. *PLoS One* 2015, 10:e0119614). The PARPi alone had no effect on tumor growth, whereas the combination of CPT-11 and veliparib demonstrated a significantly-enhanced anti-tumor effect. It should be noted that CPT-11 is more effectively converted to its active SN-38 form in mice than in humans, and therefore similar findings would not be predictable in the clinical setting (Zamboni et al. *Clin Cancer Res* 1998, 4:743-53). However, by using IMMU-132 with its SN-38 payload attached, we are not dependent on the efficiency of pro-drug-to-drug conversion by the patient, and therefore the anti-tumor effects we observed with the combination of IMMU-132 plus PARPi are clinically-relevant.

Approximately 80% of breast cancer patients carrying hereditary BRCA1 mutations present with TNBC (Lakhani et al. *J Clin Oncol* 2002, 20:2310-18). While BRCA1/2 status is an important marker in TNBC, it is not the only one. Many other BRCA1/2-wild-type TNBCs occur as sporadic tumors that share traits with germline BRCA-mutated tumors and are termed to have BRCAness (Turner et al. *Nat Rev Cancer* 2004, 4:814-19; Lips et al. *Ann Oncol* 2011, 22:870-76). For example, analysis of germline mutations in 158 TNBC patients demonstrated that in addition to BRCA1 mutations (17% of patients), mutations of the CHEK2 checkpoint kinase 2 gene, nibrin NBN gene, and Ataxia-Telangiectasia Mutated (ATM) genes also were found (3.9%), and are themselves involved in various aspects of the HRR pathway (Domagala et al. *PLoS One* 2015, 10:e0130393; Williams et al. *Biochem Cell Biol* 2007, 85:509-20; Reinhardt and Yaffe, *Curr Opin Cell Biol* 2009, 21:245-55). Overall, the evidence suggests that besides BRCA1/2 status, many other genes contribute to the BRCAness of TNBC.

In accordance with these observations, our ability to synergize and demonstrate significantly improved efficacy in the MDA-MB-468 tumor could be explained by the PTEN mutation it carries and its loss of function. Loss of PTEN expression results in Rad51 dissociation from DNA replication forks, and subsequent destabilization and stalled replication. Cells lacking PTEN have deficient HRR functions, likely due to reduced Rad51 recruitment to the replicating DNA, culminating in loss of fidelity during DNA synthesis (He et al. *Nat Commun* 2015, 6:7620). As with BRCA1/2 mutations, cells lacking PTEN function are prone to HRR deficiencies and, subsequently, have been shown to be sensitive to PARPi (McEllin et al. *Cancer Res* 2010, 70:5457-64; Shen et al. *Clin Cancer Res* 2013, 19:5003-15). Our results demonstrate that IMMU-132 combined with a PARPi will significantly improve efficacy in both traditional BRCA1/2-defective TNBC tumors as well as in tumors demonstrating BRCAness in the form of deficiencies in other proteins involved in HRR pathways (e.g., PTEN).

Since not all TNBC tumors exhibit BRCAness, we evaluated the ability of IMMU-132 plus a PARPi to inhibit tumor growth in such tumor types. MDA-MB-231 carries no mutations to PTEN, BRCA1/2, or other known HHR proteins, and as such is expected to be resistant to PARPi treatment (Shen et al. *Clin Cancer Res* 2013, 19:5003-15). Previous in vivo studies demonstrated that mice bearing MDA-MB-231 tumor xenografts were resistant to IMMU-132 therapy (Goldenberg et al. *Oncotarget* 2015, 6:22496-512). One reason for this resistance may be over-expression of Rad51 in MDA-MB-231 (Koehn et al. *Anticancer Drugs* 2007, 18:419-25). Cells exposed to SN-38 and olaparib have been found to increase Rad51 recruitment in the HRR pathway (Tahara et al. *Mol Cancer Res* 2014, 13:1170-80). It is likely that this increased expression of Rad51 in MDA-MB-231 allows for a more efficient HRR of damaged DNA caused by IMMU-132 than would otherwise occur in cells that had low expression. A second possible reason for MDA-MB-231 resistance may be that it has low expression of Trop-2 on its surface, which could limit how much SN-38 can be delivered to the tumor by IMMU-132 (Cardillo et al. *Bioconjug Chem* 2015, 26:919-31).

When IMMU-132 and its SN-38 payload was combined with olaparib, we achieved a significant survival benefit in MDA-MB-231 tumor-bearing animals. Moreover, while the amount of SN-38 delivered by IMMU-132 alone may be insufficient to retard tumor growth, enough must accrete in the tumor so that when combined with olaparib, we are able to slow tumor progression enough to provide a survival benefit. We are currently studying various MDA-MB-231 clones that were transfected with Trop-2 to increase expression levels in order to better determine what role Trop-2 surface expression plays in a tumor's sensitivity to IMMU-132 therapy, either alone or when combined with PARPi.

In a current phase I/II clinical trial, IMMU-132 has demonstrated an objective response rate (confirmed complete response+partial response) of 31% in 58 patients with metastatic TNBC (Bardia et al. 2015 *San Antonio Breast Cancer Symposium*, San Antonio, Tex., Dec. 8-12, 2015, Abstract no. PD3-06). At the maximum tolerated dose, grade 3-4 toxicities included neutropenia, febrile neutropenia, diarrhea, fatigue, anemia, leukopenia, and dyspnea. All of these toxicities were manageable, with the incidence of severe diarrhea being less than that reported for the parental prodrug, irinotecan. Single agent olaparib toxicities include grade 3-4 fatigue and thrombocytopenia (Fong et al. *N Engl J Med* 2009, 361:123-34). In clinical studies evaluating the combination of either olaparib or veliparib with irinotecan, dose-limiting toxicities included fatigue, anorexia, diarrhea, nausea, vomiting, febrile neutropenia, neutropenia, and thrombocytopenia (Chen et al. *Invest New Drugs* 2016, 34:450-7; LoRusso et al. *Clin Cancer Res* 2016, 22:3227-37). A hallmark in these clinical trials was that the amount of irinotecan and PARPi administered was reduced below the single-agent maximum tolerated doses in order to gain acceptable tolerability.

The doses of IMMU-132 administered to mice in all our preclinical studies were chosen based on their ability to produce a minimal effect, so that we could better determine if the combinations were beneficial and therefore indicated a good therapeutic window when IMMU-132 was combined with a PARPi. Importantly, in all our combination studies, the mice tolerated both the PARPi and IMMU-132 well, with no significant loss in body weight or substantial hematologic toxicity during the course of treatment. Given such a potential for a high therapeutic window, even lower IMMU-132 dosages combined with a PARPi in this subset of breast cancer patients may achieve improved therapeutic responses without unmanageable toxicity.

In summary, through the utilization of PARPi to target TNBC and create synthetic lethality combined with Topo I inhibition mediated by IMMU-132, a synergistic growth-inhibitory outcome was achieved in human TNBC tumor lines, regardless of BRCA1/2 status. While BRCAness is an important element in this combined effect, it is not limiting. Indeed, PARPi are under investigation in a variety of cancers involving breast, ovarian, pancreatic, non-small-cell lung, gastric cancer, glioblastoma, melanoma, and others. Our results show that the combination of PARPi and IMMU-132 will broaden the range of tumors that are usually treated with the former. It is interesting that IMMU-132 targets all of these cancer types (Cardillo et al. *Bioconjug Chem* 2015, 26:919-31). However, combination studies with PARPi have been problematic because of hematological toxicity, thus requiring dose modification. The studies described here have shown tolerability for the combination in terms of hematological parameters and animal body weight, and it is expected that similarly low toxicity of combination therapy will obtain in human patients.

Example 2

Synergistic Effect of Anti-Trop-2 Antibody-Drug Conjugate (ADC) in Combination Therapy with Microtubule Inhibitors The synergistic effects of anti-Trop-2 ADC with PARP inhibitors disclosed in Example 1 above were also observed when combining anti-Trop-2 ADC with microtubule inhibitors (e.g., paclitaxel, eribulin mesylate). The person of ordinary skill will realize that the synergy observed in combination therapy with anti-Trop-2 ADC is not limited to the specific antibody, conjugated drug, or microtubule inhibitors discussed below.

Materials and Methods

The methods and materials utilized in the studies below were similar to those described in Example 1. Mice were randomized into treatment groups and therapy begun when tumor volumes were approximately 0.3 cm$^3$. Mice bearing MDA-MB-468 or HCC1806 tumors were treated with either paclitaxel (qwkly×5 wks) or eribulin mesylate (wks 1, 2, 4, & 5) alone or in combination with IMMU-132 (wks 1, 2, 4, & 5).

Drug-antibody ratio (DAR) determination. Five clinical lots of IMMU-132 were evaluated by hydrophobic interaction HPLC (HIC-HPLC), which resolved three peaks representing species with DARs of 6, 7 and 8, with the greatest fraction comprising a DAR=8 (not shown). IMMU-132 was produced consistently by this manufacturing process, with an overall DAR (DAR$_{AVE}$) of 7.60±0.03 among the five clinical lots. HIC-HPLC results were confirmed by liquid chromatography-mass spectrometry (LC-MS). The analysis showed that >99% of the 8 available sulfhydryl groups were coupled with the CL2A linker, either with or without SN-38 (not shown). There were no unsubstituted (or N-ethylmaleimide capped) heavy or light chains detected. Thus, the difference in DAR among the species results from SN-38 liberation from the linker during manufacturing and not from a lower initial substitution ratio. Once prepared and lyophilized, IMMU-132 has been stable for several years.

Results

As discussed below, treatment with IMMU-132 plus paclitaxel in HCC1806 or MDA-MB-468 tumor-bearing mice significantly inhibited tumor growth compared to monotherapy (P<0.0195 and <0.0328, respectively). IMMU-132 plus eribulin mesylate also resulted in significant tumor regressions when compared to all other treatments in these two disease models (P<0.0007 and <0.0432, respectively).

FIG. 5 shows tumor growth inhibition with combined therapy using IMMU-132 and microtubule inhibitors in human TNBC tumor xenografts. Tumor-bearing mice (TV~0.3 cm$^3$) were treated with either paclitaxel or eribulin mesylate, as indicated, either alone or with IMMU-132. IMMU-132 was administered as weekly injections for two weeks with one week off before repeating. A non-tumor-targeting anti-CD20 SN-38-ADC was used as a control ADC.

Figure 5A:
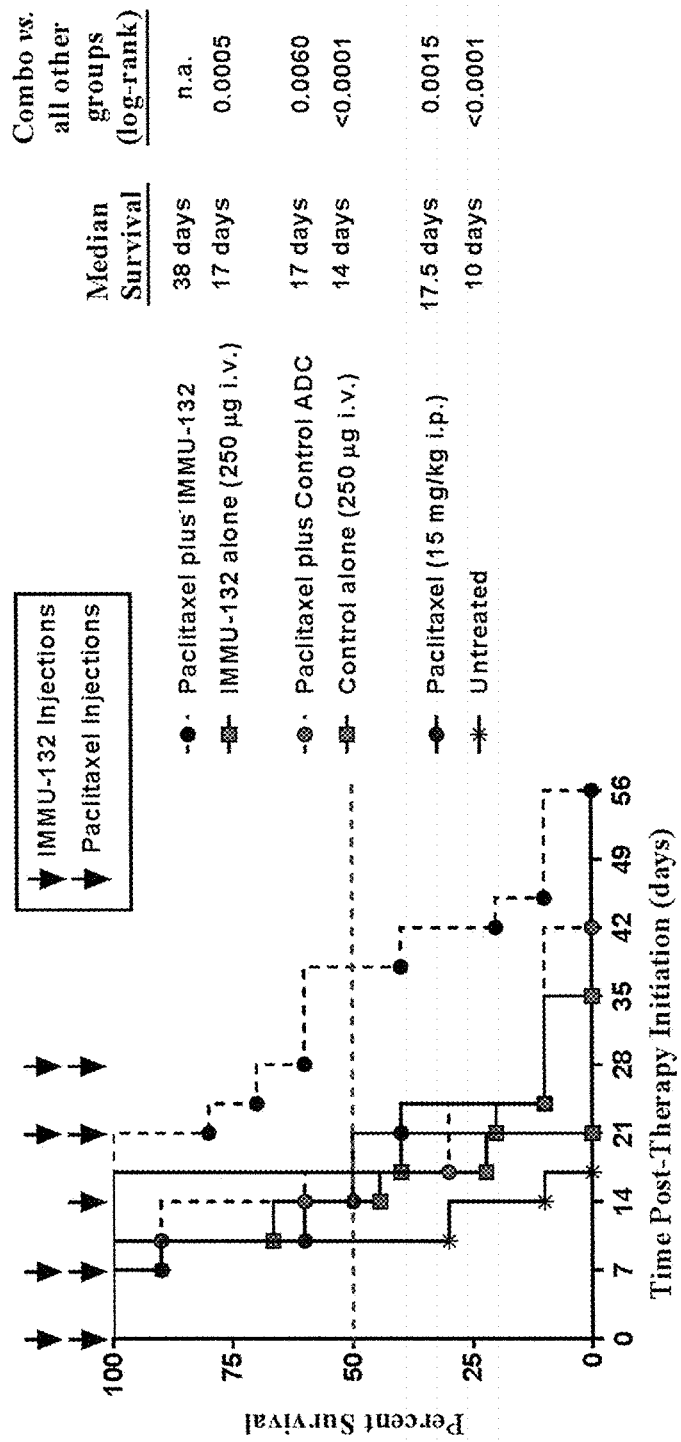
FIG. 5A. Tumor growth inhibition of combined IMMU-132 and microtubule inhibitors in human TNBC tumor xenografts. HCC1806 tumor-bearing mice treated with the combination of IMMU-132 plus paclitaxel significantly inhibited tumor growth when compared to IMMU-132 alone (P<0.0195, AUC), which translated into a significant survival benefit when compared to all other treatments (P<0.006, log-rank).
Figure 5B:
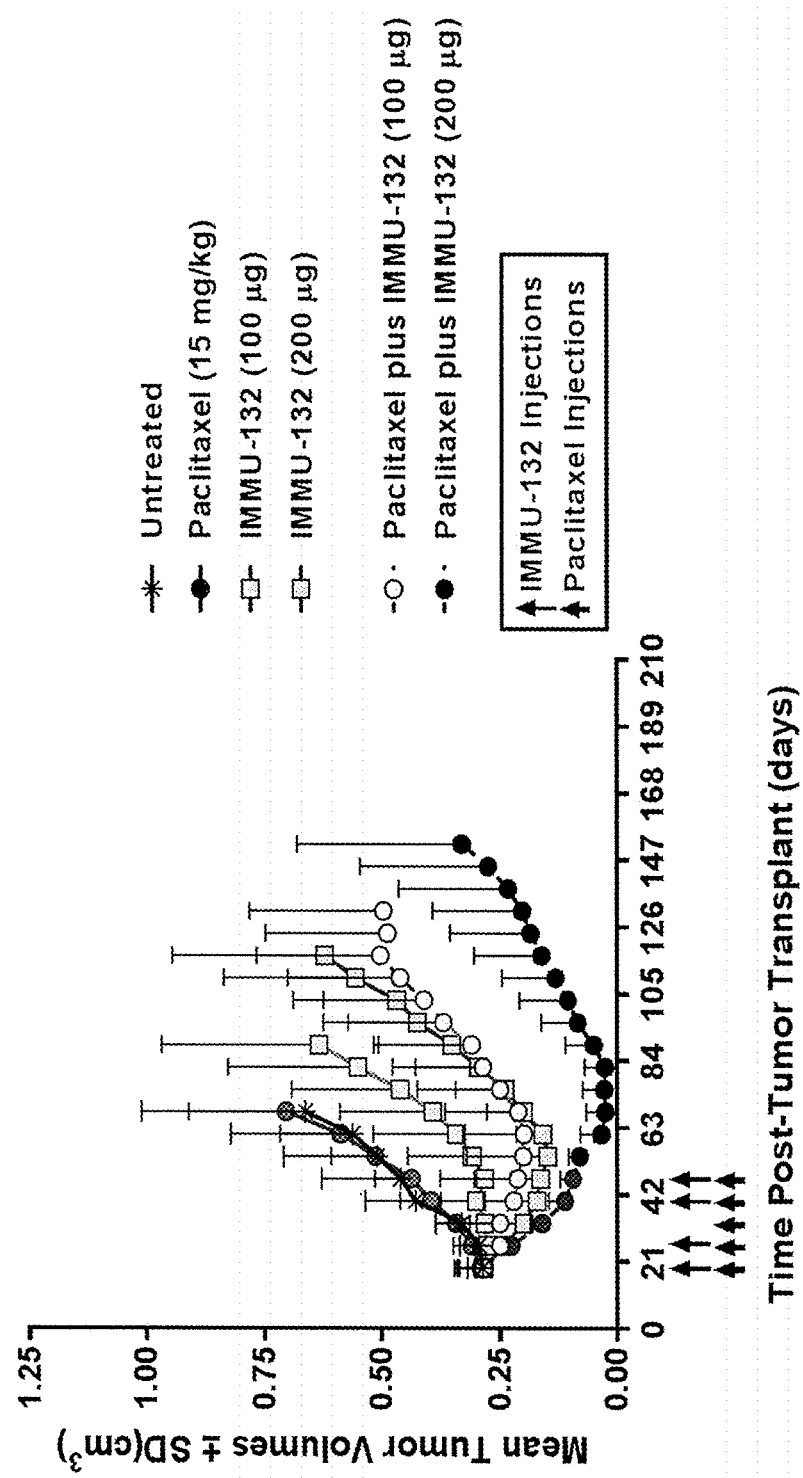
FIG. 5B. Tumor growth inhibition of combined IMMU-132 and microtubule inhibitors in human TNBC tumor xenografts. Mice bearing MDA-MB-468 tumors demonstrated significant anti-tumor effects when IMMU-132 (100 or 200 mg) was combined with paclitaxel when compared to mice receiving monotherapy (P<0.0328, AUC).

FIG. 5A shows that HCC1806 tumor-bearing mice treated with the combination of IMMU-132 plus paclitaxel demonstrated significantly inhibited tumor growth when compared to IMMU-132 alone (P<0.0195, AUC). This translated into a significant survival benefit when compared with all other treatments (P<0.006, log-rank). FIG. 5B shows that mice bearing MDA-MB-468 tumors demonstrated significant anti-tumor effects when IMMU-132 (100 or 200 mg) was combined with paclitaxel when compared to mice receiving monotherapy (P<0.0328, AUC).

Figure 5C:
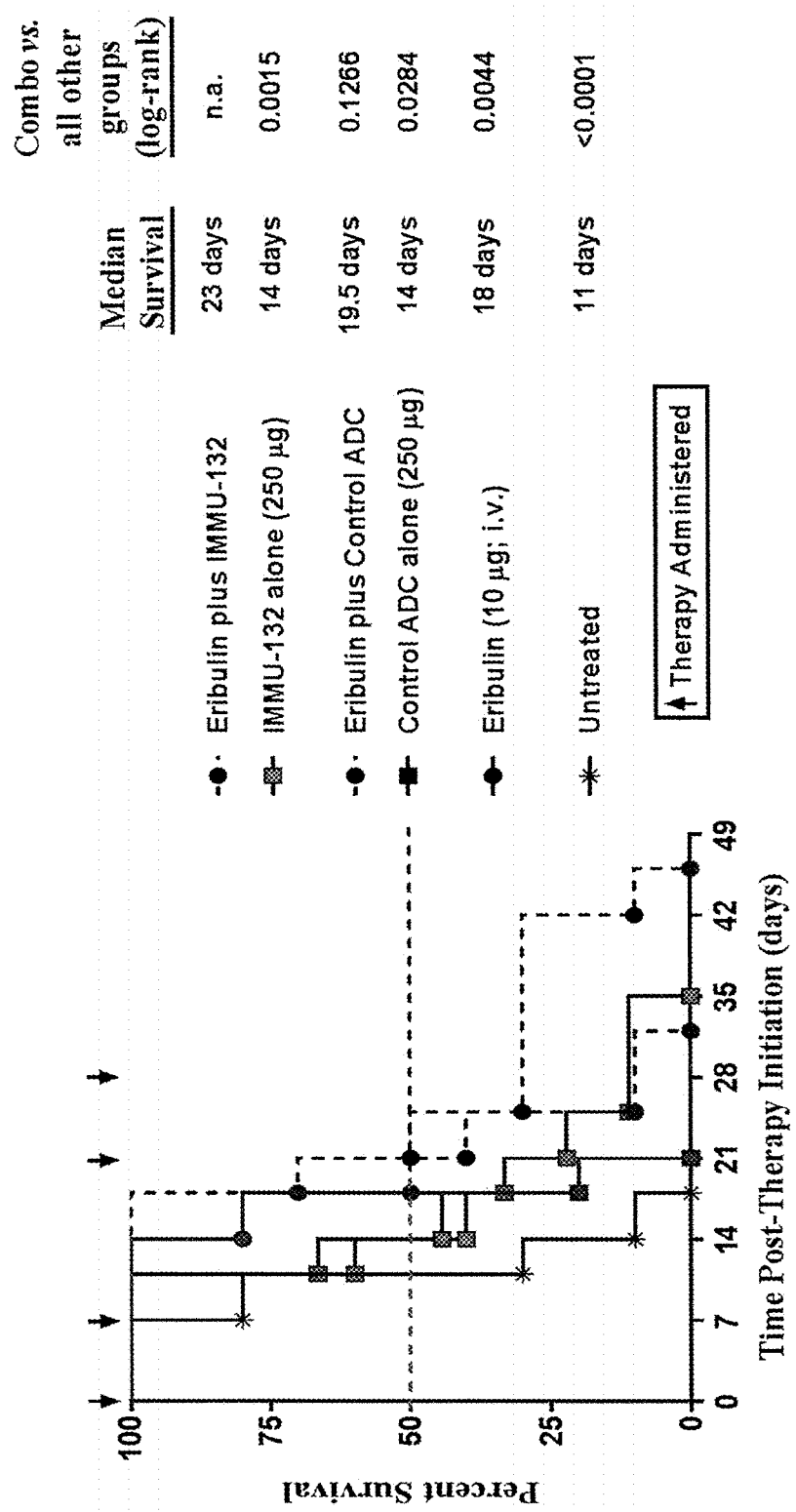
FIG. 5C. Tumor growth inhibition of combined IMMU-132 and microtubule inhibitors in human TNBC tumor xenografts. IMMU-132 plus eribulin mesylate produced significant anti-tumor effects in mice bearing the more aggressive HCC1806 tumor providing a significant survival benefit compared to all groups, except the combination of eribulin mesylate plus control ADC (P<0.0284).
Figure 5D:
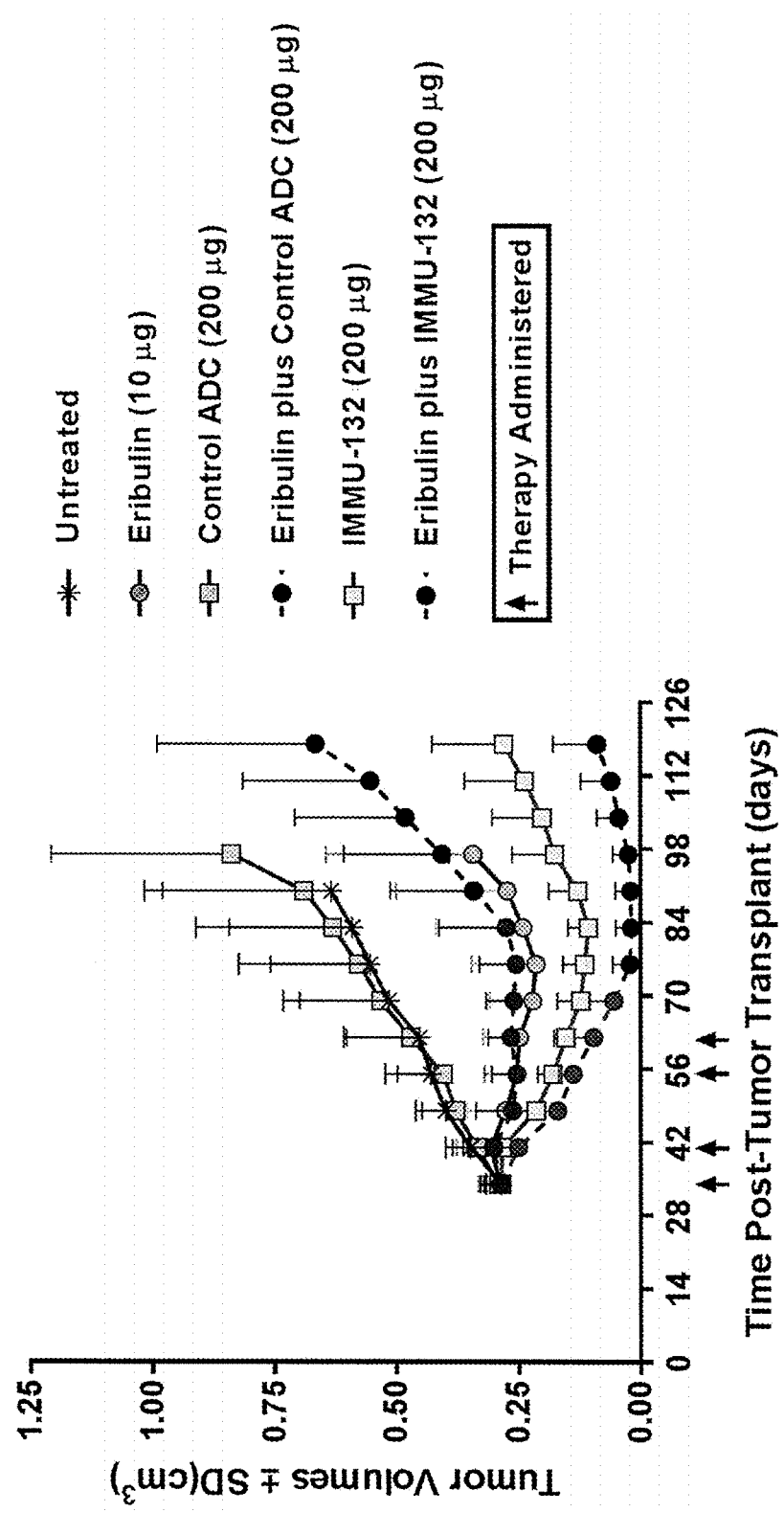
FIG. 5D. Tumor growth inhibition of combined IMMU-132 and microtubule inhibitors in human TNBC tumor xenografts. Eribulin mesylate and IMMU-132 monotherapies significantly inhibited MDA-MB-468 tumor growth when compared to untreated control mice (P<0.0019, AUC).

Using a different microtubule inhibitor, IMMU-132 plus eribulin mesylate also produced significant anti-tumor effects in mice bearing the more aggressive HCC1806 tumor, providing a significant survival benefit compared to all groups, except the combination of eribulin mesylate plus control ADC (P<0.0284) (FIG. 5C). Eribulin mesylate and IMMU-132 monotherapies significantly inhibited MDA-MB-468 tumor growth when compared to untreated control mice (P<0.0019, AUC) (FIG. 5D). Importantly, the combination of IMMU-132 plus eribulin mesylate resulted in significant tumor regressions when compared to all other treatment groups (P<0.0007 combo vs. all other therapy groups, AUC).

Figure 5E:
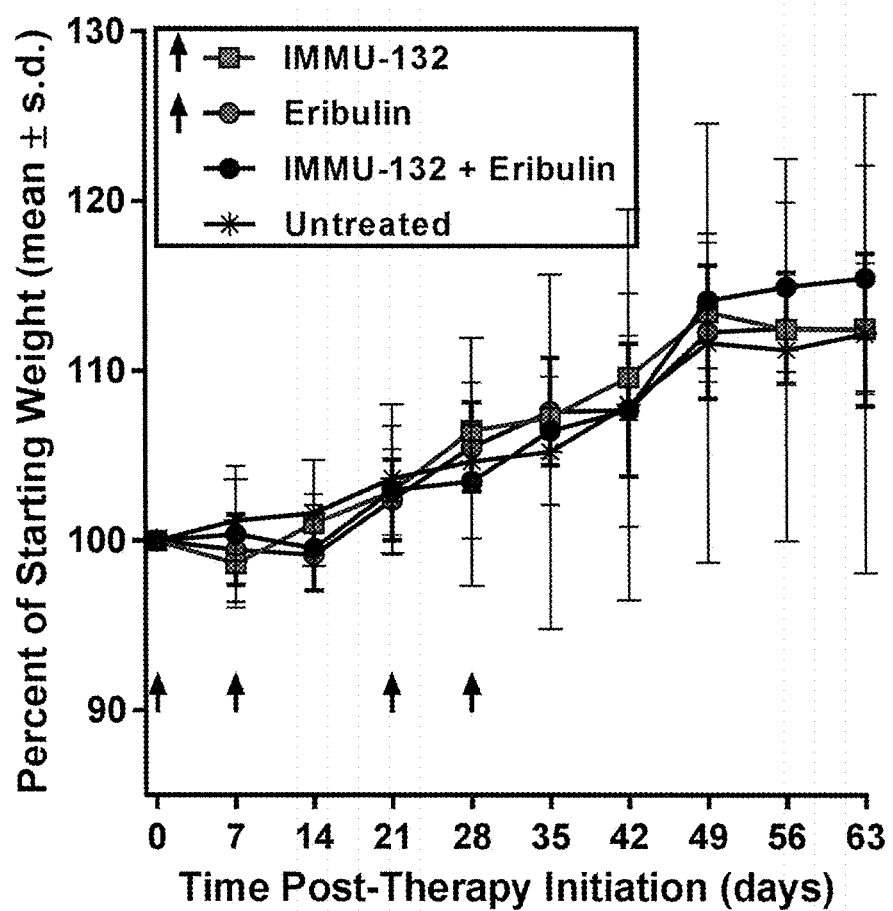
FIG. 5E. Tolerability of IMMU-132 combined with eribulin mesylate. Mice from the various therapy experiments were weighed periodically from the time therapy began on day 0. Weights for the different treatment groups are represented as the percent of starting body weight (i.e., day 0=100%). Toxicity was set at any mouse that dropped to 85% or less. These diagrams are representative of all the therapy experiments. No effect of monotherapies or combination therapy was detected on animal body weight.
Figure 5F:
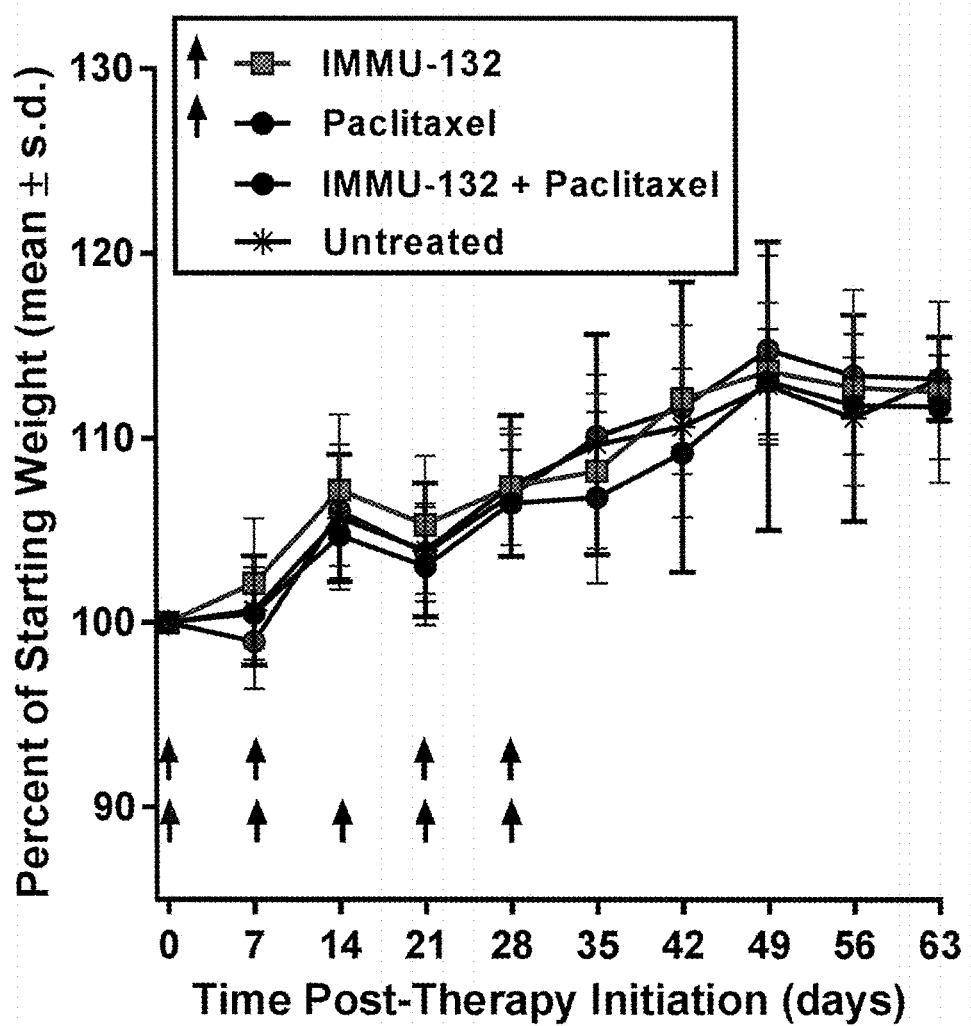
FIG. 5F. Tolerability of IMMU-132 combined with paclitaxel. Mice from the various therapy experiments were weighed periodically from the time therapy began on day 0. Weights for the different treatment groups are represented as the percent of starting body weight (i.e., day 0=100%). Toxicity was set at any mouse that dropped to 85% or less. These diagrams are representative of all the therapy experiments. No effect of monotherapies or combination therapy was detected on animal body weight.
Figure 5G:
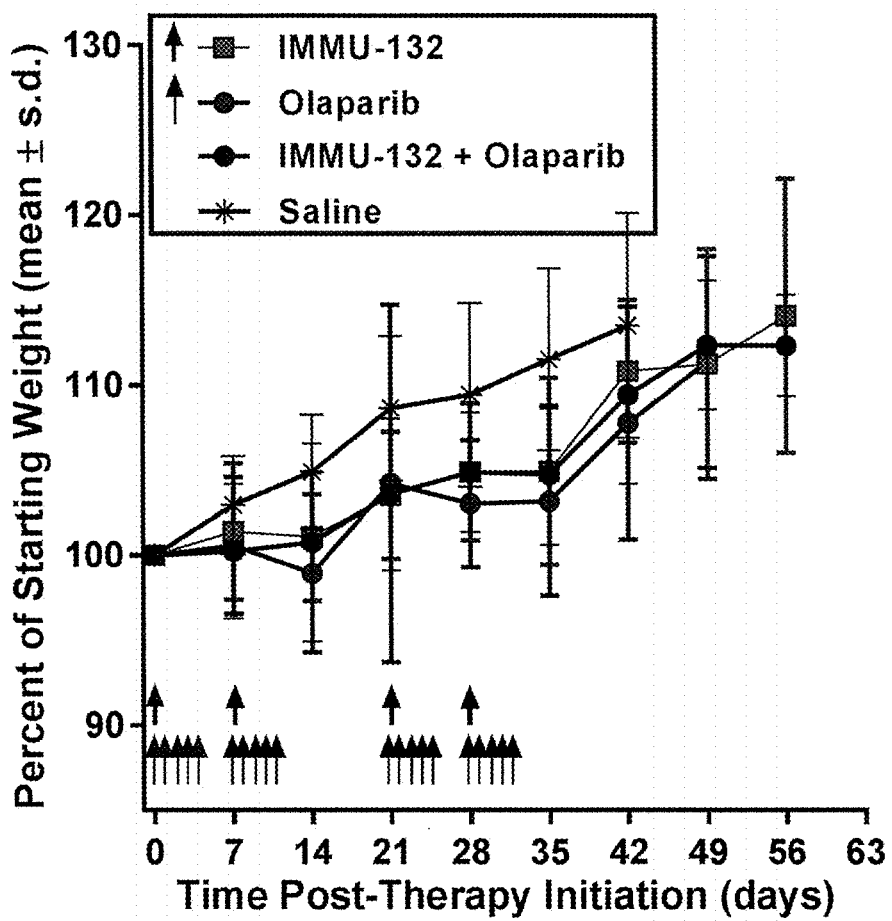
FIG. 5G. Tolerability of IMMU-132 combined with olaparib. Mice from the various therapy experiments were weighed periodically from the time therapy began on day 0. Weights for the different treatment groups are represented as the percent of starting body weight (i.e., day 0=100%). Toxicity was set at any mouse that dropped to 85% or less. These diagrams are representative of all the therapy experiments. No effect of monotherapies or combination therapy was detected on animal body weight.

FIG. 5E-5G show the tolerability of IMMU-132 combined with olaparib, paclitaxel or eribulin mesylate in athymic nu/nu nude mice. Mice from the various treatment groups were weighed periodically from the time therapy began on day 0. Weights for the different treatment groups are represented as the percent of starting body weight (i.e., day 0=100%). Toxicity was set at any mouse that dropped to 85% or less of starting body weight. These diagrams are representative of all the therapy experiments that were performed. All the IMMU-132 combinations tested proved to be very well tolerated by the mice. This includes those treated with IMMU-132 plus eribulin mesylate (FIG. 5E), IMMU-132 plus paclitaxel (FIG. 5F), and IMMU-132 plus olaparib (FIG. 5G).

Effect of DAR on pharmacokinetics and anti-tumor efficacy in mice. Mice bearing Trop-2$^+$ human gastric carcinoma xenografts (NCI-N87) were given 2 treatments 7 days apart, each with equal protein (0.5 mg) doses of IMMU-132 having DARs of 6.89, 3.28, or 1.64. Animals treated with the ADCs having a DAR of 6.89 had a significantly improved median survival time (MST) compared to mice given ADCs with either 3.38 or 1.64 DARs (MST=39 days vs. 25 and 21 days, respectively; P<0.0014) (not shown). There was no difference between groups treated with the 3.28 or 1.64 DAR conjugates and the saline control group.

To further elucidate the importance of a higher DAR, mice bearing NCI-N87 gastric tumors were administered 0.5 mg IMMU-132 with a DAR of 6.89 twice weekly for two weeks (not shown). Another group received twice the protein (1 mg) dose of an IMMU-132 conjugate with a DAR of 3.28. Although both groups received the same total amount of SN-38 (36 μg) with each dosing scheme, those treated with the 6.89 DAR conjugate inhibited tumor growth significantly more than tumor-bearing animals treated with the 3.28 DAR conjugate (P=0.0227; AUC) (not shown). Additionally, treatment with the lower DAR was not significantly different than the untreated controls. Collectively, these studies indicate that a lower DAR reduces efficacy.

An examination of the pharmacokinetic behavior of conjugates prepared at these different ratios was performed in non-tumor-bearing mice given 0.2 mg of each conjugate, unconjugated hRS7 IgG, or hRS7 IgG that was reduced and then capped with N-ethylmaleimide. Serum was taken at 5 intervals from 0.5 to 168 h and assayed by ELISA for hRS7 IgG. There was no significant difference in the clearance of these conjugates compared to the unconjugated IgG (not shown). Thus, the substitution level did not affect the pharmacokinetics of the conjugates, and equally important, the reduction of the interchain disulfide bonds did not appear to destabilize the antibody.

Delivery of SN-38 by IMMU-132 vs. irinotecan in a human tumor xenograft model. Constitutive products derived from irinotecan or IMMU-132 were determined in the serum and tumors of mice implanted s.c. with a human pancreatic cancer xenograft (Capan-1) administered irinotecan (773 μg; SN-38 equivalents=448 μg) and IMMU-132 (1.0 mg; SN-38 equivalents=16 μg). Following administration, at 5 intervals 3 animals from each group were euthanized with serum extracted for the products of interest.

Irinotecan cleared very rapidly from serum, with conversion to SN-38 and SN-38G seen within 5 min (not shown). None of the products was detected at 24 h. The AUCs over a 6-h period were 21.0, 2.5, and 2.8 μg/mL·h for irinotecan, SN-38, and SN-38G, respectively (SN-38 conversion in mice=[2.5+2.8]/21=25.2%]). Animals given IMMU-132 had much lower concentrations of free SN-38 in the serum, but it was detected through 48 h (not shown). Free SN-38G was detected only at 1 and 6 h, and was 3- to 7-times lower than free SN-38 (not shown).

In the Capan-1 tumors excised from irinotecan-treated animals, irinotecan levels were high over 6 h, but undetectable a 24 h ($AUC_{5\ min-6\ h}$=48.4 μg/g·h). SN-38 was much lower and detected only through 2 h (i.e., $AUC_{5\ min-2\ h}$=0.4 μg/g·h), with SN-38G values almost 3-fold higher (AUC=1.1 μg/g·h) (not shown). Tumors taken from animals given IMMU-132 did not have any detectable free SN-38 or SN-38G, but instead, all SN-38 in the tumor was bound to IMMU-132. Importantly, since no SN-38G was detected in the tumors, this suggests SN-38 bound to IMMU-132 was not glucuronidated. The AUC for SN-38 bound to IMMU-132 in these tumors was 54.3 μg/g·h, which is 135-fold higher than the amount of SN-38 in the tumors of animals treated with irinotecan over the 2-h period that SN-38 could be detected, even though mice given irinotecan received 28-fold more SN-38 equivalents than administered with IMMU-132 (i.e., 448 vs 16 μg SN-38 equivalents, respectively)

Conclusions

IMMU-132 is a humanized anti-Trop-2 antibody conjugated with 7.6 molecules of SN-38, the active metabolite of irinotecan, a topoisomerase I inhibitor. Clinically, IMMU-132 has shown manageable toxicity and encouraging responses in patients with relapsed/refractory TNBC (ClinicalTrials.gov, NCT01631552). IMMU-132 therapy alone demonstrated significant anti-tumor effects in human TNBC xenografts at a human equivalent dose that is 5-fold less than that being used clinically (i.e., 10 mg/kg). Since preclinical studies indicate IMMU-132 can be combined with different microtubule-inhibitors or PARP-inhibitors with significantly enhanced anti-tumor activity, these data support the use of IMMU-132 and other antibody-drug conjugates (ADCs) that cause DNA breaks, in combination with microtubule inhibitors and/or PARP inhibitors in general, as well as other chemotherapeutic agents that target cell division through microtubule inhibition or DNA-repair mechanisms. A preferred ADC class is represented by anti-Trop-2 antibody conjugates in patients with Trop-2 positive cancers, including but not limited to TNBC, metastatic colon cancer, urothelial cancer, SCLC and NSCLC, since this is a target that is expressed in high amounts in a large number of cancers, and is localized on the cell surface and cytoplasmically in the cancer cells. However, other cancer can also be targeted with this combination therapy if they are Trop-2 positive. It is also contemplated that antibodies targeting tumor-associated antigens (TAAs) other than Trop-2 may be used as ADCs in combination with microtubule inhibitors and/or PARPi.

Synergy was achieved when IMMU-132 was combined with PARP-inhibitors (e.g., olaparib) in TNBC tumor lines that had BRCA1/2 defects, as well as wild-type expression, including one with only a PTEN defect. This suggests that IMMU-132 may synergize with any tumor that has any kind of disruption in DNA homologous recombination pathways. Combined with olaparib, IMMU-132 therapy achieved significant anti-tumor effects above that observed with monotherapy with each, resulting in a significant survival benefit. IMMU-132 combined with microtubule inhibitors, (e.g., paclitaxel or eribulin mesylate) also enhanced efficacy significantly compared to monotherapy with each agent.

Overall, these data evidence the unexpected significant advantage of combination therapy with an antibody-drug conjugate (ADC) that targets cancer cells and induces DNA strand breaks, such as IMMU-132, and microtubule inhibitors or PARP inhibitors. Targeting the PARP DNA repair pathway in BRCA1/2 mutant TNBC tumors by combining IMMU-132 therapy with either paclitaxel or olaparib achieved synthetic lethality in this disease model with no observable toxicity. In an exemplary embodiment, the combination of IMMU-132 and a PARP or microtubule inhibitor is of use to treat Trop-2 positive cancers, such as TNBC. These data provide the rationale for use of IMMU-132 in combination with other chemotherapeutics that likewise target DNA-repair mechanisms in patients with TNBC or similar tumors.

Example 3

Conjugation of Bifunctional SN-38 Products to Mildly Reduced Antibodies

The anti-CEACAM5 humanized MAb, hMN-14 (also known as labetuzumab), the anti-CD22 humanized MAb, hLL2 (also known as epratuzumab), the anti-CD20 humanized MAb, hA20 (also known as veltuzumab), the anti-EGP-1 humanized MAb, hRS7, and anti-mucin humanized MAb, hPAM4 (also known as clivatuzumab), were used in these studies. Each antibody was reduced with dithiothreitol (DTT), used in a 50-to-70-fold molar excess, in 40 mM PBS, pH 7.4, containing 5.4 mM EDTA, at 37° C. (bath) for 45 min. The reduced product was purified by size-exclusion chromatography and/or diafiltration, and was buffer-exchanged into a suitable buffer at pH 6.5. The thiol content was determined by Ellman's assay, and was in the 6.5-to-8.5 SH/IgG range. Alternatively, the antibodies were reduced with Tris (2-carboxyethyl) phosphine (TCEP) in phosphate buffer at pH in the range of 5-7, followed by in situ conjugation. The reduced MAb was reacted with ~10-to-15-fold molar excess of CL2A-SN-38 (prepared as disclosed in U.S. Pat. No. 7,999,083) using DMSO at 7-15% v/v as co-solvent, and incubating for 20 min at ambient temperature. The conjugate was purified by centrifuged SEC, passage through a hydrophobic column, and finally by ultrafiltration-diafiltration. The product was assayed for SN-38 by absorbance at 366 nm and correlating with standard values, while the protein concentration was deduced from absorbance at 280 nm, corrected for spillover of SN-38 absorbance at this wavelength. This way, the SN-38/MAb substitution ratios were determined. The purified conjugates were stored as lyophilized formulations in glass vials, capped under vacuum and stored in a −20° C. freezer. SN-38 molar substitution ratios (MSR) obtained for some of these conjugates, which were typically in the 5-to-7 range, are shown in Table 4. The person of ordinary skill will realize that the conjugation method may be applied to any antibody of use in the disclosed methods.

TABLE 4

SN-38/MAb Molar substitution ratios (MSR) in some conjugates

| MAb | Conjugate | MSR |
|---|---|---|
| hMN-14 | hMN-14-CL2A-SN-38 | 6.1 |
| hRS7 | hRS7-CL2A-SN-38 | 5.8 |
| hA20 | hA20-CL2A-SN-38 | 5.8 |
| hLL2 | hLL2-CL2A-SN-38 | 5.7 |
| hPAM4 | hPAM4-CL2A-SN-38 | 5.9 |

Example 4

Figure 7:
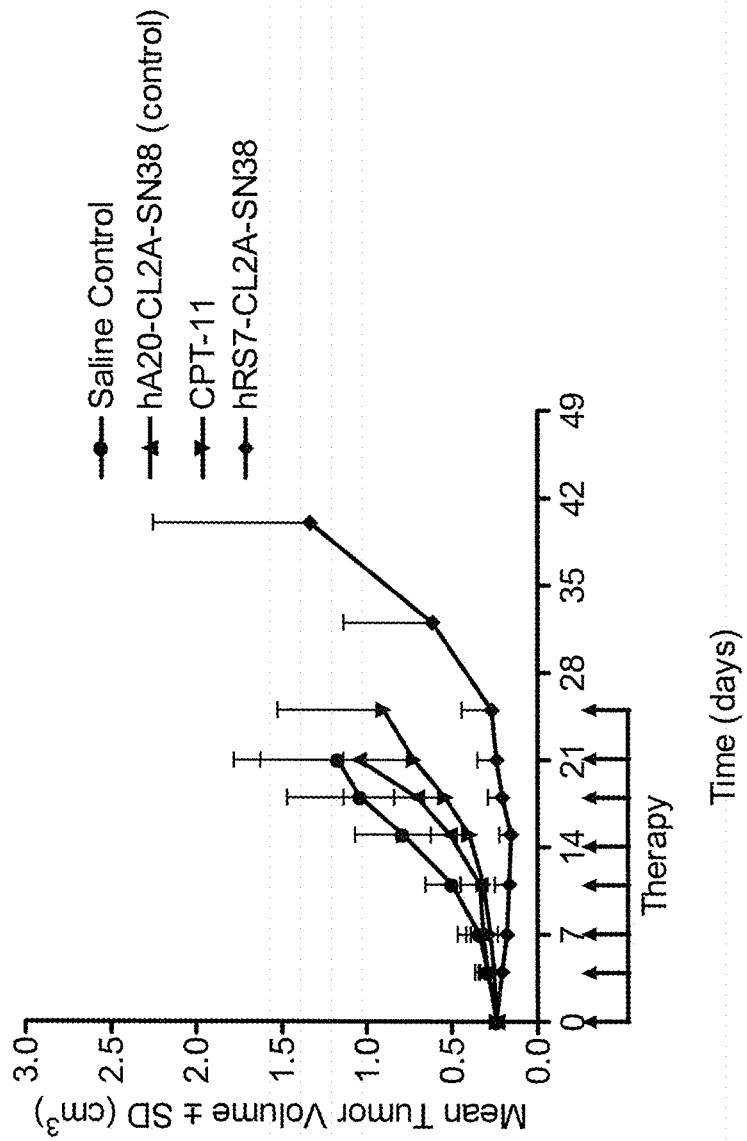
FIG. 7. In vivo therapy of athymic nude mice, bearing BxPC3 human pancreatic carcinoma, with MAb-CL2A-SN-38 conjugates.

In Vivo Therapeutic Efficacies in Preclinical Models of Human Pancreatic or Colon Carcinoma Immune-compromised athymic nude mice (female), bearing subcutaneous human pancreatic or colon tumor xenografts were treated with either specific CL2A-SN-38 conjugate or control conjugate or were left untreated. The therapeutic efficacies of the specific conjugates were observed. FIG. 6 shows a Capan 1 pancreatic tumor model, wherein specific CL2A-SN-38 conjugates of hRS7 (anti-EGP-1), hPAM4 (anti-mucin), and hMN-14 (anti-CEACAM5) antibodies showed better efficacies than control hA20-CL2A-SN-38 conjugate (anti-CD20) and untreated control. Similarly in a BXPC3 model of human pancreatic cancer, the specific hRS7-CL2A-SN-38 showed better therapeutic efficacy than control treatments (FIG. 7). Likewise, in an aggressive LS174T model of human colon carcinoma, treatment with specific hMN-14-CL2A-SN-38 was more efficacious than non-treatment (not shown).

Example 5

Use of Humanized Anti-Trop-2 IgG-SN-38 Conjugate for Effective Treatment of Diverse Epithelial Cancers Summary The purpose of this study was to evaluate the efficacy of an SN-38-anti-Trop-2 antibody-drug conjugate (ADC) against several human solid tumor types, and to assess its tolerability in mice and monkeys, the latter with tissue cross-reactivity to hRS7 similar to humans. Two SN-38 derivatives, CL2-SN-38 and CL2A-SN-38, were conjugated to the anti-Trop-2-humanized antibody, hRS7. The ADCs were characterized in vitro for stability, binding, and cytotoxicity. Efficacy was tested in five different human solid tumor-xenograft models that expressed Trop-2 antigen. Toxicity was assessed in mice and in Cynomolgus monkeys.

The hRS7 conjugates of the two SN-38 derivatives were equivalent in drug substitution (~6), cell binding ($K_d$~1.2 nmol/L), cytotoxicity ($IC_{50}$~2.2 nmol/L), and serum stability in vitro ($t_{1/2}$~20 hours). Exposure of cells to the ADC demonstrated signaling pathways leading to PARP cleavage, but differences versus free SN-38 in p53 and p21 upregulation were noted. Significant anti-tumor effects were produced by sacituzumab govitecan at nontoxic doses in mice bearing Calu-3 ($P≤0.05$), Capan-1 ($P<0.018$), BxPC-3 ($P<0.005$), and COLO 205 tumors ($P<0.033$) when compared to nontargeting control ADCs. Mice tolerated a dose of 2×12 mg/kg (SN-38 equivalents) with only short-lived elevations in ALT and AST liver enzyme levels. Cynomolgus monkeys infused with 2×0.96 mg/kg exhibited only transient decreases in blood counts, although, importantly, the values did not fall below normal ranges.

We conclude that the anti-Trop-2 hRS7-CL2A-SN-38 ADC provided significant and specific anti-tumor effects against a range of human solid tumor types. It was well tolerated in monkeys, with tissue Trop-2 expression similar to humans. (Cardillo et al., 2011, Clin Cancer Res 17:3157-69.)

Successful irinotecan treatment of patients with solid tumors has been limited due in large part to the low conversion rate of the CPT-11 prodrug into the active SN-38 metabolite. Others have examined nontargeted forms of SN-38 as a means to bypass the need for this conversion and to deliver SN-38 passively to tumors. We conjugated SN-38 covalently to a humanized anti-Trop-2 antibody, hRS7. This antibody-drug conjugate has specific anti-tumor effects in a range of s.c. human cancer xenograft models, including non-small cell lung carcinoma, pancreatic, colorectal, and squamous cell lung carcinomas, all at nontoxic doses (e.g., ≤3.2 mg/kg cumulative SN-38 equivalent dose).

Trop-2 is widely expressed in many epithelial cancers, but also some normal tissues, and therefore a dose escalation study in Cynomolgus monkeys was performed to assess the clinical safety of this conjugate. Monkeys tolerated 24 mg SN-38 equivalents/kg with only minor, reversible, toxicities. Given its tumor-targeting and safety profile, sacituzumab govitecan may provide an improvement in the management of solid tumors responsive to irinotecan.

Introduction

Human trophoblast cell-surface antigen (Trop-2), also known as GA733-1 (gastric antigen 733-1), EGP-1 (epithelial glycoprotein-1), and TACSTD2 (tumor-associated calcium signal transducer), is expressed in a variety of human carcinomas and has prognostic significance in some, being associated with more aggressive disease (see, e.g., Alberti et al., 1992, Hybridoma 11:539-45; Stein et al., 1993, Int J Cancer 55:938-46; Stein et al., 1994, Int J Cancer Suppl. 8:98-102). Studies of the functional role of Trop-2 in a mouse pancreatic cancer cell line transfected with murine Trop-2 revealed increased proliferation in low serum conditions, migration, and anchorage-independent growth in vitro, and enhanced growth rate with evidence of increased Ki-67 expression in vivo and a higher likelihood to metastasize (Cubas et al., 2010, Mol Cancer 9:253).

Trop-2 antigen's distribution in many epithelial cancers makes it an attractive therapeutic target. Stein and colleagues (1993, Int J Cancer 55:938-46) characterized an antibody, designated RS7-3G11 (RS7), that bound to EGP-1, which was present in a number of solid tumors, but the antigen was also expressed in some normal tissues, usually in a lower intensity, or in restricted regions. Targeting and therapeutic efficacies were documented in a number of human tumor xenografts using radiolabeled RS7 (Shih et al., 1995, Cancer Res 55:5857s-63s; Stein et al., 1997, Cancer 80:2636-41; Govindan et al., 2004, Breast Cancer Res Treat 84:173-82), but this internalizing antibody did not show therapeutic activity in unconjugated form (Shih et al., 1995, Cancer Res 55:5857s-63s). However, in vitro it has demonstrated antibody-dependent cellular cytotoxicity (ADCC) activity against Trop-2 positive carcinomas.

We reported the preparation of antibody-drug conjugates (ADC) using an anti-CEACAM5 (CD66e) IgG coupled to several derivatives of SN-38, a topoisomerase-I inhibitor that is the active component of irinotecan, or CPT-11 (Moon et al., 2008, J Med Chem 51:6916-26; Govindan et al., 2009, Clin Cancer Res 15:6052-61). The derivatives varied in their in vitro serum stability properties, and in vivo studies found one form (designated CL2) to be more effective in preventing or arresting the growth of human colonic and pancreatic cancer xenografts than other linkages with more or less stability.

Importantly, these effects occurred at nontoxic doses, with initial testing failing to determine a dose-limiting toxicity (Govindan et al., 2009, Clin Cancer Res 15:6052-61). These results were encouraging, but also surprising, because the CEACAM5 antibody does not internalize, a property thought to be critical to the success of an ADC. We speculated that the therapeutic activity of the anti-CEACAM5-SN-38 conjugate might be related to the slow release of SN-38 within the tumor after the antibody localized. Because irinotecan performs best when cells are exposed during the S-phase of their growth cycle, a sustained release is expected to improve responses. Indeed, SN-38 coupled to nontargeting, plasma extending agents, such as polyethylene glycol (PEG) or micelles, has shown improved efficacy over irinotecan or SN-38 alone (e.g., Koizumi et al., 2006, Cancer Res 66:10048-56), lending additional support to this mechanism.

Given the RS7 antibody's broad reactivity with epithelial cancers and its internalization ability, we hypothesized that an RS7-SN-38 conjugate could benefit not only from the sustained release of the drug, but also from direct intracellular delivery. Therefore, we prepared and tested the efficacy of SN-38 conjugates using a humanized version of the murine RS7 antibody (hRS7), wherein the SN-38 was attached to the antibody using an improved CL2A linker, which improved the quality of the conjugate and its in vivo efficacy without altering its in vitro stability. This new derivative (designated CL2A) is a preferred agent for SN-38 coupling to antibodies.

Herein, we show the efficacy of the sacituzumab govitecan (hRS7-CL2A-SN-38) conjugate in several epithelial cancer cell lines implanted in nude mice at nontoxic dosages, with other studies revealing that substantially higher doses could be tolerated. More importantly, toxicity studies in monkeys that also express Trop-2 in similar tissues as humans showed that sacituzumab govitecan was tolerated at appreciably higher amounts than the therapeutically effective dose in mice.

Materials and Methods

Cell lines, antibodies, and chemotherapeutics. All human cancer cell lines used in this study were purchased from the American Type Culture Collection. These include Calu-3 (non-small cell lung carcinoma), SK-MES-1 (squamous cell lung carcinoma), COLO 205 (colonic adenocarcinoma), Capan-1 and BxPC-3 (pancreatic adenocarcinomas), and PC-3 (prostatic adenocarcinomas). Humanized RS7 IgG and control humanized anti-CD20 (hA20 IgG, veltuzumab) and anti-CD22 (hLL2 IgG, epratuzumab) antibodies were prepared at Immunomedics, Inc. Irinotecan (20 mg/mL) was obtained from Hospira, Inc.

SN-38 ADCs and in vitro aspects. Synthesis of CL2-SN-38 has been described previously (Moon et al., 2008, J Med Chem 51:6916-26). Its conjugation to hRS7 IgG and serum stability were performed as described (Moon et al., 2008, J Med Chem 51:6916-26; Govindan et al., 2009, Clin Cancer Res 15:6052-61). Preparations of CL2A-SN-38 (M.W. 1480) and its hRS7 conjugate, and stability, binding, and cytotoxicity studies, were conducted as described previously (Moon et al., 2008, J Med Chem 51:6916-26). Cell lysates were prepared and immunoblotting for $p21^{Waf1/Cip}$, p53, and PARP (poly-ADP-ribose polymerase) was performed.

In vivo therapeutic studies. For all animal studies, the doses of SN-38 ADCs and irinotecan are shown in SN-38 equivalents. Based on a mean SN-38/IgG substitution ratio of 6, a dose of 500 µg ADC to a 20-g mouse (25 mg/kg) contains 0.4 mg/kg of SN-38. Irinotecan doses are likewise shown as SN-38 equivalents (i.e., 40 mg irinotecan/kg is equivalent to 24 mg/kg of SN-38). NCr female athymic nude (nu/nu) mice, 4 to 8 weeks old, and male Swiss-Webster mice, 10 weeks old, were purchased from Taconic Farms. Tolerability studies were performed in Cynomolgus monkeys (*Macaca fascicularis*; 2.5-4 kg male and female) by SNBL USA, Ltd. Animals were implanted subcutaneously with different human cancer cell lines. Tumor volume (TV) was determined by measurements in 2 dimensions using calipers, with volumes defined as: $L \times w^2/2$, where L is the longest dimension of the tumor and w is the shortest. Tumors ranged in size between 0.10 and 0.47 $cm^3$ when therapy began. Treatment regimens, dosages, and number of animals in each experiment are described in the Results. The lyophilized hRS7-CL2A-SN-38 and control ADC were reconstituted and diluted as required in sterile saline. All reagents were administered intraperitoneally (0.1 mL), except irinotecan, which was administered intravenously. The dosing regimen was influenced by our prior investigations, where the ADC was given every 4 days or twice weekly for varying lengths of time (Moon et al., 2008, J Med Chem 51:6916-26; Govindan et al., 2009, Clin Cancer Res 15:6052-61). This dosing frequency reflected a consideration of the conjugate's serum half-life in vitro, to allow a more continuous exposure to the ADC.

Statistics. Growth curves were determined as percent change in initial TV over time. Statistical analysis of tumor growth was based on area under the curve (AUC). Profiles of individual tumor growth were obtained through linear-curve modeling. An f-test was employed to determine equality of variance between groups before statistical analysis of growth curves. A 2-tailed t-test was used to assess statistical significance between the various treatment groups and controls, except for the saline control, where a 1-tailed t-test was used (significance at $P \leq 0.05$). Statistical comparisons of AUC were performed only up to the time that the first animal within a group was euthanized due to progression.

Pharmacokinetics and biodistribution. $^{111}$In-radiolabeled hRS7-CL2A-SN-38 and hRS7 IgG were injected into nude mice bearing s.c. SK-MES-1 tumors (~0.3 cm³). One group was injected intravenously with 20 µCi (250-µg protein) of ¹¹¹In-hRS7-CL2A-SN-38, whereas another group received 20 µCi (250-µg protein) of ¹¹¹In-hRS7 IgG. At various timepoints mice (5 per timepoint) were anesthetized, bled via intracardiac puncture, and then euthanized. Tumors and various tissues were removed, weighed, and counted by γ scintillation to determine the percentage injected dose per gram tissue (% ID/g). A third group was injected with 250 µg of unlabeled hRS7-CL2A-SN-38 3 days before the administration of ¹¹¹In-hRS7-CL2A-SN-38 and likewise necropsied. A 2-tailed t-test was used to compare hRS7-CL2A-SN-38 and hRS7 IgG uptake after determining equality of variance using the f-test. Pharmacokinetic analysis on blood clearance was performed using WinNonLin software (Parsight Corp.).

Tolerability in Swiss-Webster mice and Cynomolgus monkeys. Briefly, mice were sorted into 4 groups each to receive 2-mL i.p. injections of either a sodium acetate buffer control or 3 different doses of hRS7-CL2A-SN-38 (4, 8, or 12 mg/kg of SN-38) on days 0 and 3 followed by blood and serum collection, as described in Results. Cynomolgus monkeys (3 male and 3 female; 2.5-4.0 kg) were administered 2 different doses of hRS7-CL2A-SN-38. Dosages, times, and number of monkeys bled for evaluation of possible hematologic toxicities and serum chemistries are described in the Results.

Results

Stability and potency of hRS7-CL2A-SN-38. Two different linkages were used to conjugate SN-38 to hRS7 IgG. The first is termed CL2-SN-38 and has been described previously (Moon et al., 2008, J Med Chem 51:6916-26; Govindan et al., 2009, Clin Cancer Res 15:6052-61). A change was made to the synthesis of the CL2 linker in that the phenylalanine moiety was removed. This change simplified the synthesis, but did not affect the conjugation outcome (e.g., both CL2-SN-38 and CL2A-SN-38 incorporated ~6 SN-38 per IgG molecule). Side-by-side comparisons found no significant differences in serum stability, antigen binding, or in vitro cytotoxicity (not shown).

To confirm that the change in the SN-38 linker from CL2 to CL2A did not impact in vivo potency, hRS7-CL2A and hRS7-CL2-SN-38 were compared in mice bearing COLO 205 or Capan-1 tumors (not shown), using 0.4 mg or 0.2 mg/kg SN-38 twice weekly×4 weeks, respectively, and with starting tumors of 0.25 cm³ size in both studies. Both the hRS7-CL2A and CL2-SN-38 conjugates significantly inhibited tumor growth compared to untreated ($AUC_{14days}$ P<0.002 vs. saline in COLO 205 model; $AUC_{21days}$ P<0.001 vs. saline in Capan-1 model), and a nontargeting anti-CD20 control ADC, hA20-CL2A-SN-38 ($AUC_{14days}$ P<0.003 in COLO-205 model; $AUC_{35days}$: P<0.002 in Capan-1 model). At the end of the study (day 140) in the Capan-1 model, 50% of the mice treated with hRS7-CL2A-SN-38 and 40% of the hRS7-CL2-SN-38 mice were tumor-free, whereas only 20% of the hA20-ADC-treated animals had no visible sign of disease.

Mechanism of action. In vitro cytotoxicity studies demonstrated that hRS7-CL2A-SN-38 had $IC_{50}$ values in the nmol/L range against several different solid tumor lines (Table 5). The $IC_{50}$ with free SN-38 was lower than the conjugate in all cell lines. Although there was no correlation between Trop-2 expression and sensitivity to hRS7-CL2A-SN-38, the $IC_{50}$ ratio of the ADC versus free SN-38 was lower in the higher Trop-2-expressing cells, most likely reflecting the enhanced ability to internalize the drug when more antigen is present.

TABLE 5

Expression of Trop-2 and in vitro cytotoxicity of SN-38 and sacituzumab govitecan in several solid tumor lines

| | Trop-2 expression via FACS | | Cytotoxicity results | | | | |
| --- | --- | --- | --- | --- | --- | --- | --- |
| Cell line | Median fluorescence (background) | Percent positive | SN-38 $IC_{50}$ (nmol/L) | 95% CI $IC_{50}$ (nmol/L) | sacituzumab govitecan[a] $IC_{50}$ (nmol/L) | 95% CI $IC_{50}$ (nmol/L) | ADC/free SN-38 ratio |
| Calu-3 | 282.2 (4.7) | 99.6% | 7.19 | 5.77-8.95 | 9.97 | 8.12-12.25 | 1.39 |
| COLO 205 | 141.5 (4.5) | 99.5% | 1.02 | 0.66-1.57 | 1.95 | 1.26-3.01 | 1.91 |
| Capan-1 | 100.0 (5.0) | 94.2% | 3.50 | 2.17-5.65 | 6.99 | 5.02-9.72 | 2.00 |
| PC-3 | 46.2 (5.5) | 73.6% | 1.86 | 1.16-2.99 | 4.24 | 2.99-6.01 | 2.28 |
| SK-MES-1 | 44.0 (3.5) | 91.2% | 8.61 | 6.30-11.76 | 23.14 | 17.98-29.78 | 2.69 |
| BxPC-3 | 26.4 (3.1) | 98.3% | 1.44 | 1.04-2.00 | 4.03 | 3.25-4.98 | 2.80 |

[a]$IC_{50}$-value is shown as SN-38 equivalents of sacituzumab govitecan

SN-38 is known to activate several signaling pathways in cells, leading to apoptosis. Our initial studies examined the expression of 2 proteins involved in early signaling events ($p21^{Waf1/Cip1}$ and p53) and 1 late apoptotic event [cleavage of poly-ADP-ribose polymerase (PARP)] in vitro (not shown). In BxPC-3, SN-38 led to a 20-fold increase in $p21^{Waf1/Cip1}$ expression, whereas hRS7-CL2A-SN-38 resulted in only a 10-fold increase, a finding consistent with the higher activity with free SN-38 in this cell line (Table 5). However, hRS7-CL2A-SN-38 increased $p21^{Waf1/Cip1}$ expression in Calu-3 more than 2-fold over free SN-38 (not shown).

A greater disparity between hRS7-CL2A-SN-38- and free SN-38-mediated signaling events was observed in p53 expression. In both BxPC-3 and Calu-3, upregulation of p53 with free SN-38 was not evident until 48 hours, whereas hRS7-CL2A-SN-38 upregulated p53 within 24 hours (not shown). In addition, p53 expression in cells exposed to the ADC was higher in both cell lines compared to SN-38 (not shown). Interestingly, although hRS7 IgG had no appreciable effect on $p21^{Waf1/Cip1}$ expression, it did induce the upregulation of p53 in both BxPC-3 and Calu-3, but only after a 48-hour exposure. In terms of later apoptotic events, cleavage of PARP was evident in both cell lines when incubated with either SN-38 or the conjugate (not shown). The presence of the cleaved PARP was higher at 24 hours in BxPC-3, which correlates with high expression of p21 and its lower $IC_{50}$. The higher degree of cleavage with free SN-38 over the ADC was consistent with the cytotoxicity findings.

Figure 8A:
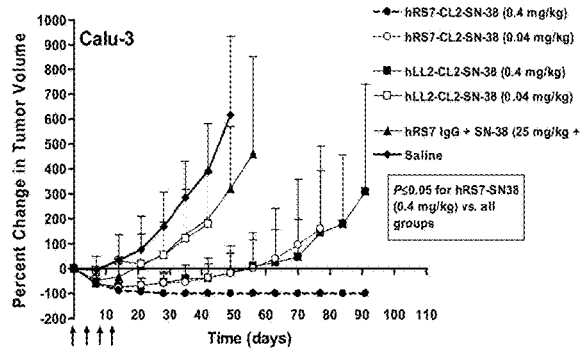
FIG. 8A. Therapeutic efficacy of sacituzumab govitecan in mice bearing human non-small cell lung tumor xenografts. Mice bearing Calu-3 tumors (N=5-7) were injected with sacituzumab govitecan every 4 days for a total of 4 injections (q4d×4). All the ADCs and controls were administered in the amounts indicated (expressed as amount of SN-38 per dose; long arrows=conjugate injections, short arrows=irinotecan injections).

Efficacy of sacituzumab govitecan. Because Trop-2 is widely expressed in several human carcinomas, studies were performed in several different human cancer models, which started with an evaluation of the hRS7-CL2-SN-38 linkage, but later, conjugates with the CL2A-linkage were used. Calu-3-bearing nude mice given 0.04 mg SN-38/kg of the hRS7-CL2-SN-38 every 4 days×4 had a significantly improved response compared to animals administered the equivalent amount of hLL2-CL2-SN-38 (TV=0.14±0.22 cm$^3$ vs. 0.80±0.91 cm$^3$, respectively; $AUC_{42days}$P<0.026; FIG. 8A). A dose-response was observed when the dose was increased to 0.4 mg/kg SN-38. At this higher dose level, all mice given the specific hRS7 conjugate were "cured" within 28 days, and remained tumor-free until the end of the study on day 147, whereas tumors regrew in animals treated with the irrelevant ADC (specific vs. irrelevant $AUC_{98days}$: P=0.05). In mice receiving the mixture of hRS7 IgG and SN-38, tumors progressed >4.5-fold by day 56 (TV=1.10±0.88 cm$^3$; $AUC_{56days}$P<0.006 vs. hRS7-CL2-SN-38).

Figure 8B:
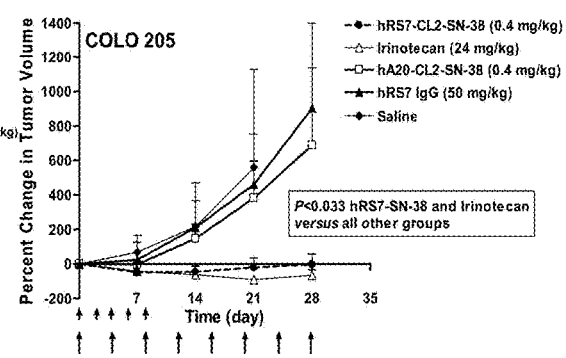
FIG. 8B. Therapeutic efficacy of sacituzumab govitecan in mice bearing human colorectal tumor xenografts. COLO 205 tumor-bearing mice (N=5) were injected 8 times (q4d×8) with the ADC or every 2 days for a total of 5 injections (q2d×5) with the MTD of irinotecan. All the ADCs and controls were administered in the amounts indicated (expressed as amount of SN-38 per dose; long arrows=conjugate injections, short arrows=irinotecan injections).

Efficacy also was examined in human colonic (COLO 205) and pancreatic (Capan-1) tumor xenografts. In COLO 205 tumor-bearing animals, (FIG. 8B), hRS7-CL2-SN-38 (0.4 mg/kg, q4d×8) prevented tumor growth over the 28-day treatment period with significantly smaller tumors compared to control anti-CD20 ADC (hA20-CL2-SN-38), or hRS7 IgG (TV=0.16±0.09 cm$^3$, 1.19±0.59 cm$^3$, and 1.77±0.93 cm$^3$, respectively; $AUC_{28days}$P<0.016). The MTD of irinotecan (24 mg SN-38/kg, q2d×5) was as effective as hRS7-CL2-SN-38, because mouse serum can more efficiently convert irinotecan to SN-38 than human serum, but the SN-38 dose in irinotecan (2,400 μg cumulative) was 37.5-fold greater than with the conjugate (64 μg total).

Figure 8C:
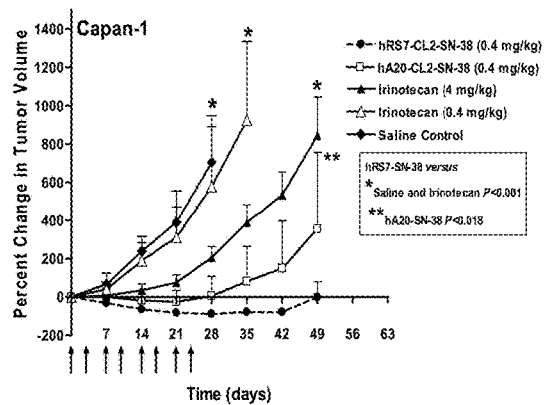
FIG. 8C. Therapeutic efficacy of sacituzumab govitecan in mice bearing human pancreatic cancer xenografts. Capan-1 (N=10) tumor-bearing mice (N=10) were treated twice weekly for 4 weeks with the agents indicated. All the ADCs and controls were administered in the amounts indicated (expressed as amount of SN-38 per dose; long arrows=conjugate injections, short arrows=irinotecan injections).

Animals bearing Capan-1 showed no significant response to irinotecan alone when given at an SN-38-dose equivalent to the hRS7-CL2-SN-38 conjugate (e.g., on day 35, average tumor size was 0.04±0.05 cm$^3$ in animals given 0.4 mg SN-38/kg sacituzumab govitecan vs. 1.78±0.62 cm$^3$ in irinotecan-treated animals given 0.4 mg/kg SN-38; $AUC_{day35}$P<0.001; FIG. 8C). When the irinotecan dose was increased 10-fold to 4 mg/kg SN-38, the response improved, but still was not as significant as the conjugate at the 0.4 mg/kg SN-38 dose level (TV=0.17±0.18 cm$^3$ vs. 1.69±0.47 cm$^3$, $AUC_{day49}$P<0.001). An equal dose of nontargeting hA20-CL2-SN-38 also had a significant anti-tumor effect as compared to irinotecan-treated animals, but the specific hRS7 conjugate was significantly better than the irrelevant ADC (TV=0.17±0.18 cm$^3$ vs. 0.80±0.68 cm$^3$, $AUC_{day49}$P<0.018).

Figure 8D:
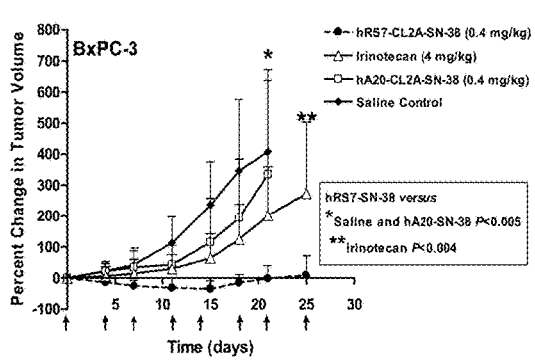
FIG. 8D. Therapeutic efficacy of sacituzumab govitecan in mice bearing human pancreatic cancer xenografts. BxPC-3 tumor-bearing mice (N=10) were treated twice weekly for 4 weeks with the agents indicated. All the ADCs and controls were administered in the amounts indicated (expressed as amount of SN-38 per dose; long arrows=conjugate injections, short arrows=irinotecan injections).
Figure 8E:
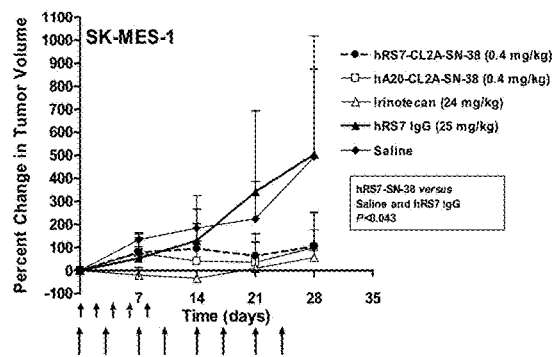
FIG. 8E. Therapeutic efficacy of sacituzumab govitecan in mice bearing human squamous cell lung carcinoma xenografts. In addition to ADC given twice weekly for 4 week, SK-MES-1 tumor-bearing (N=8) mice received the MTD of CPT-11 (q2d×5). All the ADCs and controls were administered in the amounts indicated (expressed as amount of SN-38 per dose; long arrows=conjugate injections, short arrows=irinotecan injections).

Studies with the hRS7-CL2A-SN-38 ADC were then extended to 2 other models of human epithelial cancers. In mice bearing BxPC-3 human pancreatic tumors (FIG. 8D), hRS7-CL2A-SN-38 again significantly inhibited tumor growth in comparison to control mice treated with saline or an equivalent amount of nontargeting hA20-CL2A-SN-38 (TV=0.24±0.11 cm$^3$ vs. 1.17±0.45 cm$^3$ and 1.05±0.73 cm$^3$, respectively; $AUC_{day21}$P<0.001), or irinotecan given at a 10-fold higher SN-38 equivalent dose (TV=0.27±0.18 cm$^3$ vs. 0.90±0.62 cm$^3$, respectively; $AUC_{day25}$P<0.004). Interestingly, in mice bearing SK-MES-1 human squamous cell lung tumors treated with 0.4 mg/kg of the ADC (FIG. 8E), tumor growth inhibition was superior to saline or unconjugated hRS7 IgG (TV=0.36±0.25 cm$^3$ vs. 1.02±0.70 cm$^3$ and 1.30±1.08 cm$^3$, respectively; $AUC_{28\ days}$, P<0.043), but nontargeting hA20-CL2A-SN-38 or the MTD of irinotecan provided the same anti-tumor effects as the specific sacituzumab govitecan conjugate. In all murine studies, the sacituzumab govitecan was well tolerated in terms of body weight loss (not shown).

Biodistribution of hRS7-CL2A-SN-38. The biodistributions of hRS7-CL2A-SN-38 or unconjugated hRS7 IgG were compared in mice bearing SK-MES-1 human squamous cell lung carcinoma xenografts (not shown), using the respective $^{111}$In-labeled substrates. A pharmacokinetic analysis was performed to determine the clearance of hRS7-CL2A-SN-38 relative to unconjugated hRS7 (not shown). The ADC cleared faster than the equivalent amount of unconjugated hRS7, with the ADC exhibiting ~40% shorter half-life and mean residence time. Nonetheless, this had a minimal impact on tumor uptake (not shown). Although there were significant differences at the 24- and 48-hour timepoints, by 72 hours (peak uptake) the amounts of both agents in the tumor were similar. Among the normal tissues, hepatic and splenic differences were the most striking (not shown). At 24 hours postinjection, there was >2-fold more hRS7-CL2A-SN-38 in the liver than hRS7 IgG. Conversely, in the spleen there was 3-fold more parental hRS7 IgG present at peak uptake (48-hour timepoint) than hRS7-CL2A-SN-38. Uptake and clearance in the rest of the tissues generally reflected differences in the blood concentration.

Because twice-weekly doses were given for therapy, tumor uptake in a group of animals that first received a predose of 0.2 mg/kg (250 μg protein) of the hRS7 ADC 3 days before the injection of the $^{111}$In-labeled antibody was examined. Tumor uptake of $^{111}$In-hRS7-CL2A-SN-38 in predosed mice was substantially reduced at every timepoint in comparison to animals that did not receive the predose (e.g., at 72 hours, predosed tumor uptake was 12.5%±3.8% ID/g vs. 25.4%±8.1% ID/g in animals not given the predose; P=0.0123). Predosing had no appreciable impact on blood clearance or tissue uptake (not shown). These studies suggest that in some tumor models, tumor accretion of the specific antibody can be reduced by the preceding dose(s), which likely explains why the specificity of a therapeutic response could be diminished with increasing ADC doses and why further dose escalation is not indicated.

Tolerability of hRS7-CL2A-SN-38 in Swiss-Webster mice and Cynomolgus monkeys. Swiss-Webster mice tolerated 2 doses over 3 days, each of 4, 8, and 12 mg SN-38/kg of the hRS7-CL2A-SN-38, with minimal transient weight loss (not shown). No hematopoietic toxicity occurred and serum chemistries only revealed elevated aspartate transaminase (AST) and alanine transaminase (not shown). Seven days after treatment, AST rose above normal levels (>298 U/L) in all 3 treatment groups (not shown), with the largest proportion of mice being in the 2×8 mg/kg group. However, by 15 days posttreatment, most animals were within the normal range. ALT levels were also above the normal range (>77 U/L) within 7 days of treatment (not shown) and with evidence of normalization by Day 15. Livers from all these mice did not show histologic evidence of tissue damage (not shown). In terms of renal function, only glucose and chloride levels were somewhat elevated in the treated groups. At 2×8 mg/kg, 5 of 7 mice had slightly elevated glucose levels (range of 273-320 mg/dL, upper end of normal 263 mg/dL) that returned to normal by 15 days postinjection. Similarly, chloride levels were slightly elevated, ranging from 116 to 127 mmol/L (upper end of normal range 115 mmol/L) in the 2 highest dosage groups (57% in the 2×8 mg/kg group and 100% of the mice in the 2×12 mg/kg group), and remained elevated out to 15 days postinjection. This also could be indicative of gastrointestinal toxicity, because most chloride is obtained through absorption by the gut; however, at termination, there was no histologic evidence of tissue damage in any organ system examined (not shown).

Because mice do not express Trop-2 bound by hRS7, a more suitable model was required to determine the potential of the hRS7 conjugate for clinical use. Immunohistology studies revealed binding in multiple tissues in both humans and Cynomolgus monkeys (breast, eye, gastrointestinal tract, kidney, lung, ovary, fallopian tube, pancreas, parathyroid, prostate, salivary gland, skin, thymus, thyroid, tonsil, ureter, urinary bladder, and uterus; not shown). Based on this cross-reactivity, a tolerability study was performed in monkeys.

The group receiving 2×0.96 mg SN-38/kg of hRS7-CL2A-SN-38 had no significant clinical events following the infusion and through the termination of the study. Weight loss did not exceed 7.3% and returned to acclimation weights by day 15. Transient decreases were noted in most of the blood count data (not shown), but values did not fall below normal ranges. No abnormal values were found in the serum chemistries. Histopathology of the animals necropsied on day 11 (8 days after last injection) showed microscopic changes in hematopoietic organs (thymus, mandibular and mesenteric lymph nodes, spleen, and bone marrow), gastrointestinal organs (stomach, duodenum, jejunum, ileum, cecum, colon, and rectum), female reproductive organs (ovary, uterus, and vagina), and at the injection site. These changes ranged from minimal to moderate and were fully reversed at the end of the recovery period (day 32) in all tissues, except in the thymus and gastrointestinal tract, which were trending towards full recovery at this later timepoint.

At the 2×1.92 mg SN-38/kg dose level of the conjugate, there was 1 death arising from gastrointestinal complications and bone marrow suppression, and other animals within this group showed similar, but more severe adverse events than the 2×0.96 mg/kg group. These data indicate that dose-limiting toxicities were identical to that of irinotecan; namely, intestinal and hematologic. Thus, the MTD for hRS7-CL2A-SN-38 lies between 2×0.96 and 1.92 mg SN-38/kg, which represents a human equivalent dose of 2×0.3 to 0.6 mg/kg SN-38.

Discussion

Trop-2 is a protein expressed on many epithelial tumors, including lung, breast, colorectal, pancreas, prostate, and ovarian cancers, making it a potentially important target for delivering cytotoxic agents. The RS7 antibody internalizes when bound to Trop-2 (Shih et al., 1995, Cancer Res 55:5857s-63s), which enables direct intracellular delivery of cytotoxics.

Conjugation of chemotherapeutic drugs to antibodies has been explored for over 30 years. Because a substantial portion of an ADC is not processed by the tumor, but by normal tissues, there is a risk that these agents will be too toxic to normal organ systems before reaching the therapeutic level in tumors. As with any therapeutic, the therapeutic window is a key factor determining the potential of an ADC, and thus rather than examining "ultratoxic" drugs, we chose SN-38 as the drug component of the Trop-2-targeted ADC.

SN-38 is a potent topoisomerase-I inhibitor, with $IC_{50}$ values in the nanomolar range in several cell lines. It is the active form of the prodrug, irinotecan, that is used for the treatment of colorectal cancer, and which also has activity in lung, breast, and brain cancers. We reasoned that a directly targeted SN-38, in the form of an ADC, would be a significantly improved therapeutic over CPT-11, by overcoming the latter's low and patient-variable bioconversion to active SN-38.

The Phe-Lys peptide inserted in the original CL2 derivative allowed for possible cleavage via cathepsin B. In an effort to simplify the synthetic process, in CL2A, phenylalanine was eliminated, and thus the cathepsin B cleavage site was removed. Interestingly, this product had a better-defined chromatographic profile compared to the broad profile obtained with CL2 (not shown), but more importantly, this change had no negative impact on the conjugate's binding, stability, or potency in side-by-side testing. These data suggest that SN-38 in CL2 was released from the conjugate primarily by the cleavage at the pH-sensitive benzyl carbonate bond to SN-38's lactone ring and not the cathepsin B cleavage site.

In vitro cytotoxicity of hRS7 ADC against a range of solid tumor cell lines consistently had $IC_{50}$ values in the nmol/L range. However, cells exposed to free SN-38 demonstrated a lower $IC_{50}$ value compared to the ADC. This disparity between free and conjugated SN-38 was also reported for ENZ-2208 (Sapra et al., 2008, Clin Cancer Res 14:1888-96) and NK012 (Koizumi et al., 2006, Cancer Res 66:10048-56). ENZ-2208 utilizes a branched PEG to link about 3.5 to 4 molecules of SN-38 per PEG, whereas NK012 is a micelle nanoparticle containing 20% SN-38 by weight. With our ADC, this disparity (i.e., ratio of potency with free vs. conjugated SN-38) decreased as the Trop-2 expression levels increased in the tumor cells, suggesting an advantage to targeted delivery of the drug. In terms of in vitro serum stability, both the CL2- and CL2A-SN-38 forms of sacituzumab govitecan yielded a $t_{1/2}$ of ~20 hours, which is in contrast to the short $t_{1/2}$ of 12.3 minutes reported for ENZ-2208 (Zhao et al., 2008, Bioconjug Chem 19:849-59), but similar to the 57% release of SN-38 from NK012 under physiological conditions after 24 hours (Koizumi et al., 2006, Cancer Res 66:10048-56).

Treatment of tumor-bearing mice with sacituzumab govitecan (either with CL2-SN-38 or CL2A-SN-38) significantly inhibited tumor growth in 5 different tumor models. In 4 of them, tumor regressions were observed, and in the case of Calu-3, all mice receiving the highest dose of sacituzumab govitecan were tumor-free at the conclusion of study. Unlike in humans, irinotecan is very efficiently converted to SN-38 by a plasma esterase in mice, with a greater than 50% conversion rate, and yielding higher efficacy in mice than in humans. When irinotecan was administered at 10-fold higher or equivalent SN-38 levels, sacituzumab govitecan was significantly better in controlling tumor growth. Only when irinotecan was administered at its MTD of 24 mg/kg q2d×5 (37.5-fold more SN-38) did it equal the effectiveness of sacituzumab govitecan. In patients, we would expect this advantage to favor hRS7-CL2A-SN-38 even more, because the bioconversion of irinotecan would be substantially lower.

We also showed in some antigen-expressing cell lines, such as SK-MES-1, that using an antigen-binding ADC does not guarantee better therapeutic responses than a nonbinding, irrelevant conjugate. This is not an unusual or unexpected finding. Indeed, the nonbinding SN-38 conjugates mentioned earlier enhance therapeutic activity when compared to irinotecan, and so an irrelevant IgG-SN-38 conjugate is expected to have some activity. This is related to the fact that tumors have immature, leaky vessels that allow the passage of macromolecules better than normal tissues. With our conjugate, 50% of the SN-38 will be released in ~13 hours when the pH is lowered to a level mimicking lysosomal levels (e.g., pH 5.3 at 37° C.; data not shown), whereas at the neutral pH of serum, the release rate is reduced nearly 2-fold. If an irrelevant conjugate enters an acidic tumor microenvironment, it is expected to release some SN-38 locally. Other factors, such as tumor physiology and innate sensitivities to the drug, will also play a role in defining this "baseline" activity. However, a specific conjugate with a longer residence time should have enhanced potency over this baseline response as long as there is ample antigen to capture the specific antibody. Biodistribution studies in the SK-MES-1 model also showed that if tumor antigen becomes saturated as a consequence of successive dosing, tumor uptake of the specific conjugate is reduced, which yields therapeutic results similar to that found with an irrelevant conjugate.

Although it is challenging to make direct comparisons between our ADC and the published reports of other SN-38 delivery agents, some general observations can be made. In our therapy studies, the highest individual dose was 0.4 mg/kg of SN-38. In the Calu-3 model, only 4 injections were given for a total cumulative dose of 1.6 mg/kg SN-38 or 32 µg SN-38 in a 20 g mouse. Multiple studies with ENZ-2208 were done using its MTD of 10 mg/kg×5, and preclinical studies with NK012 involved its MTD of 30 mg/kg×3. Thus, significant anti-tumor effects were obtained with sacituzumab govitecan at 30-fold and 55-fold less SN-38 equivalents than the reported doses in ENZ-2208 and NK012, respectively. Even with 10-fold less hRS7 ADC (0.04 mg/kg), significant anti-tumor effects were observed, whereas lower doses of ENZ-2208 were not presented, and when the NK012 dose was lowered 4-fold to 7.5 mg/kg, efficacy was lost (Koizumi et al., 2006, Cancer Res 66:10048-56). Normal mice showed no acute toxicity with a cumulative dose over 1 week of 24 mg/kg SN-38 (1,500 mg/kg of the conjugate), indicating that the MTD was higher. Thus, tumor-bearing animals were effectively treated with 7.5- to 15-fold lower amounts of SN-38 equivalents.

As a topoisomerase-I inhibitor, SN-38 induces significant damage to a cell's DNA, with upregulation of p53 and $p21^{WAF1/Cip1}$ resulting in caspase activation and cleavage of PARP. When we exposed BxPC-3 and Calu-3 cells to our ADC, both p53 and $p21^{WAF1/Cip1}$ were upregulated above basal levels. In addition, PARP cleavage was also evident in both cell lines, confirming an apoptotic event in these cells. Of interest was the higher upregulation of $p21^{WAF1/Cip1}$ in BxPC-3 and Calu-3 relative to p53 by both free SN-38 and our sacituzumab govitecan. This may be indicative of the mutational status of p53 in these 2 cell lines and the use of a p53-independent pathway for $p21^{WAF1/Cip1}$-mediated apoptosis.

An interesting observation was the early upregulation of p53 in both BxPC-3 and Calu-3 at 24 hours mediated by the hRS7-ADC relative to free SN-38. Even the naked hRS7 IgG could upregulate p53 in these cell lines, although only after a 48-hour exposure. Trop-2 overexpression and crosslinking by antibodies has been linked to several MAPK-related signaling events, as well as intracellular calcium release. While binding of hRS7 was not sufficient to induce apoptosis in BxPC-3 and Calu-3, as evidenced by the lack of PARP cleavage, it may be enough to prime a cell, such that the inclusion of SN-38 conjugated to hRS7 may lead to a greater effect on tumor growth inhibition. Studies are currently underway to understand which pathways are involved with hRS7-delivery of SN-38 and how they may differ from free SN-38, and what effect p53 status may play in this signaling.

Biodistribution studies revealed the hRS7-CL2A-SN-38 had similar tumor uptake as the parental hRS7 IgG, but cleared substantially faster with 2-fold higher hepatic uptake, which may be due to the hydrophobicity of SN-38. With the ADC being cleared through the liver, hepatic and gastrointestinal toxicities were expected to be dose limiting. Although mice had evidence of increased hepatic transaminases, gastrointestinal toxicity was mild at best, with only transient loss in weight and no abnormalities noted upon histopathologic examination. Interestingly, no hematological toxicity was noted. However, monkeys showed an identical toxicity profile as expected for irinotecan, with gastrointestinal and hematological toxicity being dose-limiting.

Because Trop-2 recognized by hRS7 is not expressed in mice, it was critically important to perform toxicity studies in monkeys that have a similar tissue expression of Trop-2 as humans. Monkeys tolerated 0.96 mg/kg/dose (~12 mg/m²) with mild and reversible toxicity, which extrapolates to a human dose of ~0.3 mg/kg/dose (~11 mg/m²). In a Phase I clinical trial of NK012, patients with solid tumors tolerated 28 mg/m² of SN-38 every 3 weeks with Grade 4 neutropenia as dose-limiting toxicity (Hamaguchi et al., 2010, Clin Cancer Res 16:5058-66). Similarly, Phase I clinical trials with ENZ-2208 revealed dose-limiting febrile neutropenia, with a recommendation to administer 10 mg/m² every 3 weeks or 16 mg/m² if patients were administered G-CSF. Because monkeys tolerated a cumulative human equivalent dose of 22 mg/m², it is possible that even though hRS7 binds to a number of normal tissues, the MTD for a single treatment of the hRS7 ADC could be similar to that of the other nontargeting SN-38 agents. Indeed, the specificity of the anti-Trop-2 antibody did not appear to play a role in defining the DLT, because the toxicity profile was similar to that of irinotecan. More importantly, if anti-tumor activity can be achieved in humans as in mice that responded with human equivalent dose of just at 0.03 mg SN-38 equivalents/kg/dose, then significant anti-tumor responses could be realized clinically.

In conclusion, toxicology studies in monkeys, combined with in vivo human cancer xenograft models in mice, have indicated that this ADC targeting Trop-2 is an effective therapeutic in several tumors of different epithelial origin.

Example 6

Anti-Trop-2 ADC Comprising hRS7 and Paclitaxel

A new antibody-drug conjugate (ADC) was made by conjugating paclitaxel (TAXOL®) to the hRS7 anti-human Trop-2 antibody (hRS7-paclitaxel). The final product had a mean drug to antibody substitution ratio of 2.2. This ADC was tested in vitro using two different Trop-2-positive cell lines as targets: BxPC-3 (human pancreatic adenocarcinoma) and MDA-MB-468 (human triple negative breast carcinoma). One day prior to adding the ADC, cells were harvested from tissue culture and plated into 96-well plates at 2000 cells per well. The next day cells were exposed to free paclitaxel ($6.1 \times 10^{-11}$ to $4 \times 10^{-6}$ M) or the drug-equivalent of hRS7-paclitaxel. For comparison, sacituzumab govitecan and free SN-38 were also tested at a range of $3.84 \times 10^{-12}$ to $2.5 \times 10^{-7}$ M. Plates were incubated at 37° C. for 96 h. After this incubation period, an MTS substrate was added to all of the plates and read for color development at half-hour intervals until untreated control wells had an $OD_{492\ nm}$ reading of approximately 1.0. Growth inhibition was measured as a percent of growth relative to untreated cells using Microsoft Excel and Prism software (non-linear regression to generate sigmoidal dose response curves which yield $IC_{50}$-values).

The hRS7-paclitaxel ADC exhibited cytotoxic activity in the MDA-MB-468 breast cell line (not shown), with an $IC_{50}$-value approximately 4.5-fold higher than sacituzumab govitecan. The free paclitaxel was much more potent than the free SN-38 (not shown). While the $IC_{50}$ for free SN-38 was $1.54 \times 10^{-9}$ M, the $IC_{50}$ for free paclitaxel was less than $6.1 \times 10^{-11}$ M. Similar results were obtained for the BxPC-3 pancreatic cell line (not shown) in which the hRS7-paclitaxel ADC had an $IC_{50}$-value approximately 2.8-fold higher than the sacituzumab govitecan. These results show the efficacy of anti-Trop-2 conjugated paclitaxel in vitro, with $IC_{50}$-values in the nanomolar range, similar to the sacituzumab govitecan.

Example 7

Cytotoxicity of Anti-Trop-2 ADC
(MAB650-SN-38)

A novel anti-Trop-2 ADC was made with SN-38 and MAB650, yielding a mean drug to antibody substitution ratio of 6.89. Cytotoxicity assays were performed to compare the MAB650-SN-38 and sacituzumab govitecans using two different human pancreatic adenocarcinoma cell lines (BxPC-3 and Capan-1) and a human triple negative breast carcinoma cell line (MDA-MB-468) as targets.

One day prior to adding the ADCs, cells were harvested from tissue culture and plated into 96-well plates. The next day cells were exposed to sacituzumab govitecan, MAB650-SN-38, and free SN-38 at a drug range of $3.84 \times 10^{-12}$ to $2.5 \times 10^{-7}$ M. Unconjugated MAB650 was used as a control at protein equivalent doses as the MAB650-SN-38. Plates were incubated at 37° C. for 96 h. After this incubation period, an MTS substrate was added to all of the plates and read for color development at half-hour intervals until an $OD_{492\ nm}$ of approximately 1.0 was reached for the untreated cells. Growth inhibition was measured as a percent of growth relative to untreated cells using Microsoft Excel and Prism software (non-linear regression to generate sigmoidal dose response curves which yield $IC_{50}$-values.

Sacituzumab govitecan and MAB650-SN-38 had similar growth-inhibitory effects (not shown) with $IC_{50}$-values in the low nM range which is typical for SN-38-ADCs in these cell lines. In the human Capan-1 pancreatic adenocarcinoma cell line (not shown), the sacituzumab govitecan showed an $IC_{50}$ of 3.5 nM, compared to 4.1 nM for the MAB650-SN-38 ADC and 1.0 nM for free SN-38. In the human BxPC-3 pancreatic adenocarcinoma cell line (not shown), the sacituzumab govitecan showed an $IC_{50}$ of 2.6 nM, compared to 3.0 nM for the MAB650-SN-38 ADC and 1.0 nM for free SN-38. In the human NCI-N87 gastric adenocarcinoma cell line (not shown), the sacituzumab govitecan showed an $IC_{50}$ of 3.6 nM, compared to 4.1 nM for the MAB650-SN-38 ADC and 4.3 nM for free SN-38.

In summary, in these in vitro assays, the SN-38 conjugates of two anti-Trop-2 antibodies, hRS7 and MAB650, showed equal efficacies against several tumor cell lines, which was similar to that of free SN-38. Because the targeting function of the anti-Trop-2 antibodies would be a much more significant factor in vivo than in vitro, the data support that anti-Trop-2-SN-38 ADCs as a class would be highly efficacious in vivo, as demonstrated in the Examples above for sacituzumab govitecan.

Example 8

Cytotoxicity of Anti-Trop-2 ADC (162-46.2-SN-38)

A novel anti-Trop-2 ADC was made with SN-38 and 162-46.2, yielding a drug to antibody substitution ratio of 6.14. Cytotoxicity assays were performed to compare the 162-46.2-SN-38 and sacituzumab govitecans using two different Trop-2-positive cell lines as targets, the BxPC-3 human pancreatic adenocarcinoma and the MDA-MB-468 human triple negative breast carcinoma.

One day prior to adding the ADC, cells were harvested from tissue culture and plated into 96-well plates at 2000 cells per well. The next day cells were exposed to sacituzumab govitecan, 162-46.2-SN-38, or free SN-38 at a drug range of $3.84 \times 10^{-12}$ to $2.5 \times 10^{-7}$ M. Unconjugated 162-46.2 and hRS7 were used as controls at the same protein equivalent doses as the 162-46.2-SN-38 and sacituzumab govitecan, respectively. Plates were incubated at 37° C. for 96 h. After this incubation period, an MTS substrate was added to all of the plates and read for color development at half-hour intervals until untreated control wells had an $OD_{492\ nm}$ reading of approximately 1.0. Growth inhibition was measured as a percent of growth relative to untreated cells using Microsoft Excel and Prism software (non-linear regression to generate sigmoidal dose response curves which yield $IC_{50}$-values).

The 162-46.2-SN-38 ADC had a similar $IC_{50}$-values when compared to sacituzumab govitecan (not shown). When tested against the BxPC-3 human pancreatic adenocarcinoma cell line (not shown), sacituzumab govitecan had an $IC_{50}$ of 5.8 nM, compared to 10.6 nM for 162-46.2-SN-38 and 1.6 nM for free SN-38. When tested against the MDA-MB-468 human breast adenocarcinoma cell line (not shown), sacituzumab govitecan had an $IC_{50}$ of 3.9 nM, compared to 6.1 nM for 162-46.2-SN-38 and 0.8 nM for free SN-38. The free antibodies alone showed little cytotoxicity to either Trop-2 positive cancer cell line.

In summary, comparing the efficacies in vitro of three different anti-Trop-2 antibodies conjugated to the same cytotoxic drug, all three ADCs exhibited equivalent cytotoxic effects against a variety of Trop-2 positive cancer cell lines. These data support that the class of anti-Trop-2 antibodies, incorporated into drug-conjugated ADCs, are effective anti-cancer therapeutic agents for Trop-2 expressing solid tumors.

Example 9

Clinical Trials With IMMU-132 Anti-Trop-2 ADC

Summary

The present Example reports results from a phase I clinical trial and ongoing phase II extension with IMMU-132, an ADC of the internalizing, humanized, hRS7 anti-Trop-2 antibody conjugated by a pH-sensitive linker to SN-38 (mean drug-antibody ratio=7.6). Trop-2 is a type I transmembrane, calcium-transducing, protein expressed at high density ($\sim 1 \times 10^5$), frequency, and specificity by many human carcinomas, with limited normal tissue expression. Preclinical studies in nude mice bearing Capan-1 human pancreatic tumor xenografts have revealed IMMU-132 is capable of delivering as much as 120-fold more SN-38 to tumor than derived from a maximally tolerated irinotecan therapy.

The present Example reports the initial Phase I trial of 25 patients (pts) who had failed multiple prior therapies (some including topoisomerase-I/II inhibiting drugs), and the ongoing Phase II extension now reporting on 69 pts, including in colorectal (CRC), small-cell and non-small cell lung (SCLC, NSCLC, respectively), triple-negative breast (TNBC), pancreatic (PDC), esophageal, and other cancers.

As discussed in detail below, Trop-2 was not detected in serum, but was strongly expressed ($\geq 2^+$) in most archived tumors. In a 3+3 trial design, IMMU-132 was given on days 1 and 8 in repeated 21-day cycles, starting at 8 mg/kg/dose, then 12 and 18 mg/kg before dose-limiting neutropenia. To optimize cumulative treatment with minimal delays, phase II is focusing on 8 and 10 mg/kg (n=30 and 14, respectively). In 49 pts reporting related AE at this time, neutropenia ≥G3 occurred in 28% (4% G4). Most common non-hematological toxicities initially in these pts have been fatigue (55%; ≥G3=9%), nausea (53%;≥G3=0%), diarrhea (47%; ≥G3=9%), alopecia (40%), and vomiting (32%;≥G3=2%). Homozygous UGT1A1*28/*28 was found in 6 pts, 2 of whom had more severe hematological and GI toxicities. In the Phase I and the expansion phases, there are now 48 pts (excluding PDC) who are assessable by RECIST/CT for best response. Seven (15%) of the patients had a partial response (PR), including patients with CRC (N=1), TNBC (N=2), SCLC (N=2), NSCLC (N=1), and esophageal cancers (N=1), and another 27 pts (56%) had stable disease (SD), for a total of 38 pts (79%) with disease response; 8 of 13 CT-assessable PDC pts (62%) had SD, with a median time to progression (TTP) of 12.7 wks compared to 8.0 weeks in their last prior therapy. The TTP for the remaining 48 pts is 12.6+ wks (range 6.0 to 51.4 wks). Plasma CEA and CA19-9 correlated with responses. No anti-hRS7 or anti-SN-38 antibodies were detected despite dosing over months. The conjugate cleared from the serum within 3 days, consistent with in vivo animal studies where 50% of the SN-38 was released daily, with >95% of the SN-38 in the serum being bound to the IgG in a non-glucoronidated form, and at concentrations as much as 100-fold higher than SN-38 reported in patients given irinotecan. These results show that the sacituzumab govitecan-containing ADC is therapeutically active in metastatic solid cancers, with manageable diarrhea and neutropenia.

Pharmacokinetics

Two ELISA methods were used to measure the clearance of the IgG (capture with anti-hRS7 idiotype antibody) and the intact conjugate (capture with anti-SN-38 IgG/probe with anti-hRS7 idiotype antibody). SN-38 was measured by HPLC. Total IMMU-132 fraction (intact conjugate) cleared more quickly than the IgG (not shown), reflecting known gradual release of SN-38 from the conjugate. HPLC determination of SN-38 (Unbound and TOTAL) showed >95% the SN-38 in the serum was bound to the IgG. Low concentrations of SN-38G suggest SN-38 bound to the IgG is protected from glucoronidation. Comparison of ELISA for conjugate and SN-38 HPLC revealed both overlap, suggesting the ELISA is a surrogate for monitoring SN-38 clearance.

A summary of the dosing regiment and patient poll is provided in Table 6.

TABLE 6

Clinical Trial Parameters

| | |
|---|---|
| Dosing regimen | Once weekly for 2 weeks administered every 21 days for up to 8 cycles. In the initial enrollment, the planned dose was delayed and reduced if ≥G2 treatment-related toxicity; protocol was amended to dose delay and reduction only in the event of ≥ G3 toxicity. |
| Dose level cohorts | 8, 12, 18 mg/kg; later reduced to an intermediate dose level of 10 mg/kg. |
| Cohort size | Standard Phase I [3 + 3] design; expansion includes 15 patients in select cancers. |
| DLT | G4 ANC ≥ 7 d; ≥ G3 febrile neutropenia of any duration; G4 Plt ≥ 5 d; G4 Hgb; Grade 4 N/V/D any duration/G3 N/V/D for > 48 h; G3 infusion-related reactions; related ≥ G3 non-hematological toxicity. |

TABLE 6-continued

Clinical Trial Parameters

| | |
|---|---|
| Maximum Acceptable Dose (MAD) | Maximum dose where ≥2/6 patients tolerate $1^{st}$ 21-d cycle w/o delay or reduction or ≥ G3 toxicity. |
| Patients | Metastatic colorectal, pancreas, gastric, esophageal, lung (NSCLC, SCLC), triple-negative breast (TNBC), prostate, ovarian, renal, urinary bladder, head/neck, hepatocellular. Refractory/relapsed after standard treatment regimens for metastatic cancer. Prior irinotecan-containing therapy NOT required for enrollment. No bulky lesion > 5 cm. Must be 4 weeks beyond any major surgery, and 2 weeks beyond radiation or chemotherapy regimen. Gilbert's disease or known CNS metastatic disease are excluded. |

Clinical Trial Status

A total of 69 patients (including 25 patients in Phase I) with diverse metastatic cancers having a median of 3 prior therapies were reported. Eight patients had clinical progression and withdrew before CT assessment. Thirteen CT-assessable pancreatic cancer patients were separately reported. The median TTP (time to progression) in PDC patients was 11.9 wks (range 2 to 21.4 wks) compared to median 8 wks TTP for the preceding last therapy.

A total of 48 patients with diverse cancers had at least 1 CT-assessment from which Best Response (not shown) and Time to Progression (TTP; not shown) were determined. To summarize the Best Response data, of 8 assessable patients with TNBC (triple-negative breast cancer), there were 2 PR (partial response), 4 SD (stable disease) and 2 PD (progressive disease) for a total response [PR+SD] of 6/8 (75%). For SCLC (small cell lung cancer), of 4 assessable patients there were 2 PR, 0 SD and 2 PD for a total response of 2/4 (50%). For CRC (colorectal cancer), of 18 assessable patients there were 1 PR, 11 SD and 6 PD for a total response of 12/18 (67%). For esophageal cancer, of 4 assessable patients there were 1 PR, 2 SD and 1 PD for a total response of 3/4 (75%). For NSCLC (non-small cell lung cancer), of 5 assessable patients there were 1 PR, 3 SD and 1 PD for a total response of 4/5 (80%). Over all patients treated, of 48 assessable patients there were 7 PR, 27 SD and 14 PD for a total response of 34/48 (71%). These results demonstrate that the anti-TROP-2 ADC (sacituzumab govitecan) showed significant clinical efficacy against a wide range of solid tumors in human patients.

The reported side effects of therapy (adverse events) are summarized in Table 7. As apparent from the data of Table 7, the therapeutic efficacy of sacituzumab govitecan was achieved at dosages of ADC showing an acceptably low level of adverse side effects.

TABLE 7

Related Adverse Events Listing for IMMU-132-01
Criteria: Total ≥ 10% or ≥ Grade 3

| | N = 47 patients | | |
|---|---|---|---|
| | TOTAL | Grade 3 | Grade 4 |
| Fatigue | 55% | 4 (9%) | 0 |
| Nausea | 53% | 0 | 0 |
| Diarrhea | 47% | 4 (9%) | 0 |
| Neutropenia | 43% | 11 (24%) | 2 (4%) |
| Alopecia | 40% | — | — |
| Vomiting | 32% | 1 (2%) | 0 |
| Anemia | 13% | 2 (4%) | 0 |
| Dysgeusia | 15% | 0 | 0 |
| Pyrexia | 13% | 0 | 0 |

TABLE 7-continued

Related Adverse Events Listing for IMMU-132-01
Criteria: Total ≥ 10% or ≥ Grade 3

| | N = 47 patients | | |
| --- | --- | --- | --- |
| | TOTAL | Grade 3 | Grade 4 |
| Abdominal pain | 11% | 0 | 0 |
| Hypokalemia | 11% | 1 (2%) | 0 |
| WBC Decrease | 6% | 1 (2%) | 0 |
| Febrile Neutropenia | 6% | 1 (2%) | 2 (4%) |
| Deep vein thrombosis | 2% | 1 (2%) | 0 |

Grading by CTCAE v 4.0

Exemplary partial responses to the anti-Trop-2 ADC were confirmed by CT data (not shown). As an exemplary PR in CRC, a 62 year-old woman first diagnosed with CRC underwent a primary hemicolectomy. Four months later, she had a hepatic resection for liver metastases and received 7 mos of treatment with FOLFOX and 1 mo 5FU. She presented with multiple lesions primarily in the liver (3+ Trop-2 by immunohistology), entering the sacituzumab govitecan trial at a starting dose of 8 mg/kg about 1 year after initial diagnosis. On her first CT assessment, a PR was achieved, with a 37% reduction in target lesions (not shown). The patient continued treatment, achieving a maximum reduction of 65% decrease after 10 months of treatment (not shown) with decrease in CEA from 781 ng/mL to 26.5 ng/mL, before progressing 3 months later.

As an exemplary PR in NSCLC, a 65 year-old male was diagnosed with stage IIIB NSCLC (sq. cell). Initial treatment of caboplatin/etoposide (3 mo) in concert with 7000 cGy XRT resulted in a response lasting 10 mo. He was then started on Tarceva maintenance therapy, which he continued until he was considered for IMMU-132 trial, in addition to undergoing a lumbar laminectomy. He received first dose of IMMU-132 after 5 months of Tarceva, presenting at the time with a 5.6 cm lesion in the right lung with abundant pleural effusion. He had just completed his 6$^{th}$ dose two months later when the first CT showed the primary target lesion reduced to 3.2 cm (not shown).

As an exemplary PR in SCLC, a 65 year-old woman was diagnosed with poorly differentiated SCLC. After receiving carboplatin/etoposide (Topo-II inhibitor) that ended after 2 months with no response, followed with topotecan (Topo-I inhibitor) that ended after 2 months, also with no response, she received local XRT (3000 cGy) that ended 1 month later. However, by the following month progression had continued. The patient started with IMMU-132 the next month (12 mg/kg; reduced to 6.8 mg/kg; Trop-2 expression 3+), and after two months of IMMU-132, a 38% reduction in target lesions, including a substantial reduction in the main lung lesion occurred (not shown). The patient progressed 3 months later after receiving 12 doses.

These results are significant in that they demonstrate that the anti-Trop-2 ADC was efficacious, even in patients who had failed or progressed after multiple previous therapies.

In conclusion, at the dosages used, the primary toxicity was a manageable neutropenia, with few Grade 3 toxicities. IMMU-132 showed evidence of activity (PR and durable SD) in relapsed/refractory patients with triple-negative breast cancer, small cell lung cancer, non-small cell lung cancer, colorectal cancer and esophageal cancer, including patients with a previous history of relapsing on topoisomerase-I inhibitor therapy. These results show efficacy of the anti-Trop-2 ADC in a wide range of cancers that are resistant to existing therapies.

Example 10

Use of Sacituzumab Govitecan (IMMU-132) to Treat Therapy-Refractive Metastatic Breast Cancer The patient was a 57-year-old woman with stage IV, triple-negative, breast cancer (ER/PR negative, HER-neu negative), originally diagnosed in 2005. She underwent a lumpectomy of her left breast in 2005, followed by Dose-Dense ACT in adjuvant setting in September 2005. She then received radiation therapy, which was completed in November. Local recurrence of the disease was identified when the patient palpated a lump in the contralateral (right) breast in early 2012, and was then treated with CMF (cyclophosphamide, methotrexate, 5-fluorouracil) chemotherapy. Her disease recurred in the same year, with metastatic lesions in the skin of the chest wall. She then received a carboplatin+ TAXOL® chemotherapy regimen, during which thrombocytopenia resulted. Her disease progressed and she was started on weekly doxorubicin, which was continued for 6 doses. The skin disease also was progressing. An FDG-PET scan on Sep. 26, 2012 showed progression of disease on the chest wall and enlarged, solid, axillary nodes. The patient was given oxycodone for pain control.

She was given IXEMPRA® from October 2012 until February 2013 (every 2 weeks for 4 months), when the chest wall lesion opened up and bled. She was then put on XELODA®, which was not tolerated well due to neuropathy in her hands and feet, as well as constipation. The skin lesions were progressive and then she was enrolled in the IMMU-132 trial after giving informed consent. The patient also had a medical history of hyperthyroidism and visual disturbances, with high risk of CNS disease (however, brain MRI was negative for CNS disease). At the time of enrollment to this trial, her cutaneous lesions (target) in the right breast measured 4.4 cm and 2.0 cm in the largest diameter. She had another non-target lesion in the right breast and one enlarged lymph node each in the right and left axilla.

The first IMMU-132 infusion (12 mg/kg) was started on Mar. 12, 2013, which was tolerated well. Her second infusion was delayed due to Grade 3 absolute neutrophil count (ANC) reduction (0.9) on the scheduled day of infusion, one week later. After a week delay and after receiving NEULASTA®, her second IMMU-132 was administered, with a 25% dose reduction at 9 mg/kg. Thereafter she has been receiving IMMU-132 on schedule as per protocol, once weekly for 2 weeks, then one week off. Her first response assessment on May 17, 2013, after 3 therapy cycles, showed a 43% decrease in the sum of the long diameter of the target lesions, constituting a partial response by RECIST criteria. She is continuing treatment at the 9 mg/kg dose level. Her overall health and clinical symptoms improved considerably since she started treatment with IMMU-132.

Example 11

Use of Sacituzumab Govitecan (IMMU-132) to Treat Refractory, Metastatic, Non-Small Cell Lung Cancer This is a 60-year-old man diagnosed with non-small cell lung cancer. The patient is given chemotherapy regimens of carboplatin, bevacizumab for 6 months and shows a response, and then after progressing, receives further courses of chemotherapy with carboplatin, etoposide, TAXOTERE®, gemcitabine over the next 2 years, with occasional responses lasting no more than 2 months. The patient then presents with a left mediastinal mass measuring 6.5×4 cm and pleural effusion.

After signing informed consent, the patient is given IMMU-132 at a dose of 18 mg/kg every other week. During the first two injections, brief periods of neutropenia and diarrhea are experienced, with 4 bowel movements within 4 hours, but these resolve or respond to symptomatic medications within 2 days. After a total of 6 infusions of IMMU-132, CT evaluation of the index lesion shows a 22% reduction, just below a partial response but definite tumor shrinkage. The patient continues with this therapy for another two months, when a partial response of 45% tumor shrinkage of the sum of the diameters of the index lesion is noted by CT, thus constituting a partial response by RECIST criteria.

Example 12

Use of Sacituzumab Govitecan (IMMU-132) Plus Olaparib to Treat Refractory, Metastatic, Small-Cell Lung Cancer This is a 65-year-old woman with a diagnosis of small-cell lung cancer, involving her left lung, mediastinal lymph nodes, and MRI evidence of a metastasis to the left parietal brain lobe. Prior chemotherapy includes carboplatin, etoposide, and topotecan, but with no response noted. Radiation therapy also fails to control her disease. She is then given combination therapy with IMMU-132 plus olaparib on a 21-day cycle. Olaparib is administered at 200 mg twice a day on days 1-10 of the cycle. IMMU-132 is administered at 8 mg/kg on days 1 and 8 of the cycle. After 3 cycles, there is a 31% shrinkage of sum of the longest diameters of the lung and lymph node tumors by CT, while the putative brain metastasis is no longer detected. This constitutes a PR by RECIST 1.1, because the shrinkage is confirmed 4 weeks later (35% shrinkage of the sum of all target lesions. She continues her IMMU-132 dosing every 3 weeks for another 3 months, and continues to show objective and subjective improvement of her condition.

Example 13

Therapy of a Gastric Cancer Patient with Stage IV Metastatic Disease with Sacituzumab Govitecan (IMMU-132) Plus Paclitaxel This patient is a 60-year-old male with a history of smoking and periods of excessive alcohol intake over a 40-year-period. He experiences weight loss, eating discomfort and pain not relieved by antacids, frequent abdominal pain, lower back pain, and most recently palpable nodes in both axilla. He seeks medical advice, and after a workup is shown to have an adenocarcinoma, including some squamous features, at the gastro-esophageal junction, based on biopsy via a gastroscope. Radiological studies (CT and FDG-PET) also reveal metastatic disease in the right and left axilla, mediastinal region, lumbar spine, and liver (2 tumors in the right lobe and 1 in the left, all measuring between 2 and 4 cm in diameter). His gastric tumor is resected and he is then put on a course of chemotherapy with epirubicin, cisplatin, and 5-fluorouracil. After 4 months and a rest period of 6 weeks, he is switched to docetaxel chemotherapy, which also fails to control his disease, based on progression confirmed by CT measurements of the metastatic tumors and some general deterioration.

The patient is then given combination therapy with IMMU-132 (hRS7-SN-38) and paclitaxel on a 21 day cycle. Paclitaxel is administered at a dosage of 175 mg/m$^2$ on days 1, 7 and 14 of the cycle. IMMU-132 is administered at 10 mg/kg on days 1 and 8 of the cycle. After 3 cycles CT studies are done to assess status of his disease. The infusions are tolerated well, with some mild nausea and diarrhea, and also with Grade 3 neutropenia, controlled with symptomatic medications and with G-CSF (Neulasta®) for the neutropenia. The CT studies reveal that the sum of his index metastatic lesions has decreased by 28%, so he continues on this therapy for another 5 cycles. Follow-up CT studies show that the disease remains about 35% reduced by RECIST criteria from his baseline measurements prior to combination therapy, and his general condition also appears to have improved, with the patient regaining an optimistic attitude toward his disease being under control.

Example 14

Therapy of Advanced Colon Cancer Patient Refractory to Prior Chemo-Immunotherapy, Using Only IMMU-130 (labetuzumab-SN-38)

Figure 9:
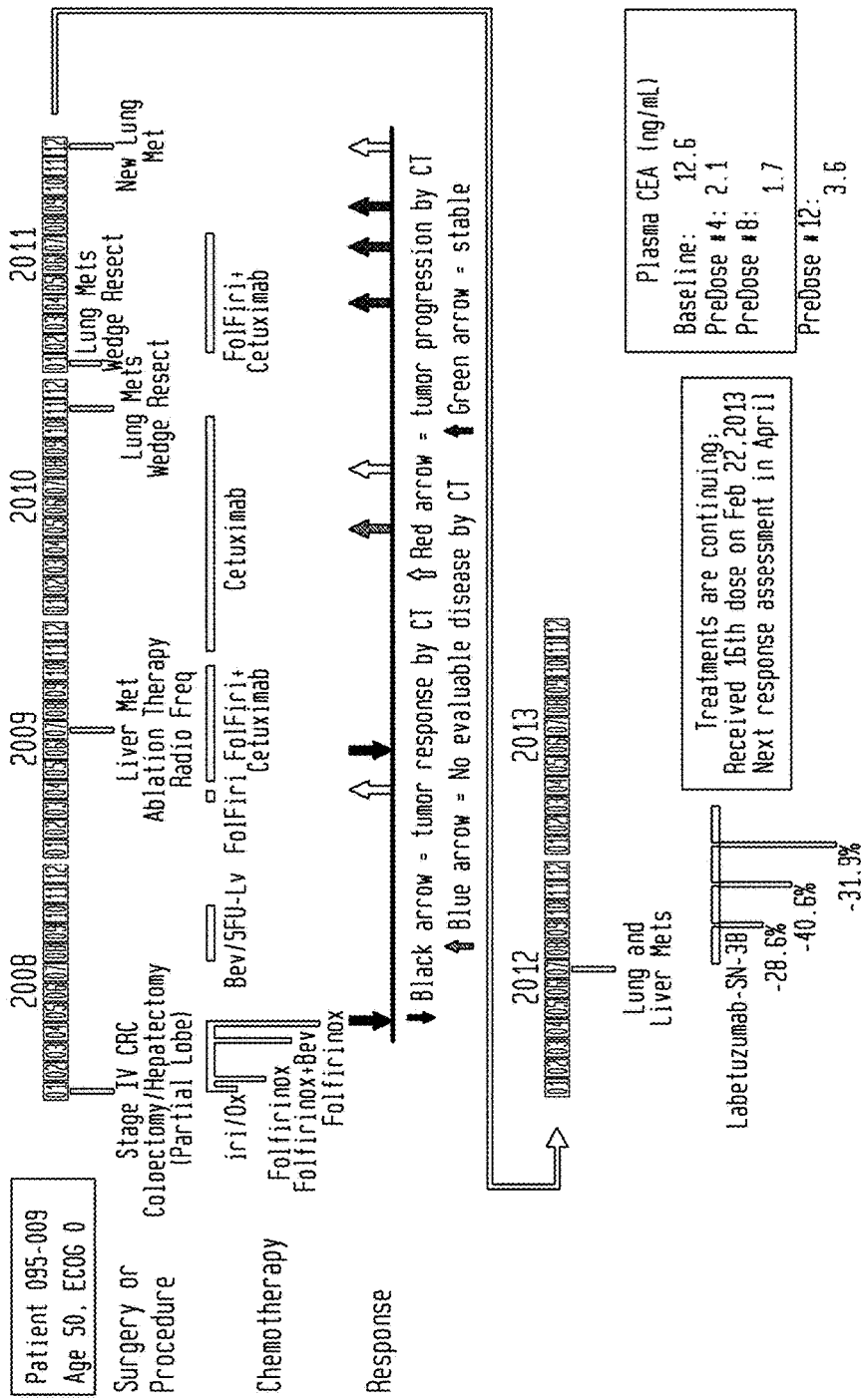
FIG. 9. History of prior treatment of patient, before administering IMMU-130 (labetuzumab-SN-38). Prior treatment included stage IV CRC coloectomy/hepatectomy (partial lobe), radiofrequency ablation therapy of liver metasteses, wedge resection of lung metasteses, and chemotherapy with irinotecan/oxaliplatin, Folfirinox, Folfirinox+bevacizumab, bevacizumab+5-FU/leucovorin, Folfiri, Folfiri+cetuximab, and cetuximab alone. The patient received doses of 16 mg/kg of IMMU-130 by slow IV infusion every other week for a total of 17 treatment doses.

The patient is a 50-year-old man with a history of stage-IV metastatic colonic cancer, first diagnosed in 2008 and given a colectomy and partial hepatectomy for the primary and metastatic colonic cancers, respectively. He then received chemotherapy, as indicated FIG. 9, which included irinotecan, oxaliplatin, FOLFIRINOX (5-fluoruracil, leucovorin, irinotecan, oxaliplatin), and bevacizumab, as well as bevacizumab combined with 5-fluorouracil/leucovorin, for almost 2 years. Thereafter, he was given courses of cetuximab, either alone or combined with FOLFIRI (leucovorin, 5-flurouracil, irinotecan) chemotherapy during the next year or more. In 2009, he received radiofrequency ablation therapy to his liver metastasis while under chemo-immunotherapy, and in late 2010 he underwent a wedge resection of his lung metastases, which was repeated a few months later, in early 2011. Despite having chemo-immunotherapy in 2011, new lung metastases appeared at the end of 2011, and in 2012, both lung and liver metastases were visualized. His baseline plasma carcinoembryonic antigen (CEA) titer was 12.5 ng/mL just before undergoing the antibody-drug therapy with IMMU-130. The index lesions chosen by the radiologist for measuring tumor size change by computed tomography were the mid-lobe of the right lung and the liver metastases, both totaling 91 mm as the sum of their longest diameters at the baseline prior to IMMU-130 (anti-CEACAM5-SN-38) therapy.

This patient received doses of 16 mg/kg of IMMU-130 by slow IV infusion every other week for a total of 17 treatment doses. The patient tolerated the therapy well, having only a grade 1 nausea, diarrhea and fatigue after the first treatment, which occurred after treatments 4 and 5, but not thereafter, because he received medication for these side-effects. After treatment 3, he did show alopecia (grade 2), which was present during the subsequent therapy. The nausea, diarrhea, and occasional vomiting lasted only 2-3 days, and his fatigue after the first infusion lasted 2 weeks. Otherwise, the patient tolerated the therapy well. Because of the long duration of receiving this humanized (CDR-grafted) antibody conjugated with SN-38, his blood was measured for anti-labetuzumab antibody, and none was detected, even after 16 doses.

The first computed tomography (CT) measurements were made after 4 treatments, and showed a 28.6% change from the sum of the measurements made at baseline, prior to this therapy, in the index lesions. After 8 treatments, this reduction became 40.6%, thus constituting a partial remission according to RECIST criteria. This response was maintained for another 2 months, when his CT measurements indicated that the index lesions were 31.9% less than the baseline measurements, but somewhat higher than the previous decrease of 40.6% measured. Thus, based on careful CT measurements of the index lesions in the lung and liver, this patient, who had failed prior chemotherapy and immunotherapy, including irinotecan (parent molecule of SN-38), showed an objective response to the active metabolite of irintotecan (or camptotechin), SN-38, when targeted via the anti-CEACAM5 humanized antibody, labetuzumab (hMN-14). It was surprising that although irinotecan (CPT-11) acts by releasing SN-38 in vivo, the SN-38 conjugated anti-CEACAM5 antibody proved effective in a colorectal cancer patient by inducing a partial response after the patient earlier failed to respond to his last irinotecan-containing therapy. The patient's plasma CEA titer reduction also corroborated the CT findings: it fell from the baseline level of 12.6 ng/mL to 2.1 ng/mL after the third therapy dose, and was between 1.7 and 3.6 ng/mL between doses 8 and 12. The normal plasma titer of CEA is usually considered to be between 2.5 and 5.0 ng/mL, so this therapy effected a normalization of his CEA titer in the blood.

Example 15

Immunoconjugate Storage

The ADC conjugates are were purified and buffer-exchanged with 2-(N-morpholino)ethanesulfonic acid (MES), pH 6.5, and further formulated with trehalose (25 mM final concentration) and polysorbate 80 (0.01% v/v final concentration), with the final buffer concentration becoming 22.25 mM as a result of excipient addition. The formulated conjugates are lyophilized and stored in sealed vials, with storage at 2° C.-8° C. The lyophilized ADCs are stable under the storage conditions and maintain their physiological activities for over 12 months.

From the foregoing description, one skilled in the art can easily ascertain the essential characteristics of this invention, and without departing from the spirit and scope thereof, can make various changes and modifications of the invention to adapt it to various usage and conditions without undue experimentation. All patents, patent applications and publications cited herein are incorporated by reference.

What is claimed is:

1. A method of treating cancer, consisting of: a) administering to a human subject with a cancer that expresses Trop-2 an antibody-drug conjugate (ADC), wherein the ADC is sacituzumab govitecan; and b) administering to the human subject at least one checkpoint inhibitor selected from the group consisting of tremelimumab, atezolizumab, durvalumab, avelumab, pidilizumab, and BMS936559.

2. The method of claim 1, wherein the cancer is selected from the group consisting of colon cancer, stomach cancer, esophageal cancer, medullary thyroid cancer, kidney cancer, breast cancer, lung cancer, pancreatic cancer, urinary bladder cancer, ovarian cancer, uterine cancer, cervical cancer, testicular cancer, prostate cancer, liver cancer, skin cancer, bone cancer, brain cancer, rectal cancer, and melanoma.

3. The method of claim 1, wherein the cancer is selected from the group consisting of triple-negative breast cancer, ovarian cancer, endometrial cancer, urothelial cancer, non-small-cell lung cancer, small-cell lung cancer and metastatic colorectal cancer.

4. The method of claim 1, wherein the cancer is triple negative breast cancer or urothelial cancer.

5. The method of claim 1, wherein the checkpoint inhibitor is durvalumab.

6. The method of claim 1, wherein the patient has not previously been treated with an anti-cancer therapy.

7. The method of claim 1, wherein the patient has relapsed from or been resistant to at least one anti-cancer therapy.

8. The method of claim 1, wherein the ADC is administered at a dosage of between 4 mg/kg and 16 mg/kg.

9. The method of claim 1, wherein the ADC is administered at a dosage of between 8 mg/kg and 10 mg/kg.

10. The method of claim 8, wherein the dosage is selected from the group consisting of 6 mg/kg, 8 mg/kg, 9 mg/kg, 10 mg/kg, and 12 mg/kg.

11. The method of claim 1, wherein the cancer is a solid tumor and the treatment results in a reduction in tumor size of at least 15%, at least 20%, at least 30%, or at least 40%.

12. The method of claim 1, wherein the cancer is metastatic.

13. The method of claim 12, further comprising reducing in size or eliminating the metastases.

* * * * *

SEQUENCE LISTING

```
<160> NUMBER OF SEQ ID NOS: 8

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Ala Ser Gln Asp Val Ser Ile Ala Val Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Ala Ser Tyr Arg Tyr Thr
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Gln His Tyr Ile Thr Pro Leu Thr
1               5

<210> SEQ ID NO 4
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asn Tyr Gly Met Asn
1               5

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Trp Ile Asn Thr Tyr Thr Gly Glu Pro Thr Tyr Thr Asp Asp Phe Lys
1               5                   10                  15

Gly

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Gly Phe Gly Ser Ser Tyr Trp Tyr Phe Asp Val
1               5                   10

<210> SEQ ID NO 7
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Ala Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140
```

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 8
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175
```

```
            Glu Gln Tyr Asn Ser Thr Tyr Arg Val Val Ser Val Leu Thr Val Leu
                        180             185             190

His Gln Asp Trp Leu Asn Gly Lys Glu Tyr Lys Cys Lys Val Ser Asn
                    195             200             205

Lys Ala Leu Pro Ala Pro Ile Glu Lys Thr Ile Ser Lys Ala Lys Gly
                210             215             220

Gln Pro Arg Glu Pro Gln Val Tyr Thr Leu Pro Pro Ser Arg Glu Glu
            225             230             235             240

Met Thr Lys Asn Gln Val Ser Leu Thr Cys Leu Val Lys Gly Phe Tyr
                        245             250             255

Pro Ser Asp Ile Ala Val Glu Trp Glu Ser Asn Gly Gln Pro Glu Asn
                        260             265             270

Asn Tyr Lys Thr Thr Pro Pro Val Leu Asp Ser Asp Gly Ser Phe Phe
                    275             280             285

Leu Tyr Ser Lys Leu Thr Val Asp Lys Ser Arg Trp Gln Gln Gly Asn
                    290             295             300

Val Phe Ser Cys Ser Val Met His Glu Ala Leu His Asn His Tyr Thr
            305             310             315             320

Gln Lys Ser Leu Ser Leu Ser Pro Gly Lys
                        325             330
```